United States Patent
Oku et al.

(10) Patent No.: US 6,344,462 B1
(45) Date of Patent: Feb. 5, 2002

(54) HETEROCYCLIC COMPOUNDS AS BRADYKININ ANTAGONISTS

(75) Inventors: Teruo Oku; Hiroshi Kayakiri, both of Tsukuba; Yoshito Abe, Inashiki-gun; Yuki Sawada; Tsuyoshi Mizutani, both of Tsukuba, all of (JP)

(73) Assignee: Fujisawa Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/604,526

(22) Filed: Jun. 27, 2000

Related U.S. Application Data

(62) Division of application No. 09/419,684, filed on Oct. 15, 1999, now Pat. No. 6,100,284, which is a division of application No. 09/029,852, filed as application No. PCT/JP96/02669 on Sep. 18, 1996, now Pat. No. 6,008,229.

(30) Foreign Application Priority Data

Sep. 18, 1995 (GB) ............................................. 9519077

(51) Int. Cl.$^7$ ........................ A61K 31/44; C07D 471/02
(52) U.S. Cl. ........................................ 514/300; 546/121
(58) Field of Search .......................... 546/121; 514/300

(56) References Cited

U.S. PATENT DOCUMENTS

| 5,563,162 A | 10/1996 | Oku et al. |
| 5,574,042 A | 11/1996 | Oku et al. |
| 5,708,173 A | 1/1998 | Oku et al. |
| 5,750,699 A | 5/1998 | Oku et al. |

FOREIGN PATENT DOCUMENTS

| EP | 0 596 406 | 5/1994 |
| EP | 0 622 361 | 11/1994 |
| WO | WO 96/04251 | 2/1996 |
| WO | WO 96/13485 | 5/1996 |

Primary Examiner—D. Margaret Seaman
(74) Attorney, Agent, or Firm—Oblon, Spivak, McClelland, Maier & Neustadt, P.C.

(57) ABSTRACT

This invention relates to a compound of the formula:

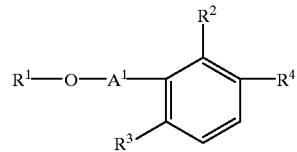

wherein
$A^1$ is lower alkylene,
$R^1$ is substituted quinolyl, etc.,
$R^2$ is hydrogen, halogen or lower alkyl,
$R^3$ is halogen or lower alkyl, and
$R^4$ is a group of the formula:

—Q—$A^2$—$R^5$, etc., in which
$R^5$ is amino, acylamino, etc.,
$A^2$ is lower alkylene or a single bond, and
Q is a group of the formula:

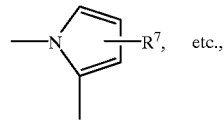

and pharmaceutically acceptable salts thereof, to processes for preparation thereof, to a pharmaceutical composition comprising the same, and to methods of using the same therapeutically in the prevention and/or the treatment of bradykinin or its analogues mediated diseases in human being or animals.

11 Claims, No Drawings

HETEROCYCLIC COMPOUNDS AS BRADYKININ ANTAGONISTS

This application is a divisional of U.S. application Ser. No. 09/419,684, filed Oct. 15, 1999, now U.S. Pat. No. 6,100,284, which is a divisional of U.S. application Ser. No. 09/029,852, filed Mar. 13, 1998, now U.S. Pat. No. 6,008,229, which was filed as International Application No. PCT/JP96/02669, filed Sep. 18, 1996.

TECHNICAL FIELD

This invention relates to new heterocyclic compounds and pharmaceutically acceptable salts thereof.

More particularly, it relates to new heterocyclic compounds and pharmaceutically acceptable salts thereof which have activities as bradykinin antagonists, to processes for preparation thereof, to a pharmaceutical composition comprising the same, and to methods of using the same therapeutically in the prevention and/or the treatment of bradykinin or its analogues mediated diseases such as allergy, inflammation, autoimmune disease, shock, pain, or the like, in human being or animals.

One object of this invention is to provide new and useful heterocyclic compounds and pharmaceutically acceptable salts thereof which possess activities as bradykinin antagonists.

Another object of this invention is to provide processes for the preparation of said compounds and salts thereof.

A further object of this invention is to provide a pharmaceutical composition comprising, as an active ingredient, said heterocyclic compounds and pharmaceutically acceptable salts thereof.

Still further object of this invention is to provide a therapeutical method for the prevention and/or the treatment of bradykinin or its analogues mediated diseases such as allergy, inflammation, autoimmune disease, shock, pain, or the like, using said heterocyclic compounds and pharmaceutically acceptable salts thereof.

BACKGROUND ART

Some heterocyclic compounds have been known as described, for example, in EP-A-224,086, EP-A-261,539, Chemical Abstracts 90:34849g (1979), or Chemical Abstracts 97:18948c (1982). However, it is not known that said compounds have activities as bradykinin antagonists.

Heterocyclic compounds having activities as bradykinin antagonists have been known as described in EP-A-596,406, EP-A-622,361, WO-A-96/04251, WO-A-96/13485 and U.S. Pat. No. 5,212,182.

DISCLOSURE OF THE INVENTION

The object heterocyclic compounds of this invention are new and can be represented by the following general formula [I]:

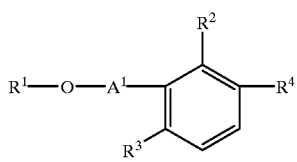

[I]

wherein
A$^1$ is lower alkylene,
R$^1$ is quinolyl, quinazolinyl, quinoxalinyl, benzimidazolyl, benzofuryl, benzoxazolyl or imidazopyridyl, each of which is substituted with substituent(s) selected from the group consisting of halogen, lower alkyl, lower alkoxy, lower alkylamino and a heterocyclic group,
R$^2$ is hydrogen, halogen or lower alkyl,
R$^3$ is halogen or lower alkyl, and
R$^4$ is carboxy, lower alkanoyl or a group of the formula:

or

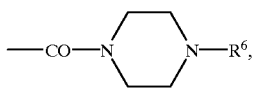

in which
R$^5$ is amino, acylamino, cyano, hydroxy, hydroxyimino (lower)alkyl or acyl,
R$^6$ is hydrogen or acyl,
A$^2$ is lower alkylene or a single bond, and
Q is lower alkenylene or a group of the formula:

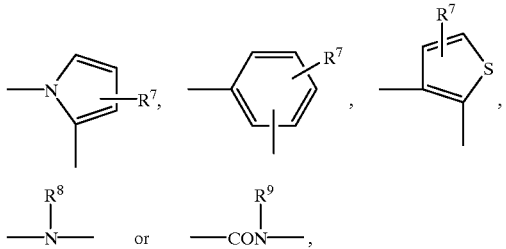

in which
R$^7$ is hydrogen or halogen;
R$^8$ is hydrogen, or
R$^8$ and R$^2$ are taken together to form lower alkylene; and
R$^9$ is hydrogen, lower alkyl or ar(lower)alkyl; provided that A$^2$ is lower alkylene when R$^8$ is hydrogen.

The object compound [I] or its salt can be prepared by processes as illustrated in the following reaction schemes.

Process 1

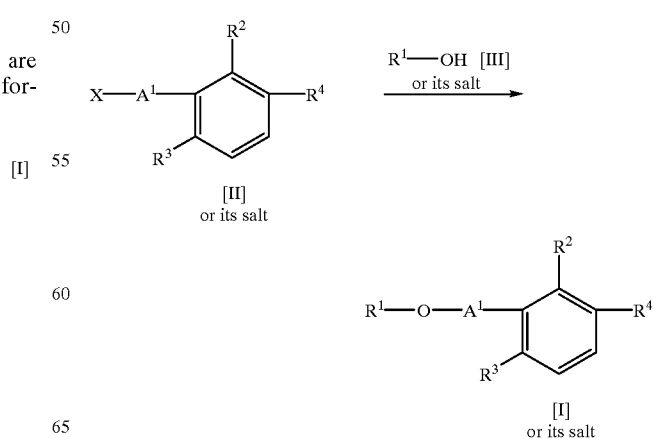

Process 2
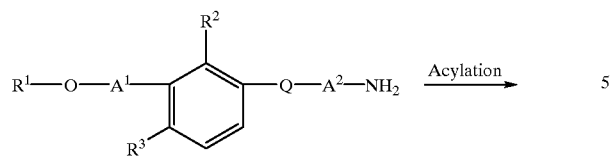
[Ia]
or its salt
Acylation
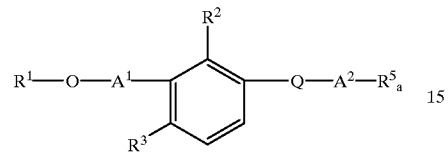
[Ib]
or its salt
Process 3
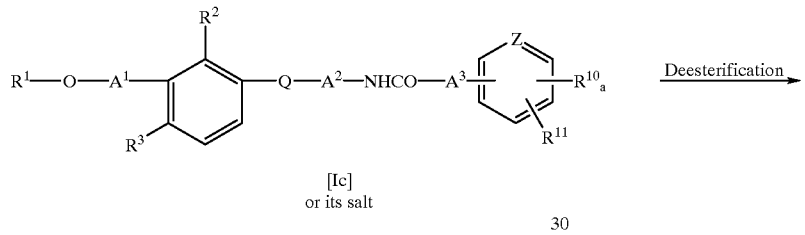
[Ic]
or its salt
Deesterification
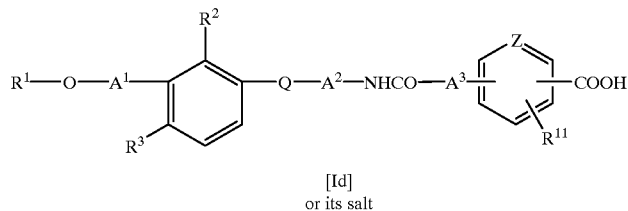
[Id]
or its salt
Process 4
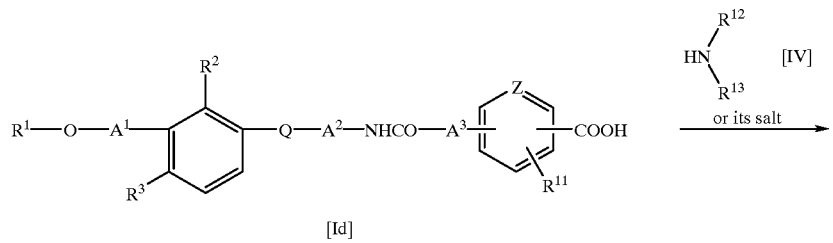
[Id]
or its reactive derivative at the carboxy group or a salt thereof
$$HN\begin{matrix}R^{12}\\R^{13}\end{matrix}\quad[IV]$$
or its salt
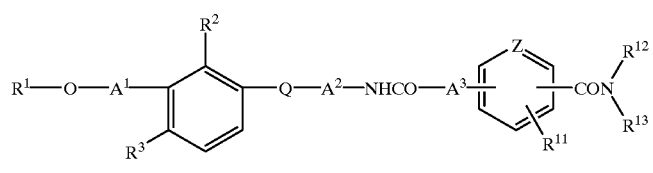
[Ie]
or its salt wherein $R_a^5$ is acylamino,
$R_a^{10}$ is esterified carboxy,
$R^{11}$ is hydrogen, lower alkyl or lower alkoxy,
$R^{12}$ is hydrogen, lower alkyl, heterocyclic(lower)alkyl, a heterocyclic group, lower alkanoyl, lower alkoxy (lower)alkanoyl, heterocycliccarbonyl optionally substituted with lower alkyl, or lower alkylsulfonyl, and
$R^{13}$ is hydrogen, lower alkyl or heterocyclic(lower) alkyl, or
$R^{12}$ and $R^{13}$ are taken together with the attached nitrogen atom to form a heterocyclic group optionally substituted with oxo,
$A^3$ is —NH—, lower alkylene or lower alkenylene,
X is a leaving group,
Z is CH or N, and
$R^1, R^2, R^3, R^4, A^1, A^2$ and Q are each as defined above.

In the above and subsequent description of the present specification and claims, suitable examples of the various definitions to be included within the scope of the invention are explained in detail in the following.

The term "lower" is intended to mean a group having 1 to 6 carbon atom(s), unless otherwise provided.

In this respect, the term "lower" in lower alkenoyl moiety, lower alkynoyl moiety, cyclo(lower)alkyl moiety, cyclo (lower)alkenyl moiety, ar(lower)alkenoyl moiety, ar(lower) alkynoyl moiety and heterocyclic(lower)alkenoyl moiety in the various definitions is intended to mean a group having 3 to 6 carbon atoms.

Suitable "halogen" may be fluorine, chlorine, bromine and iodine.

Suitable "lower alkyl" and lower alkyl moiety in the terms "heterocyclic(lower)alkyl", "lower alkylamino", "ar(lower) alkyl" and "hydroxyimino(lower)alkyl" may be straight or branched one such as methyl, ethyl, propyl, isopropyl, butyl, isobutyl, tert-butyl, pentyl, hexyl or the like, in which preferable one is $C_1$–$C_4$ alkyl such as methyl, ethyl, propyl, isobutyl or tert-butyl.

Suitable "lower alkoxy" may be straight or branched one such as methoxy, ethoxy, propoxy, isopropoxy, butoxy, isobutoxy, tert-butoxy, pentyloxy, hexyloxy or the like, in which preferable one is $C_1$–$C_4$ alkoxy such as methoxy, ethoxy or isopropoxy.

Suitable "lower alkylene" may be a straight or branched one such as methylene, ethylene, trimethylene, methylmethylene, tetramethylene, ethylethylene, propylene, pentamethylene, hexamethylene or the like, in which the most preferable one is methylene.

Suitable "acyl" and acyl moiety in the term "acylamino" may be substituted or unsubstituted alkanoyl such as alkanoyl [e.g. formyl, acetyl, propionyl, butyryl, isobutyryl, valeryl, isovaleryl, pivaloyl, hexanoyl, heptanoyl, 3,3-dimethylbutyryl, etc.], halo(lower)alkanoyl [e.g. chloroacetyl, trifluoroacetyl, bromoacetyl, bromobutyryl, heptafluorobutyryl, etc.], hydroxy(lower)alkanoyl [e.g. glycoloyl, lactoyl, 3-hydroxypropionyl, glyceroyl, etc.], lower alkylsulfonyloxy(lower)alkanoyl [e.g. mesyloxyacetyl, ethylsulfonyloxyacetyl, mesyloxypropionyl, etc.], lower alkoxy(lower)alkanoyl [e.g. methoxyacetyl, ethoxyacetyl, methoxypropionyl, ethoxypropionyl, propoxypropionyl, methoxybutyryl, etc.], lower alkylthio(lower)alkanoyl [e.g. methylthioacetyl, ethylthioacetyl, methylthiopropionyl, ethylthiopropionyl, propylthiopropionyl, methylthiobutyryl, etc.], lower alkanoyloxy(lower)alkanoyl [e.g. acetyloxyacetyl, acetyloxypropionyl, propionyloxyacetyl, etc.], aryloxy (lower)alkanoyl [e.g. phenyloxyacetyl, phenyloxypropionyl, tolyloxyacetyl, naphthyloxyacetyl, etc.], aroyl(lower) alkanoyl [e.g. phenyloxalyl, benzoylacetyl, benzoylpropionyl, etc.], carboxy(lower)alkanoyl [e.g. oxalo, carboxyacetyl, 3-carboxypropionyl, 3-carboxybutyryl, 4-carboxybutyryl, 4-carboxyvaleryl, etc.], esterified carboxy (lower)alkanoyl, for example, lower alkoxycarbonyl(lower) alkanoyl [e.g. methoxycarbonylacetyl, ethoxycarbonylacetyl, methoxycarbonylpropionyl, ethoxycarbonylpropionyl, etc.], carbamoyl(lower)alkanoyl [e.g. carbamoylacetyl, carbamoylpropionyl, etc.], lower alkylcarbamoyl(lower)alkanoyl [e.g. methylcarbamoylacetyl, methylcarbamoylpropionyl, ethylcarbamoylpropionyl, dimethylcarbamoylpropionyl, (N-methyl-N-ethylcarbamoyl)propionyl, etc.], ar(lower) alkanoyl [e.g. phenylacetyl, tolylacetyl, naphthylacetyl, 2-phenylpropionyl, 3-phenylpropionyl, 4-phenylbutyryl, tritylcarbonyl, etc.], heterocyclic(lower)alkylcarbamoyl-ar (lower)alkanoyl [e.g. pyridylmethylcarbamoylphenylpropionyl, furylmethylcarbamoylphenylpropionyl, etc.], optionally substituted heterocyclic(lower)alkanoyl [e.g. morpholinoacetyl, thiomorpholinoacetyl, morpholinopropionyl, thiomorpholinopropionyl, piperidinopropionyl, piperazinylpropionyl, pyridylacetyl, pyrrolidinylpropionyl, imidazolidinylpropionyl, piperidinoacetyl, pyrrolidinylacetyl, hexamethyleneiminoacetyl, hexamethyleneiminopropionyl, imidazolylacetyl, furylacetyl, thienylacetyl, methylpiperazinylacetyl, pyridylpiperazinylacetyl, etc.], heterocyclicthio(lower)alkanoyl [e.g. pyridylthioacetyl, pyrimidinylthioacetyl, imidazolylthiopropionyl, etc.], etc., lower alkenoyl [e.g. acryloyl, crotonoyl, isocrotonoyl, 3-butenoyl, 3-pentenoyl, 4-pentenoyl, methacryloyl, etc.], lower alkynoyl [e.g. propioloyl, 2-butynoyl, 3-butynoyl, etc.], cyclo(lower)alkylcarbonyl [e.g. cyclopropylcarbonyl, cyclobutylcarbonyl, cyclopentylcarbonyl, cyclohexylcarbonyl, etc.], cyclo(lower)alkenylcarbonyl [e.g. cyclopentenylcarbonyl, cyclohexenylcarbonyl, etc.], carboxy, esterified carboxy such as lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], aryloxycarbonyl [e.g. phenoxycarbonyl, etc.], etc., substituted or unsubstituted aroyl such as aroyl [e.g. benzoyl, toluoyl, xyloyl, naphthoyl, etc.], lower alkoxyaroyl [e.g. methoxybenzoyl, etc.], haloaroyl [e.g. chlorobenzoyl, fluorobenzoyl, etc.], acylaroyl, for example, lower alkoxycarbonylaroyl [e.g. methoxycarbonylbenzoyl, etc.], or lower alkylcarbamoylaroyl [e.g. methylcarbamoylbenzoyl, dimethylcarbamoylbenzoyl, etc.], etc., substituted or unsubstituted ar(lower)alkenoyl such as ar(lower)alkenoyl [e.g. cinnamoyl, allocinnamoyl, α-methylcinnamoyl, 4-methylcinnamoyl, etc.], lower alkoxy-ar(lower)alkenoyl [e.g. methoxycinnamoyl, ethoxycinnamoyl, dimethoxycinnamoyl, etc.], lower alkylenedioxy-ar(lower) alkenoyl [e.g. methylenedioxycinnamoyl, ethylenedioxycinnamoyl, etc.], nitro-ar(lower)alkenoyl [e.g. nitrocinnamoyl, etc.], cyano-ar(lower)alkenoyl [e.g. cyanocinnamoyl, etc.], halo-ar(lower)alkenoyl [e.g. chlorocinnamoyl, fluorocinnamoyl, etc.], hydroxy-ar(lower) alkenoyl [e.g. hydroxycinnamoyl, etc.], hydroxy(lower) alkoxy-ar(lower)alkenoyl [e.g. hydroxymethoxycinnamoyl, hydroxyethoxycinnamoyl, etc.], amino(lower)alkoxy-ar (lower)alkenoyl [e.g. aminoethoxycinnamoyl, etc.], lower alkylamino(lower)alkoxy-ar(lower)alkenoyl [e.g. methylaminomethoxycinnamoyl, dimethylaminoethoxycinnamoyl, etc.], heterocyclic(lower)

alkoxy-ar(lower)alkenoyl [e.g. pyridylmethoxycinnamoyl, etc.], optionally substituted heterocyclic-ar(lower)alkenoyl [e.g. morpholinocinnamoyl, methylpiperazinylcinnamoyl, pyrrolidinylcinnamoyl, oxopyrrolidinylcinnamoyl, oxopiperidinocinnamoyl, dioxopyrrolidinylcinnamoyl, oxooxazolidinylcinnamoyl, pyrrolylcinnamoyl, tetrazolylcinnamoyl, etc.], heterocyclic(lower)alkenyl-ar(lower)alkenoyl [e.g. pyridylvinylcinnamoyl, etc.], amino-ar(lower)alkenoyl [e.g. aminocinnamoyl, etc.], lower alkylamino-ar(lower)alkenoyl [e.g. methylaminocinnamoyl, dimethylaminocinnamoyl, etc.], acylamino-ar(lower)alkenoyl, for example, lower alkanoylamino-ar(lower)alkenoyl [e.g. acetylaminocinnamoyl, propionylaminocinnamoyl, isobutyrylaminocinnamoyl, 4-acetylamino-3-methylcinnamoyl, etc.], cycloalkyl(lower)alkanoylamino-ar(lower)alkenoyl [e.g. cyclopentylacetylaminocinnamoyl, cyclohexylacetylaminocinnamoyl, adamantylacetylaminocinnamoyl, etc.], cycloalkylcarbonylamino-ar(lower)alkenoyl [e.g. cyclopropylcarbonylaminocinnamoyl, cyclopentylcarbonylaminocinnamoyl, cyclohexylcarbonylaminocinnamoyl, adamantylcarbonylaminocinnamoyl, etc.], lower alkenoylamino-ar(lower)alkenoyl [e.g. acryloylaminocinnamoyl, crotonoylaminocinnamoyl, etc.], lower alkoxycarbonylamino-ar(lower)alkenoyl [e.g. methoxycarbonylaminocinnamoyl, ethoxycarbonylaminocinnamoyl, etc.], hydroxy(lower)alkanoylamino-ar(lower)alkenoyl [e.g. hydroxyacetylaminocinnamoyl, hydroxypropionylaminocinnamoyl, etc.], lower alkoxy(lower)alkanoylamino-ar(lower)alkenoyl [e.g. methoxyacetylaminocinnamoyl, methoxypropionylaminocinnamoyl, etc.], halo(lower)alkanoylamino-ar(lower)alkenoyl [e.g. chloroacetylaminocinnamoyl, bromobutyrylaminocinnamoyl, trifluoroacetylaminocinnamoyl, etc.], amino(lower)alkanoylamino-ar(lower)alkenoyl [e.g. aminoacetylaminocinnamoyl, aminopropionylaminocinnamoyl, etc.], lower alkylamino(lower)alkanoylamino-ar(lower)alkenoyl [e.g. methylaminoacetylaminocinnamoyl, dimethylaminoacetylaminocinnamoyl, etc.], lower alkanoylamino(lower)alkanoylamino-ar(lower)alkenoyl [e.g. acetylaminoacetylaminocinnamoyl, acetylaminopropionylaminocinnamoyl, etc.], carboxy(lower)alkanoylamino-ar(lower)alkenoyl [e.g. carboxyacetylaminocinnamoyl, carboxypropionylaminocinnamoyl, etc.], lower alkoxycarbonyl(lower)alkanoylamino-ar(lower)alkenoyl [e.g. ethoxycarbonylacetylaminocinnamoyl, ethoxycarbonylpropionylaminocinnamoyl, etc.], lower alkoxycarbonyl(lower)alkenoylamino-ar(lower)alkenoyl [e.g. ethoxycarbonylacryloylaminocinnamoyl, etc.], halo(lower)alkoxycarbonylamino-ar(lower)alkenoyl [e.g. chloroethoxycarbonylaminocinnamoyl, etc.], optionally substituted heterocyclic(lower)alkanoylamino-ar(lower)alkenoyl [e.g. pyridylacetylaminocinnamoyl, thienylacetylaminocinnamoyl, methylpyrrolylacetylaminocinnamoyl, etc.], aroylamino-ar(lower)alkenoyl [e.g. benzoylaminocinnamoyl, etc.], optionally substituted heterocycliccarbonylamino-ar(lower)alkenoyl [e.g. pyridylcarbonylaminocinnamoyl, morpholinocarbonylaminocinnamoyl, furylcarbonylaminocinnamoyl, thienylcarbonylaminocinnamoyl, oxazolylcarbonylaminocinnamoyl, methyloxazolylcarbonylaminocinnamoyl, dimethylisoxazolylcarbonylaminocinnamoyl, imidazolylcarbonylaminocinnamoyl, methylimidazolylcarbonylaminocinnamoyl, piperidylcarbonylaminocinnamoyl, ethylpiperidylcarbonylaminocinnamoyl, acetylpiperidylcarbonylaminocinnamoyl, pyrrolidinylcarbonylaminocinnamoyl, acetylpyrrolidinylcarbonylaminocinnamoyl, tert-butoxycarbonylpyrrolidinylcarbonylaminocinnamoyl, etc.], lower alkylsulfonylamino-ar(lower)alkenoyl [e.g. mesylaminocinnamoyl, ethylsulfonylaminocinnamoyl, etc.], etc., N-(lower alkanoyl)-N-(lower alkyl)amino-ar(lower)alkenoyl [e.g. N-acetyl-N-methylaminocinnamoyl, N-acetyl-N-ethylaminocinnamoyl, N-propionyl-N-methylaminocinnamoyl, etc.], N-[lower alkoxy(lower)alkanoyl]-N-(lower alkyl)amino-ar(lower)alkenoyl [e.g. N-methoxyacetyl-N-methylaminocinnamoyl, N-methoxypropionyl-N-methylaminocinnamoyl, etc.], N-(lower alkanoyl)-N-[heterocyclic(lower)alkyl]amino-ar(lower)alkenoyl [e.g. N-acetyl-N-pyridylmethylaminocinnamoyl, etc.], N-(lower alkanoyl)-N-[lower alkoxy(lower)alkyl]amino-ar(lower)alkenoyl [e.g. N-acetyl-N-methoxyethylaminocinnamoyl, N-acetyl-N-methoxymethylaminocinnamoyl, N-propionyl-N-methoxyethylaminocinnamoyl, etc.], N-(lower alkanoyl)-N-[lower alkoxycarbonyl(lower)alkyl]amino-ar(lower)alkenoyl [e.g. N-acetyl-N-tert-butoxycarbonylmethylaminocinnamoyl, N-acetyl-N-tert-butoxycarbonylethylaminocinnamoyl, N-propionyl-N-tert-butoxycarbonylmethylaminocinnamoyl, etc.], N-(lower alkanoyl)-N-[carboxy(lower)alkyl]amino-ar(lower)alkenoyl [e.g. N-acetyl-N-carboxymethylaminocinnamoyl, N-acetyl-N-carboxyethylaminocinnamoyl, N-propionyl-N-carboxymethylaminocinnamoyl, etc.], N-[lower alkoxy(lower)alkanoyl]-N-[heterocyclic(lower)alkyl]amino-ar(lower)alkenoyl [e.g. N-methoxyacetyl-N-pyridylmethylaminocinnamoyl, N-methoxypropionyl-N-pyridylmethylaminocinnamoyl, etc.], N-[heterocycliccarbonyl]-N-[lower alkoxy(lower)alkyl]amino-ar(lower)alkenoyl [e.g. N-pyridylcarbonyl-N-methoxymethylaminocinnamoyl, N-pyridylcarbonyl-N-methoxyethylaminocinnamoyl, N-thienylcarbonyl-N-methoxyethylaminocinnamoyl, etc.], ureido-ar(lower)alkenoyl [e.g. ureidocinnamoyl, etc.], lower alkylureido-ar(lower)alkenoyl [e.g. methylureidocinnamoyl, ethylureidocinnamoyl, dimethylureidocinnamoyl, etc.], heterocyclicureido-ar(lower)alkenoyl [e.g. pyridylureidocinnamoyl, pyrimidinylureidocinnamoyl, thienylureidocinnamoyl, etc.], acyl-ar(lower)alkenoyl, for example, lower alkanoyl-ar(lower)alkenoyl [e.g. formylcinnamoyl, acetylcinnamoyl, propionylcinnamoyl, etc.], carboxy-ar(lower)alkenoyl [e.g. carboxycinnamoyl, etc.], lower alkoxycarbonyl-ar(lower)alkenoyl [e.g. methoxycarbonylcinnamoyl, ethoxycarbonylcinnamoyl, etc.], carbamoyl-ar(lower)alkenoyl [e.g. carbamoylcinnamoyl, etc.], lower alkylcarbamoyl-ar(lower)alkenoyl [e.g. methylcarbamoylcinnamoyl, ethylcarbamoylcinnamoyl, dimethylcarbamoylcinnamoyl, propylcarbamoylcinnamoyl, isopropylcarbamoylcinnamoyl, diethylcarbamoylcinnamoyl, N-methyl-N-ethylcarbamoylcinnamoyl, etc.], (lower alkylcarbamoyl)(lower alkoxy)-ar(lower)alkenoyl [e.g. 4-methylcarbamoyl-3-methoxycinnamoyl, 4-dimethylcarbamoyl-3-methoxycinnamoyl, etc.], hydroxy(lower)alkylcarbamoyl-ar (lower)alkenoyl [e.g. hydroxyethylcarbamoylcinnamoyl, bis(hydroxyethyl)carbamoylcinnamoyl, etc.], N-[hydroxy(lower)alkyl]-N-(lower alkyl)carbamoyl-ar(lower)alkenoyl [e.g. N-hydroxyethyl-N-methylcarbamoylcinnamoyl, etc.], lower alkoxy(lower)alkylcarbamoyl-ar(lower)alkenoyl [e.g. methoxymethylcarbamoylcinnamoyl, methoxyethylcarbamoylcinnamoyl, bis(methoxyethyl)carbamoylcinnamoyl, ethoxyethylcarbamoylcinnamoyl, methoxypropylcarbamoylcinnamoyl, bis(ethoxyethyl)carbamoylcinnamoyl, etc.], N-[lower alkoxy(lower)alkyl]-N-(lower alkyl)carbamoyl-ar(lower)alkenoyl [e.g. N-methoxyethyl-N-methylcarbamoylcinnamoyl, N-ethoxyethyl-N-methylcarbamoylcinnamoyl, etc.], heterocyclic(lower)alkylcarbamoyl-ar(lower)alkenoyl [e.g. pyridylmethylcarbamoylcinnamoyl, furylmethylcarbamoylcinnamoyl, thienylmethylcarbamoylcinnamoyl, etc.], N-[heterocyclic(lower)alkyl]-N-(lower alkyl)carbamoyl-ar(lower)alkenoyl [e.g. N-pyridylmethyl-N-methylcarbamoylcinnamoyl, etc.], heterocycliccarbamoyl-ar(lower)alkenoyl [e.g. morpholinylcarbamoylcinnamoyl, thienylcarbamoylcinnamoyl, pyridylcarbamoylcinnamoyl, pyrimidinylcarbamoylcinnamoyl, tetrazolylcarbamoylcinnamoyl, etc.], optionally substituted heterocycliccarbonyl-ar(lower)alkenoyl [e.g. morpholinocarbonylcinnamoyl, pyrrolidinylcarbonylcinnamoyl, piperidinocarbonylcinnamoyl, tetrahydropyridylcarbonylcinnamoyl, methylpiperazinylcarbonylcinnamoyl, etc.], lower alkenylcarbamoyl-ar(lower)alkenoyl [e.g. vinylcarbamoylcinnamoyl, allylcarbamoylcinnamoyl, methylpropenylcarbamoylcinnamoyl, etc.], lower alkynylcarbamoyl-ar(lower)alkenoyl [e.g. ethynylcarbamoylcinnamoyl, propynylcarbamoylcinnamoyl, etc.], amino(lower)alkylcarbamoyl-ar(lower)alkenoyl [e.g. aminomethylcarbamoylcinnamoyl, aminoethylcarbamoylcinnamoyl, etc.], lower alkylamino(lower)alkylcarbamoyl-ar(lower)alkenoyl [e.g. methylaminomethylcarbamoylcinnamoyl, methylaminoethylcarbamoylcinnamoyl, ethylaminoethylcarbamoylcinnamoyl, dimethylaminoethylcarbamoylcinnamoyl, etc.], lower alkylcarbamoyloxy(lower)alkylcarbamoyl-ar(lower)alkenoyl [e.g. methylcarbamoyloxymethylcarbamoylcinnamoyl, methylcarbamoyloxyethylcarbamoylcinnamoyl, ethylcarbamoyloxyethylcarbamoylcinnamoyl, dimethylcarbamoyloxyethylcarbamoylcinnamoyl, etc.], lower alkylcarbamoyl(lower)alkylcarbamoyl-ar(lower)alkenoyl [e.g. methylcarbamoylmethylcarbamoylcinnamoyl, methylcarbamoylethylcarbamoylcinnamoyl, ethylcarbamoylethylcarbamoylcinnamoyl, dimethylcarbamoylethylcarbamoylcinnamoyl, etc.], lower alkoxycarbonyl(lower)alkylcarbamoyl-ar(lower)alkenoyl [e.g. methoxycarbonylmethylcarbamoylcinnamoyl, methoxycarbonylethylcarbamoylcinnamoyl, ethoxycarbonylmethylcarbamoylcinnamoyl, ethoxycarbonylethylcarbamoylcinnamoyl, etc.], carboxy(lower)alkylcarbamoyl-ar(lower)alkenoyl [e.g. carboxymethylcarbamoylcinnamoyl, carboxyethylcarbamoylcinnamoyl, etc.], [lower alkylcarbamoyl-ar(lower)alkyl]carbamoyl-ar(lower)alkenoyl [e.g. (methylcarbamoyl-phenethyl).carbamoylcinnamoyl, (ethylcarbamoyl-phenethyl)carbamoylcinnamoyl, etc.], [lower alkoxycarbonyl-ar(lower)alkyl]carbamoyl-ar(lower)alkenoyl [e.g. (methoxycarbonyl-phenethyl)carbamoylcinnamoyl, (ethoxycarbonyl-phenethyl)carbamoylcinnamoyl, etc.], [carboxy-ar(lower)alkyl]carbamoyl-ar(lower)alkenoyl [e.g. carboxy-phenethyl)carbamoylcinnamoyl, etc.], N-[lower alkylcarbamoyl(lower)alkyl]-N-(lower alkyl)carbamoyl-ar(lower)alkenoyl [e.g. N-(methylcarbamoylmethyl)-N-methylcarbamoylcinnamoyl, N-(methylcarbamoylethyl)-N-methylcarbamoylcinnamoyl, N-(ethylcarbamoylethyl)-N-methylcarbamoylcinnamoyl, N-(dimethylcarbamoylethyl)-N-methylcarbamoylcinnamoyl, etc.], N-[lower alkoxycarbonyl(lower)alkyl]-N-(lower alkyl)carbamoyl-ar(lower)alkenoyl [e.g. N-methoxycarbonylmethyl-N-methylcarbamoylcinnamoyl, N-methoxycarbonylethyl-N-methylcarbamoylcinnamoyl, N-ethoxycarbonylmethyl-N-methylcarbamoylcinnamoyl, N-ethoxycarbonylethyl-N-methylcarbamoylcinnamoyl, etc.], N-[carboxy(lower)alkyl]-N-(lower alkyl)carbamoyl-ar(lower)alkenoyl [e.g. N-carboxymethyl-N-methylcarbamoylcinnamoyl, N-carboxyethyl-N-methylcarbamoylcinnamoyl, etc.], arylcarbamoyl-ar(lower)alkenoyl [e.g. phenylcarbamoylcinnamoyl, naphthylcarbamoylcinnamoyl, etc.], etc., etc., ar(lower)alkynoyl [e.g. phenylpropioloyl, etc.], substituted or unsubstituted heterocyclic(lower)alkenoyl such as heterocyclic(lower)alkenoyl [e.g. morpholinylacryloyl, pyridylacryloyl, thienylacryloyl, etc.], heterocyclic(lower)alkenyl-heterocyclic(lower)alkenoyl [e.g. pyridylvinylpyridylacryloyl, etc.], amino-heterocyclic(lower)alkenoyl [e.g. aminopyridylacryloyl, etc.], lower alkylamino-heterocyclic(lower)alkenoyl [e.g. methylaminopyridylacryloyl, dimethylaminopyridylacryloyl, etc.], acylamino-heterocyclic(lower)alkenoyl, for example, lower alkanoylamino-heterocyclic(lower)alkenoyl [e.g. acetylaminopyridylacryloyl, propionylaminopyridylacryloyl, etc.], lower alkenoylamino-heterocyclic(lower)alkenoyl [e.g. acryloylaminopyridylacryloyl, crotonoylaminopyridylacryloyl, etc.], heterocyclic(lower)alkanoylamino-heterocyclic(lower)alkenoyl [e.g. pyridylacetylaminopyridylacryloyl, thienylacetylaminopyridylacryloyl, etc.], optionally substituted heterocycliccarbonylamino-heterocyclic(lower)alkenoyl [e.g. pyridylcarbonylaminopyridylacryloyl, furylcarbonylaminopyridylacryloyl, methylpyridylcarbonylaminopyridylacryloyl, etc.], lower alkanoylamino(lower)alkanoylamino-heterocyclic(lower)alkenoyl [e.g. acetylaminoacetylaminopyridylacryloyl, acetylaminopropionylaminopyridylacryloyl, etc.], lower alkoxycarbonyl(lower)alkanoylamino-heterocyclic(lower)alkenoyl [e.g. ethoxycarbonylacetylaminopyridylacryloyl, ethoxycarbonylpropionylaminopyridylacryloyl, etc.], lower alkoxy(lower)alkanoylamino-heterocyclic(lower)alkenoyl [e.g. methoxyacetylaminopyridylacryloyl, methoxypropionylaminopyridylacryloyl, ethoxypropionylaminopyridylacryloyl, etc.], etc., lower alkylureido-heterocyclic(lower)alkenoyl [e.g. methylureidopyridylacryloyl, etc.], acyl-heterocyclic(lower)alkenoyl, for example, carboxy-heterocyclic(lower)alkenoyl [e.g. carboxypyridylacryloyl, etc.], lower alkoxycarbonyl-heterocyclic(lower)alkenoyl [e.g. methoxycarbonylpyridylacryloyl, ethoxycarbonylpyridylacryloyl, etc.], carbamoyl-heterocyclic(lower)alkenoyl [e.g. carbamoylpyridylacryloyl, etc.], lower alkylcarbamoyl-heterocyclic(lower)alkenoyl [e.g.

methylcarbamoylpyridylacryloyl, ethylcarbamoylpyridylacryloyl, dimethylcarbamoylpyridylacryloyl, diethylcarbamoylpyridylacryloyl, isopropylcarbamoylpyridylacryloyl, N-ethyl-N-methylcarbamoylpyridylacryloyl, etc.], lower alkoxy(lower)alkylcarbamoyl-heterocyclic(lower)alkenoyl [e.g. methoxymethylcarbamoylpyridylacryloyl, methoxyethylcarbamoylpyridylacryloyl, methoxypropylcarbamoylpyridylacryloyl, ethoxyethylcarbamoylpyridylacryloyl, bis(methoxyethyl)carbamoylpyridylacryloyl, etc.], hydroxy(lower)alkylcarbamoyl-heterocyclic(lower)alkenoyl [e.g. hydroxymethylcarbamoylpyridylacryloyl, hydroxyethylcarbamoylpyridylacryloyl, bis(hydroxyethyl)carbamoylpyridylacryloyl, etc.], heterocycliccarbamoyl-heterocyclic(lower)alkenoyl [e.g. pyridylcarbamoylpyridylacryloyl, morpholinylcarbamoylpyridylacryloyl, thienylcarbamoylpyridylacryloyl, pyrimidinylcarbamoylpyridylacryloyl, etc.], heterocyclic(lower) alkylcarbamoyl-heterocyclic (lower)alkenoyl [e.g. pyridylmethylcarbamoylpyridylacryloyl, furylmethylcarbamoylpyridylacryloyl, thienylmethylcarbamoylpyridylacryloyl, etc.], heterocycliccarbonyl-heterocyclic(lower)alkenoyl (e.g. morpholinocarbonylpyridylacryloyl, pyrrolidinylcarbonylpyridylacryloyl, piperidinocarbonylpyridylacryloyl, etc.], lower alkenylcarbamoyl-heterocyclic (lower) alkenoyl [e.g. vinylcarbamoylpyridylacryloyl, allylcarbamoylpyridylacryloyl, etc.], lower alkynylcarbamoyl-heterocyclic(lower)alkenoyl [e.g. ethynylcarbamoylpyridylacryloyl, propynylcarbamoylpyridylacryloyl, etc.], etc., etc., heterocycliccarbonyl which may be substituted with substituent [e.g. furoyl, thenoyl, nicotinoyl, methylnicotinoyl, isonicotinoyl, morpholinocarbonyl, piperidinocarbonyl, 4-methyl-1-piperazinylcarbonyl, 4-ethyl-1-piperazinylcarbonyl, dimethylaminopiperidinocarbonyl, 4-methylcarbamoyl-1-piperazinylcarbonyl, 1,2,3,6-tetrahydropyridylcarbonyl, pyrrolidinylcarbonyl, indolylcarbonyl, etc.], aryloxycarbonyl which may be substituted with nitro [e.g. phenyloxycarbonyl, nitrophenyloxycarbonyl, etc.], ar(lower)alkoxycarbonyl which may be substituted with nitro [e.g. benzyloxycarbonyl, nitrobenzyloxycarbonyl, etc.], substituted or unsubstituted carbamoyl or thiocarbamoyl such as carbamoyl, lower alkylcarbamoyl [e.g. methylcarbamoyl, ethylcarbamoyl, propylcarbamoyl, isopropylcarbamoyl, butylcarbamoyl, isobutylcarbamoyl, tert-butylcarbamoyl, pentylcarbamoyl, dimethylcarbamoyl, diethylcarbamoyl, N-ethyl-N-methylcarbamoyl, etc.], carboxy(lower)alkylcarbamoyl [e.g. carboxymethylcarbamoyl, carboxyethylcarbamoyl, etc.], esterified carboxy(lower)alkylcarbamoyl, for example, lower alkoxycarbonyl(lower)alkylcarbamoyl [e.g. methoxycarbonylmethylcarbamoyl, ethoxycarbonylmethylcarbamoyl, ethoxycarbonylethylcarbamoyl, etc.], lower alkenylcarbamoyl [e.g. vinylcarbamoyl, allylcarbamoyl, etc.], cyclo(lower) alkylcarbamoyl [e.g. cyclopropylcarbamoyl, cyclobutylcarbamoyl, cyclopentylcarbamoyl, cyclohexylcarbamoyl, etc.], halo(lower)alkanoylcarbamoyl [e.g. trichloroacetylcarbamoyl, etc.], substituted or unsubstituted arylcarbamoyl, for example, arylcarbamoyl [e.g. phenylcarbamoyl, tolylcarbamoyl, xylylcarbamoyl, naphthylcarbamoyl, ethylphenylcarbamoyl, etc.], arylthiocarbamoyl [e.g. phenylthiocarbamoyl, etc.], lower alkoxy-arylcarbamoyl [e.g. methoxyphenylcarbamoyl, etc.], halo-arylcarbamoyl [e.g. fluorophenylcarbamoyl, chlorophenylcarbamoyl, etc.], halo(lower)alkylarylcarbamoyl [e.g. trifluoromethylphenylcarbamoyl, etc.], nitro-arylcarbamoyl [e.g. nitrophenylcarbamoyl, etc.], cyano-arylcarbamoyl [e.g. cyanophenylcarbamoyl, etc.), hydroxy(lower)alkyl-arylcarbamoyl (e.g. hydroxymethylphenylcarbamoyl, hydroxyethylphenylcarbamoyl, etc.), amino-arylcarbamoyl [e.g. aminophenylcarbamoyl, etc.], lower alkylamino-arylcarbamoyl [e.g. methylaminophenylcarbamoyl, ethylaminophenylcarbamoyl, dimethylaminophenylcarbamoyl, etc.], lower alkanoylaminoarylcarbamoyl [e.g. acetylaminophenylcarbamoyl, propionylaminophenylcarbamoyl, etc.], N-(lower alkanoyl)-N-(lower alkyl)amino-arylcarbamoyl [e.g. N-acetyl-N-methylaminophenylcarbamoyl, N-propionyl-N-methylaminophenylcarbamoyl, etc.), lower alkoxy(lower)alkanoylamino-arylcarbamoyl [e.g. methoxyacetylaminophenylcarbamoyl, methoxypropionylaminophenylcarbamoyl, etc.], lower alkoxycarbonyl(lower)alkanoylamino-arylcarbamoyl [e.g. ethoxycarbonylacetylaminophenylcarbamoyl, methoxycarbonylpropionylaminophenylcarbamoyl, etc.], carboxyamino-arylcarbamoyl [e.g. carboxyaminophenylcarbamoyl, etc.], lower alkoxycarbonylamino-arylcarbamoyl [e.g. ethoxycarbonylaminophenylcarbamoyl, etc.], aroylaminoarylcarbamoyl [e.g. benzoylaminophenylcarbamoyl, etc.], heterocycliccarbonylamino-arylcarbamoyl [e.g. pyridylcarbonylaminophenylcarbamoyl, furylcarbonylaminophenylcarbamoyl, morpholinocarbonylaminophenylcarbamoyl, etc.], heterocyclic(lower)alkanoylamino-arylcarbamoyl [e.g. pyridylacetylaminophenylcarbamoyl, thienylacetylaminophenylcarbamoyl, etc.], ureido-arylcarbamoyl [e.g. ureidophenylcarbamoyl, etc.], lower alkylureido-arylcarbamoyl [e.g. methylureidophenylcarbamoyl, ethylureidophenylcarbamoyl, etc.], hydroxyimino(lower)alkyl-arylcarbamoyl [e.g. hydroxyiminoethylphenylcarbamoyl, etc.], lower alkoxyimino(lower)alkyl-arylcarbamoyl [e.g. methoxyiminoethylphenylcarbamoyl, etc.], lower alkylhydrazono(lower)alkyl-arylcarbamoyl [e.g. methylhydrazonoethylphenylcarbamoyl, dimethylhydrazonoethylphenylcarbamoyl, etc.], optionally substituted heterocyclic-arylcarbamoyl [e.g. oxopyrrolidinylphenylcarbamoyl, oxopiperidinophenylcarbamoyl, dioxopyrrolidinylphenylcarbamoyl, oxooxazolidinylphenylcarbamoyl, pyrrolylphenylcarbamoyl, etc.], acyl-arylcarbamoyl, for example, carboxy-arylcarbamoyl [e.g. carboxyphenylcarbamoyl, etc.], lower alkoxycarbonyl-arylcarbamoyl [e.g. ethoxycarbonylphenylcarbamoyl, etc.], heterocycliccarbonyl-arylcarbamoyl [e.g. morpholinocarbonylphenylcarbamoyl, pyrrolidinylcarbonylphenylcarbamoyl, piperidinocarbonylphenylcarbamoyl, 1,2,3,6-tetrahydropyridylcarbonylphenylcarbamoyl, piperazinylcarbonylphenylcarbamoyl, thiomorpholinocarbonylphenylcarbamoyl, etc.], heterocycliccarbonyl-arylcarbamoyl substituted with lower alkyl [e.g. methylpiperazinylcarbonylphenylcarbamoyl, ethylpiperazinylcarbonylphenylcarbamoyl, etc.], heterocycliccarbonyl-arylcarbamoyl substituted with aryl [e.g. phenylpiperazinylcarbonylphenylcarbamoyl, etc.], heterocycliccarbonyl-arylcarbamoyl substituted with a heterocyclic group (e.g. pyridylpiperazinylcarbonylphenylcarbamoyl, etc.], heterocycliccarbonyl-arylcarbamoyl substituted with lower alkanoyl [e.g. acetylpiperazinylcarbonylphenylcarbamoyl, etc.], heterocycliccarbonylarylcarbamoyl substituted with lower alkoxycarbonyl [e.g. ethoxycarbonylpiperazinylcarbonylphenylcarbamoyl, etc.], heterocycliccarbonyl-arylcarbamoyl substituted with lower alkylamino [e.g. methylaminopiperazinylcarbonylphenylcarbamoyl, dimethylaminopiperidinocarbonylphenylcarbamoyl, etc.], heterocycliccarbonyl-arylcarbamoyl substituted with lower alkylcarbamoyl [e.g. methylcarbamoylpiperazinylcarbonylphenylcarbamoyl, etc.], carbamoyl-arylcarbamoyl [e.g. carbamoylphenylcarbamoyl, etc.], lower alkylcarbamoyl-arylcarbamoyl [e.g. methylcarbamoylphenylcarbamoyl, ethylcarbamoylphenylcarbamoyl, propylcarbamoylphenylcarbamoyl, dimethylcarbamoylphenylcarbamoyl, diethylcarbamoylphenylcarbamoyl, N-ethyl-N-methylcarbamoylphenylcarbamoyl, N-isopropyl-N-methylcarbamoylphenylcarbamoyl, etc.], hydroxy(lower) alkylcarbamoyl-arylcarbamoyl [e.g. hydroxymethylcarbamoylphenylcarbamoyl, hydroxyethylcarbamoylphenylcarbamoyl, bis(hydroxyethyl)carbamoylphenylcarbamoyl, etc.], N-[hydroxy(lower)alkyl]-N-(lower alkyl)carbamoyl-arylcarbamoyl [e.g. N-(hydroxyethyl)-N-methylcarbamoylphenylcarbamoyl, etc.], lower alkoxy (lower)alkylcarbamoyl-arylcarbamoyl [e.g. methoxymethylcarbamoylphenylcarbamoyl, methoxyethylcarbamoylphenylcarbamoyl, ethoxyethylcarbamoylphenylcarbamoyl, bis(methoxyethyl) carbamoylphenylcarbamoyl, bis(ethoxyethyl)carbamoylphenylcarbamoyl, etc.], N-[lower alkoxy(lower)alkyl]-N-(lower alkyl)carbamoyl-arylcarbamoyl [e.g. N-(methoxyethyl)-N-methylcarbamoylphenylcarbamoyl, N-(methoxypropyl)-N-methylcarbamoylphenylcarbamoyl, etc.], lower alkylamino(lower)alkylcarbamoyl-arylcarbamoyl [e.g. methylaminoethylcarbamoylphenylcarbamoyl, dimethylaminoethylcarbamoylphenylcarbamoyl, etc.], N-[lower alkylamino(lower)alkyl]-N-(lower alkyl) carbamoylarylcarbamoyl [e.g. N-(dimethylaminoethyl)-N-methyl-carbamoylphenylcarbamoyl, N-(dimethylaminopropyl)-N-methylcarbamoylphenylcarbamoyl, etc.], heterocycliccarbamoyl-arylcarbamoyl [e.g. morpholinylcarbamoylphenylcarbamoyl, thienylcarbamoylphenylcarbamoyl, pyridylcarbamoylphenylcarbamoyl, pyrimidinylcarbamoylphenylcarbamoyl, etc.], N-(heterocyclic)-N-(lower alkyl)carbamoyl-arylcarbamoyl [e.g. N-pyridyl-N-methylcarbamoylphenylcarbamoyl, etc.], heterocyclic(lower)alkylcarbamoyl-arylcarbamoyl [e.g. pyridylmethylcarbamoylphenylcarbamoyl, pyridylethylcarbamoylphenylcarbamoyl, thienylmethylcarbamoylphenylcarbamoyl, etc.], N-[heterocyclic(lower)alkyl]-N-(lower alkyl)carbamoyl-arylcarbamoyl [e.g. N-pyridylmethyl-N-methylcarbamoylphenylcarbamoyl, etc.], N-[heterocyclic (lower)alkyl]-N-[lower alkoxy(lower)alkyl]carbamoyl-arylcarbamoyl [e.g. N-pyridylmethyl-N-methoxyethylcarbamoylphenylcarbamoyl, etc.] arylcarbamoyl-arylcarbamoyl [e.g. phenylcarbamoylphenylcarbamoyl, etc.], lower alkylaminoarylcarbamoyl-arylcarbamoyl [e.g. dimethylaminophenylcarbamoylphenylcarbamoyl, etc.], lower alkanoyl-arylcarbamoyl [e.g. acetylphenylcarbamoyl, propionylphenylcarbamoyl, etc.], etc., etc., ar(lower) alkylcarbamoyl [e.g. benzylcarbamoyl, phenethylcarbamoyl, etc.], heterocycliccarbamoyl [e.g. furylcarbamoyl, thienylcarbamoyl, pyridylcarbamoyl, quinolylcarbamoyl, isoquinolylcarbamoyl, pyrimidinylcarbamoyl, pyrazolylcarbamoyl, etc.], heterocyclic(lower)alkylcarbamoyl (e.g. pyridylmethylcarbamoyl, pyridylethylcarbamoyl, furylmethylcarbamoyl, thienylmethylcarbamoyl, etc.], arylaminocarbamoyl [e.g. phenylaminocarbamoyl, etc.], aroylcarbamoyl [e.g. benzoylcarbamoyl, etc.], etc., lower alkylsulfonyl [e.g. mesyl, ethylsulfonyl, propylsulfonyl, isopropylsulfonyl, tert-butylsulfonyl, pentylsulfonyl, etc.], arylsulfonyl [e.g. tosyl, phenylsulfonyl, etc.], ar(lower) alkylsulfonyl [e.g. benzylsulfonyl, phenethylsulfonyl, etc.], ar(lower)alkenylsulfonyl [e.g. styrylsulfonyl, cinnamylsulfonyl, etc.], phthaloyl, or the like.

More preferred examples of the above-mentioned acyl group may be a group of the formula:

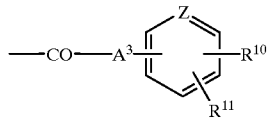

wherein $R^{10}$ is carboxy, esterified carboxy, heterocyclic(lower) alkenyl or a group of the formula:

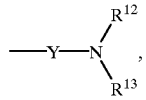

in which Y is a single bond or —CO—, and $R^{12}$ and $R^{13}$ are each ad defined above, and $R^{11}$, $A^3$ and Z are each as defined above.

Suitable "lower alkanoyl" may be formyl, acetyl, propionyl, butyryl, isobutyryl, valeryl, isovaleryl, pivaloyl, hexanoyl, 3,3-dimethylbutyryl, or the like.

Suitable "lower alkoxy(lower)alkanoyl" may be methoxyacetyl, ethoxyacetyl, methoxypropionyl, ethoxypropionyl, propoxypropionyl, methoxybutyryl, or the like.

Suitable lower alkenyl moiety in the term "heterocyclic (lower)alkenyl" may be a straight or branched $C_2$–$C_6$ alkenyl such as vinyl, allyl, 1-propenyl, isopropenyl, butenyl, isobutenyl, pentenyl, hexenyl or the like.

Suitable "heterocyclic group" formed by $R^{12}$, $R^{13}$ and the attached nitrogen atom may be morpholino, thiomorpholino, pyrrolidin-1-yl, piperidino, 1,2,3,6-tetrahydropyridin-1-yl, piperazin-1-yl, or the like.

Suitable "lower alkenylene" may be a straight or branched $C_2$–$C_6$ alkenylene such as vinylene, methylvinylene, propenylene, 1,3-butadienylene or the like, in which the most preferable one is vinylene.

Suitable aryl moiety in the various definitions mentioned in this specification and claims such as in the terms "ar (lower)alkenoyl", "arylcarbamoyl", "ar(lower)alkyl", etc., may be phenyl, naphthyl, phenyl substituted with lower alkyl [e.g. tolyl, xylyl, mesityl, cumenyl, di(tert-butyl) phenyl, etc.] and the like, in which preferable one is phenyl, naphthyl and tolyl.

Suitable "heterocyclic group" and all heterocyclic moieties in the various definitions mentioned in this specification and claims such as in the terms "heterocycliccarbonyl", "heterocyclic(lower)alkyl", "heterocyclic(lower)alkenyl", "heterocyclic(lower)alkenoyl", etc., may include saturated or unsaturated, monocyclic or polycyclic one containing at least one hetero atom such as nitrogen atom, oxygen atom or sulfur atom, preferably N, O and/or S containing 5 or 6-membered heterocyclic group, in which preferable ones may be morpholinyl, piperazinyl, pyridyl, tetrahydropyridyl, pyrimidinyl, piperidyl, thienyl, furyl, oxazolyl, isoxazolyl, thiazolyl, tetrazolyl, imidazolyl, pyrrolidinyl, pyrrolyl, pyrazolyl, or the like.

Suitable "esterified carboxy" may be lower alkoxycarbonyl [e.g. methoxycarbonyl, ethoxycarbonyl, tert-butoxycarbonyl, etc.), ar(lower)alkoxycarbonyl [e.g. benzyloxycarbonyl, etc.], or the like.

Suitable "a leaving group" may be a conventional acid residue such as halogen (e.g. fluoro, chloro, bromo and iodo], arenesulfonyloxy [e.g. benzenesulfonyloxy, tosyloxy, etc.], alkanesulfonyloxy [e.g. mesyloxy, ethanesulfonyloxy, etc.], and the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid addition salt [e.g. formate, acetate, trifluoroacetate, maleate, tartrate, oxalate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. arginine salt, aspartic acid salt, glutamic acid salt, etc.], an intramolecular salt and the like.

With respect to the salts of the compounds [Ia] to [Ie] in the Processes 2 to 4, it is to be noted that these compounds are included within the scope of the compound [I], and accordingly the suitable examples of the salts of these compounds are to be referred to those as exemplified for the object compound [I].

Preferred embodiments of the object compound [I] are as follows:

a) A compound of the formula:

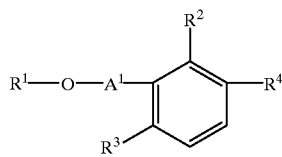

[I]

wherein

A$^1$ is lower alkylene, most preferably methylene,

R$^1$ is quinolyl, quinazolinyl, quinoxalinyl, benzimidazolyl, benzofuryl, benzoxazolyl or imidazopyridyl, each of which is substituted with substituent(s) selected from the group consisting of halogen, lower alkyl, lower alkoxy, lower alkylamino and a heterocyclic group, [more preferably, 2-(lower alkyl)-quinolin-8-yl, 4-(lower alkoxy)-2-(lower alkyl)-quinolin-8-yl, 4-(lower alkylamino)-2-(lower alkyl)-quinolin-8-yl, 4-(morpholino)-2-(lower alkyl)-quinolin-8-yl, 4-(imidazolyl)-2-(lower alkyl)-quinolin-8-yl, 4-(pyrazolyl)-2-(lower alkyl)-quinolin-8-yl, 2-(lower alkyl)-quinazolin-8-yl, 2-(lower alkyl)-quinoxalin-8-yl, 2-(lower alkoxy)-1-(lower alkyl)-1H-benzimidazol-4-yl, 1-(lower alkyl)-2-(lower alkyl)-1H-benzimidazol-4-yl, 2-(lower alkyl)-3-(lower alkyl)-benzofuran-7-yl, 2-(lower alkyl)-benzoxazol-4-yl or 2-(lower alkyl)-3-(halo)-imidazo[1,2-a]pyridin-8-yl], R$^2$ is hydrogen, halogen or lower alkyl, R$^3$ is halogen or lower alkyl, and R$^4$ is carboxy, lower alkanoyl or a group of the formula:

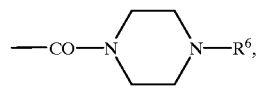

[more preferably —Q—A$^2$—R$^5$], in which

R$^5$ is amino, acylamino, cyano, hydroxy, hydroxyimino (lower)alkyl or acyl, [more preferably, amino or a group of the formula:

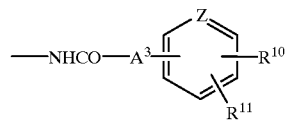

wherein

R$^{10}$ is carboxy, esterified carboxy, heterocyclic (lower)alkenyl or a group of the formula:

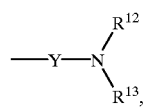

in which

R$^{12}$ is hydrogen, lower alkyl, heterocyclic(lower) alkyl, a heterocyclic group, lower alkanoyl, lower alkoxy(lower)alkanoyl, heterocycliccarbonyl optionally substituted with lower alkyl, or lower alkylsulfonyl, and R$^{13}$ is hydrogen, lower alkyl or heterocyclic (lower)alkyl, or R$^{12}$ and R$^{13}$ are taken together with the attached nitrogen atom to form a heterocyclic group optionally substituted with oxo, and Y is a single bond or —CO—, R$^{11}$ is hydrogen, lower alkyl or lower alkoxy, A$^3$ is —NH—, lower alkylene or lower alkenylene, and Z is CH or N], R$^6$ is hydrogen or acyl, A$^2$ is lower alkylene or a single bond, and Q is lower alkenylene or a group of the formula:

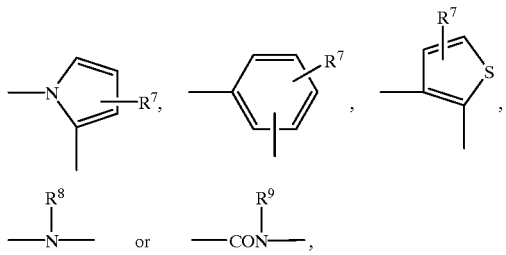

[more preferably, a group of the formula:

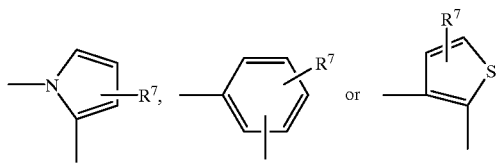

and most preferably a group of the formula:

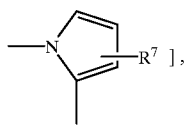

in which
$R^7$ is hydrogen or halogen;
$R^8$ is hydrogen, or
$R^8$ and $R^2$ are taken together to form lower alkylene; and
$R^9$ is hydrogen, lower alkyl or ar(lower)alkyl; and
b) A compound of the formula:

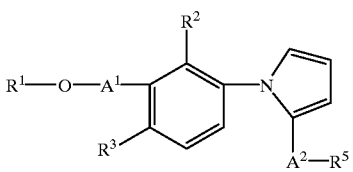

[I']

wherein
$R^1$ is quinolyl, quinazolinyl, quinoxalinyl, benzimidazolyl, benzofuryl, benzoxazolyl or imidazopyridyl, each of which is substituted with substituent(s) selected from the group consisting of halogen, lower alkyl, lower alkoxy and lower alkylamino,
$R^2$ is hydrogen, halogen or lower alkyl,
$R^3$ is halogen or lower alkyl,
$R^5$ is amino or acylamino, and
$A^1$ and $A^2$ are each lower alkylene.

The processes for preparing the object compound [I] are explained in detail in the following.

Process 1

The object compound [I] or its salt can be prepared by reacting a compound [II] or its salt with a compound [III] or its salt.

Suitable salts of the compounds [II] and [III] may be the same as those exemplified for the compound [I].

The reaction is preferably carried out in the presence of a base such as alkali metal [e.g. lithium, sodium, potassium, etc.], the hydroxide or carbonate or bicarbonate thereof (e.g. sodium hydroxide, potassium carbonate, potassium bicarbonate, etc.], alkali metal alkoxide [e.g. sodium methoxide, sodium ethoxide, potassium tert-butoxide, etc.], or the like.

This reaction is usually carried out in a conventional solvent such as tetrahydrofuran, dioxane, N,N-dimethylformamide, acetone, or the like.

The reaction temperature is not critical, and the reaction is usually carried out under cooling to heating.

Process 2

The object compound [Ib] or its salt can be prepared by acylating a compound [Ia] or its salt.

The acylation is carried out in the presence of an acylating agent.

Suitable acylating agents are the corresponding carboxylic acid or sulfonic acid compounds, which are represented by the formula: R—OH wherein R is acyl, and reactive derivatives thereof, and the corresponding isocyanate or isothiocyanate compounds.

As suitable said reactive derivatives, there may be mentioned acid halides, acid anhydrides, active amides and active esters. Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and active esters such as p-nitrophenyl ester and N-hydroxysuccinimide ester. The kind of such reactive derivatives can be selected depending on the kind of acyl group to be introduced.

The reaction is usually carried out in a conventional solvent, such as methylene chloride, chloroform, pyridine, dioxane, tetrahydrofuran, N,N-dimethylformamide, or the like. In case that the acylating agent is liquid, it can also be used as a solvent. In case that the carboxylic acid or sulfonic acid compounds are used as acylating agent in the free acid form or salt form, it is preferable to carry out the reaction in the presence of a conventional condensing agent such as 1-ethyl-3-(3-dimethylaminopropyl)carbodiimide, N,N'-dicyclohexylcarbodiimide or the like.

The reaction temperature is not critical and the reaction can be carried out under cooling, at ambient temperature, or under heating.

This reaction is preferably carried out in the presence of a conventional inorganic base or in the presence of a conventional organic base.

Process 3

The object compound [Id] or its salt can be prepared by subjecting a compound [Ic] or its salt to deesterification reaction.

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g., sodium, potassium, etc.], the hydroxide or carbonate or bicarbonate thereof, triethylamine, or the like.

Suitable acid may include an organic acid [e.g. acetic-acid, trifluoroacetic acid, etc.] and an inorganic acid [e.g. hydrochloric acid, hydrobromic acid, hydrogen chloride, hydrogen bromide, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent.

The reaction temperature is not critical and the reaction is usually carried out under cooling to warming.

The reduction method applicable for the elimination reaction may include catalytic reduction.

Suitable catalysts to be used in catalytic reduction are conventional ones such as platinum catalysts [e.g. platinum plate, platinum oxide, etc.], palladium catalysts [e.g., palladium black, palladium oxide, palladium on carbon, etc.], and the like.

The reduction is usually carried out in a conventional solvent which does not adversely influence the reaction such as methanol, ethanol, propanol, N,N-dimethylformamide, or a mixture thereof.

The reaction temperature of this reduction is not critical and the reaction is usually carried out under cooling to warming.

Process 4

The object compound [Ie] or its salt can be prepared by reacting a compound [Id] or its reactive derivative at the carboxy group or a salt thereof with a compound [IV] or its salt.

Suitable reactive derivative at the carboxy group of the compound [Id] may include an acid halide, an acid anhydride, an activated amide, an activated ester, and the like. Suitable examples of the reactive derivatives may be an acid chloride; an acid azide; a mixed acid anhydride with an acid such as dialkylphosphoric acid, sulfuric acid aliphatic carboxylic acid or aromatic carboxylic acid; a symmetrical acid anhydride; an activated amide with imidazole; or an activated ester [e.g. p-nitrophenyl ester, etc.]. These ractive derivatives can optionally be selected from them according to the kind of the compound [Id] to be used.

Suitable salts of the compound [IV] can be referred to the organic or inorganic acid addition salts as exemplified for the compound [I].

This reaction can be carried out in substantially the same manner as Process 2, and therefore the reaction mode and reaction condition of this reaction are to be referred to those explained in Process 2.

The object compound [I] and the starting compounds can also be prepared by the methods of Examples and Preparations mentioned below or similar manners thereto or conventional manners.

The compounds obtained by the above processes can be isolated and purified by a conventional method such as pulverization, recrystallization, chromatography, reprecipitation or the like.

It is to be noted that the compound [I] and the other compounds may include one or more stereoisomers and geometrical isomers due to asymmetric carbon atoms and double bonds, and all of such isomers and mixture thereof are included within the scop of this invention.

The compound of the formula [I] and its salt can be in the form of a solvate, which is included within the scope of the present invention. The solvate preferably includes a hydrate and an ethanolate.

The object compound [I] and pharmaceutically acceptable salts thereof possess strong activities as bradykinin antagonists, and are useful for the treatment and/or the prevention of bradykinin or its analogues mediated diseases such as allergy, inflammation, autoimmune disease, shock, pain, or the like, and more particularly for the prevention and/or the treatment of asthma, cough, bronchitis, rhinitis, rhinorrhea, obstructive pulmonary disease [e.g. pulmonary emphysema, etc.], expectoration, pneumonitis, systemic inflammatory response syndrome (SIRS), septic shock, endotoxin shock, anaphylactic shock, adult respiratory distress syndrome, disseminated intravascular coagulopathy, arthritis, rheumatism, osteoarthritis, lumbago, inflammation-induced bone resorption, conjunctivitis, vernal conjunctivitis, uveitis, iritis, iridocyclitis, headache, migraine, toothache, backache, superficial pain, cancerous pain, postoperative pain, tenalgia, trauma [e.g. wound, burn, etc.], rash, erythema, eczema or dermatitis [e.g. contact dermatitis, atopic dermatitis, etc.], urticaria, herpes, itching, psoriasis, lichen, inflammatory bowel disease [e.g. ulcerative colitis, Crohn's disease, etc.], diarrhea, emesis, hepatitis, pancreatitis, gastritis, esophagitis, food allergy, ulcer, irritable bowel syndrome, nephritis, angina, periodontitis, edema, hereditary angioneurotic edema, cerebral edema (traumatic cerebral edema), cerebral infarction, low blood pressure, thrombosis, myocardial infarction, cerebral vasospasm, congestion, coagulation, gout, central nervous system injury, premature labor, arteriosclerosis (hyperlipidemia, hypercholesterolemia), postgastrectomy dumping syndrome, carcinoid syndrome, altered sperm mobility, diabetic neuropathy, neuralgia, graft rejection in transplantation, or the like, in human being or animals.

And further, it is known that bradykinin relates to the release of mediators such as prostaglandins, leukotrienes, tachykinins, histamine, thromboxanes, or the like, so the compound [I] is expected to be useful for the prevention and/or the treatment of such mediators mediated diseases.

In order to illustrate the usefulness of the object compound [I], the pharmacological test data of some representative compounds of the compound [I] are shown in the following.

$^3$H-Bradykinin receptor binding (i) Test Method:

(a) Crude ileum membrane preparation

Male Hartly strain guinea pigs were sacrificed by decapitation. The ileum was removed and homogenized in buffer (50 mM trimethylaminoethanesulfonic acid (TES), 1 mM 1,10-phenanthroline pH 6.8). The homogenate was centrifuged (1000×g, 20 minutes) to remove tissue clumps and the supernatant was centrifuges (100,000×g, 60 minutes) to yield a pellet. The pellet was resuspended in buffer (50 mM TES, 1 mM 1,10-phenanthroline, 140 mg/l bacitracin, 1 mM dithiothreiol, 0.1% bovine serum albumin pH 6.8) and homogenized with a glass-teflon homogenizer to yield suspension which was referred to as crude membrane suspension. The obtained membrane suspension was stored at −80° C. until use.

(b) $^3$H-Bradykinin binding to the membrane

The frozen crude membrane suspension was thawed. In binding assays, $^3$H-Bradykinin (0.06 nM) and the test compound were incubated with 50 μl of the membrane suspension at room temperature for 60 minutes in a final volume of 250 μl. Separation of receptor-bound from free $^3$H-Bradykinin is achieved by immediate filtration under vacuum and washed three times with 5 ml of ice-cold buffer (50 mM Tris-HCl pH 7.5). Non-specific binding was defined as binding in the presence of 0.1 μM Bradykinin. The radioactivity retained on rinsed filters was determined by a liquid-scintillation counter.

(ii) Test Results:

| Test Compound (Example No.) | Inhibition of $^3$H-Bradykinin binding IC$_{50}$ (M) |
|---|---|
| 15 (trihydrochloride) | $2.6 \times 10^{-9}$ |
| 16-(1) | $3.3 \times 10^{-9}$ |
| 23-(3) (trihydrochloride) | $4.3 \times 10^{-9}$ |
| 33 (dihydrochloride) | $3.2 \times 10^{-9}$ |
| 40-(6) | $2.3 \times 10^{-9}$ |
| 45-(6) (hydrochloride) | $2.8 \times 10^{-9}$ |
| 50-(1) (hydrochloride) | $7.4 \times 10^{-9}$ |

The effects of the compound [I] on bradykinin-induced bronchoconstriction and carrageenin-induced paw edema were measured according to similar manners described in British Journal of Pharmacology, 102, 774–777 (1991).

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral such as intravenous, intramuscular, subcutaneous or intraarticular, external such as topical, enteral, intrarectal, transvaginal, inhalant, ophthalmic, nasal of hypoglossal administration. The pharmaceutical preparations may be capsules, tablets, dragees, granules, suppositories, solution, lotion, suspension, emulsion, ointment, gel, cream, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for preventing and/or treating the above-mentioned diseases. In general, amounts between 0.1 mg/body and about 1,000 mg/body may be administered per day.

EXAMPLES

The following Preparations and Examples are given for the purpose of illustrating this invention.

to be continued on the next page

Preparation 1

(1) A mixture of methyl 4-carboxycinnamate (1.5 g) and 10% palladium on carbon (300 mg) in methanol (5 ml) was stirred for 2 hours at ambient temperature under hydrogen atmosphere. Insoluble material was filtered off, and the filtrate was concentrated in vacuo to give 4-[2-(methoxycarbonyl)ethyl]benzoic acid (1.3 g).

NMR (DMSO-d$_6$, δ): 2.67 (2H, t, J=7.5 Hz), 2.93 (2H, t, J=7.5 Hz), 3.59 (3H, s), 7.35 (1H, d, J=8 Hz), 7.85 (1H, d, J=8 Hz).

(2) To a solution of 4-[2-(methoxycarbonyl)ethyl]benzoic acid (200 mg) in N,N-dimethylformamide were added 1-ethyl-3-(3-dimethylaminopropyl)carbodiimide hydrochloride (221 mg), 1-hydroxybenzotriazole (169 mg) and 2-aminomethylpyridine (114 mg) in water bath, and the mixture was stirred for 24 hours at ambient temperature. The mixture was poured into water and extracted with ethyl acetate. The organic layer was washed with water, saturated sodium bicarbonate solution and brine, dried over magnesium sulfate and concentrated in vacuo. The residue was purified by a preparative thin layer chromatography (dichloromethane:methanol=10:1, V/V) to give methyl 3-[4-(2-pyridylmethylcarbamoyl)phenyl]propionate (218 mg).

NMR (CDCl$_3$, δ): 2.65 (2H, t, J=7.5 Hz), 3.00 (2H, t, J=7.5 Hz), 3.67 (3H, s), 4.76 (2H, d, J=5 Hz), 7.22 (1H, dd, J=5, 8 Hz), 7.25–7.36 (3H, m), 7.55 (1H, br peak), 7.68 (1H, td, J=8, 2 Hz), 7.80 (2H, d, J=8 Hz), 8.57 (1H, d, J=5 Hz).

(3) To a solution of methyl 3-[4-(2-pyridylmethylcarbamoyl)phenyl]propionate (212 mg) in methanol was added 1N sodium hydroxide solution (1 ml), and the mixture was stirred for 5 hours at 50° C. The mixture was concentrated in vacuo, and the residue was dissolved in water and was adjusted to pH 6 with 1N hydrochloric acid. The resulting precipitate was collected by filtration to give 3-[4-(2-pyridylmethylcarbamoyl)phenyl]propionic acid (162 mg).

mp: 83.8° C.; NMR (DMSO-d$_6$, δ): 2.57 (2H, t, J=7.5 Hz), 2.88 (2H, t, J=7.5 Hz), 4.56 (2H, d, J=5 Hz), 7.25 (1H, dd, J=5, 8 Hz), 7.28–7.37 (3H, m), 7.74 (1H, td, J=8, 2 Hz), 7.83 (2H, d, J=8 Hz), 8.50 (1H, d, J=5 Hz), 9.05 (1H, t, J=5 Hz).

Preparation 2

(1) Methyl 4-(2-pyridylmethylcarbamoyl)cinnamate was obtained from methyl 4-carboxycinnamate and 2-aminomethylpyridine according to a similar manner to that of Preparation 1-(2).

NMR (CDCl$_3$, δ): 3.82 (3H, s), 4.77 (2H, d, J=5 Hz), 6.50 (1H, d, J=16 Hz), 7.23 (1H, dd, J=6, 8 Hz), 7.33 (1H, d, J=8 Hz), 7.56–7.76 (5H, m), 7.90 (2H, d, J=8 Hz), 8.57 (1H, d, J=5 Hz).

(2) 4-(2-Pyridylmethylcarbamoyl)cinnamic acid was obtained according to a similar manner to that of Preparation 1-(3).

NMR (DMSO-d$_6$, δ): 4.57 (2H, d, J=6 Hz), 6.63 (1H, d, J=16 Hz), 7.26 (1H, dd, J=6, 8 Hz), 7.32 (1H, d, J=8 Hz), 7.63 (1H, d, J=16 Hz), 7.70–7.85 (3H, m), 7.95 (2H, d, J=8 Hz), 8.51 (1H, d, J=6 Hz), 9.19 (1H, t, J=6 Hz).

Preparation 3

(1) A mixture of 3-methoxy-4-nitrobenzyl alcohol (1.0 g) and 10% palladium on carbon (100 mg) in methanol was stirred for 2 hours under 3 atmospheric pressure of hydrogen. After filtration, the filtrate was concentrated in vacuo to give 4-amino-3-methoxybenzyl alcohol (910 mg) as an oil.

NMR (CDCl$_3$, δ): 3.77 (2H, br s), 3.84 (3H, s), 4.56 (2H, s), 6.66 (1H, d, J=8 Hz), 6.76 (1H, d, J=8 Hz), 6.81 (1H, s).

(2) To a solution of 4-amino-3-methoxybenzyl alcohol (900 mg) in methanol was added acetic anhydride (1.8 g) under ice cooling, and the mixture was stirred for 1 hour at the same temperature. After evaporation, the residue was dissolved in ethyl acetate, and the solution was washed with sodium bicarbonate solution, water and brine, dried over magnesium sulfate and concentrated in vacuo to give 4-acetamido-3-methoxybenzyl alcohol (840 mg) as solid.

mp: 104° C.; NMR (CDCl$_3$, δ): 1.69 (1H, t, J=5 Hz), 2.20 (3H, s), 3.90 (3H, s), 4.65 (2H, d, J=5 Hz), 6.88–6.97 (2H, m), 7.74 (1H, br s), 8.32 (1H, d, J=8 Hz).

(3) To a mixture of 4-acetamido-3-methoxybenzyl alcohol (800 mg), triethylamine (2.07 g), dimethylsulfoxide (5 ml) and dichloromethane (2.5 ml) was added portionwise sulfur trioxide pyridine complex (1.3 g) in water bath, and the mixture was stirred for 2 hours at the same temperature. The reaction mixture was poured into water, and extracted with dichloromethane. The organic layer was washed with water and brine, dried over magnesium sulfate and concentrated in vacuo to give 4-acetamido-3-methoxybenzaldehyde (653 mg).

mp: 145° C.; NMR (CDCl$_3$, δ): 2.25 (3H, s), 3.97 (3H, s), 7.41 (1H, d, J=2 Hz), 7.48 (1H, dd, J=2, 8 Hz), 7.99 (1H, br s), 8.59 (1H, d, J=8 Hz), 9.88 (1H, s).

(4) To a solution of 4-acetamido-3-methoxybenzaldehyde (388 mg) in tetrahydrofuran (10 ml) was added methyl (triphenylphosphoranylidene)acetate (739 mg), and the mixture was stirred for 2 hours at ambient temperature. The mixture was poured into water and extracted with ethyl acetate. The organic layer was washed with water and brine, dried over magnesium sulfate and concentrated in vacuo. The residue was purified by column chromatography on silica gel (chloroform:methanol=30:1, V/V) to give methyl 4-acetamido-3-methoxycinnamate (113 mg).

mp: 137° C.; NMR (CDCl$_3$, $\delta$): 2.21 (3H, s), 3.80 (3H, s), 3.93 (3H, s), 6.36 (1H, d, J=16 Hz), 7.01 (1H, s), 7.14 (1H, d, J=8 Hz), 7.63 (1H, d, J=16 Hz), 7.83 (1H, br s), 8.40 (1H, d, J=8 Hz).

(5) 4-Acetamido-3-methoxycinnamic acid was obtained according to a similar manner to that of Preparation 1-(3)

mp: 221.5–230° C.; NMR (DMSO-d$_6$, $\delta$): 2.10 (3H, s), 3.89 (3H, s), 6.52 (1H, d, J=16 Hz), 7.20 (1H, d, J=8 Hz), 7.38 (1H, s-like), 7.53 (1H, d, J=16 Hz), 8.07 (1H, d, J=8 Hz), 9.26 (1H, s).

Preparation 4

A mixture of 4-acetamido-3-methylbenzaldehyde (1.23 g), malonic acid (795 mg), pyridine (549 mg) and ethanol (1.7 ml) was refluxed for 3 hours under nitrogen atmosphere. To the mixture was added ethanol (1.7 ml), and the mixture was stirred for 30 minutes under ice-bath cooling. The resulting precipitate was collected by filtration and washed with ethanol to give 4-acetamido-3-methylcinnamic acid (1.08 g).

mp: 262–263° C. (dec.); NMR (DMSO-d$_6$, $\delta$): 2.09 (3H, s), 2.23 (3H, s), 6.43 (1H, d, J=16 Hz), 7.43–7.61 (4H), 9.33 (1H, s).

Preparation 5

(1) To a mixture of 3-benzyloxy-N-methyl-2-nitroaniline (453.3 mg), 80% methanol (6.8 ml), anhydrous ferric chloride (13.6 mg) and carbon (13.6 mg) was dropwise added hydrazine monohydrate (255.6 $\mu$l) at 70° C., and the mixture was stirred for 5 hours at the same temperature. Insoluble material was filtered off, and the filtrate was concentrated in vacuo. Ethyl acetate and saturated sodium bicarbonate solution were added to the residue, and the organic layer was washed with water and brine, dried over magnesium sulfate and concentrated in vacuo. The residue was purified by column chromatography on silica gel (ethyl acetate—n-hexane) to give 2-amino-3-benzyloxy-N-methylaniline (348.9 mg).

mp: 79–81° C.; NMR (CDCl$_3$, $\delta$): 2.87 (3H, s), 3.43 (3H, br s), 5.07 (2H, s), 6.40 (1H, d, J=7.5 Hz), 6.49 (1H, d, J=7.5 Hz), 6.80 (1H, t, J=7.5 Hz), 7.29–7.47 (5H, m).

(2) To a stirred solution of 2-amino-3-benzyloxy-N-methylaniline (318.5 mg) in acetic acid (3.2 ml) was added tetramethyl orthocarbonate (223.0 $\mu$l) at ambient temperature, and the reaction mixture was stirred for 4 hours. The reaction mixture was concentrated in vacuo, and to the residue were added ethyl acetate and a saturated sodium bicarbonate solution. The organic layer was washed with water and brine, dried over anhydrous magnesium sulfate, and concentrated in vacuo. The residue was triturated with n-hexane -diisopropyl ether to give 4-benzyloxy-2-methoxy-1-methyl-1H-benzimidazole (273.3 mg) as a pale brown solid.

mp: 98–102° C.; NMR (CDCl$_3$, $\delta$): 3.53 (3H, s), 4.22 (3H, s), 5.40 (2H, s), 6.63 (1H, d, J=7.5 Hz), 6.77 (1H, d, J=7.5 Hz), 6.99 (1H, t, J=7.5 Hz), 7.22–7.41 (3H, m), 7.45–7.52 (2H, m).

(3) A mixture of 4-benzyloxy-2-methoxy-1-methyl-1H-benzimidazole (254.8 mg) and 10% palladium on carbon (25 mg) in methanol (2.5 ml) was stirred for 7 hours at ambient temperature under hydrogen atmosphere. Insoluble material was filtered off, and the filtrate was concentrated in vacuo. The residue was purified by column chromatography on silica gel (ethyl acetate:n-hexane=3:1, V/V) to give 4-hydroxy-2-methoxy-1-methyl-1H-benzimidazole (58.7 mg).

mp: 226–229° C.; NMR (DMSO-d$_6$, $\delta$): 3.48 (3H, s), 4.08 (3H, s), 6.49 (1H, d, J=7.5 Hz), 6.76 (1H, d, J=7.5 Hz), 6.88 (1H, t, J=7.5 Hz), 9.39 (1H, br s).

Preparation 6

(1) To a solution of 2,6-dimethylbenzoic acid (20 g) in conc. sulfuric acid (100 ml) was dropwise added under ice-cooling a mixture of 70% nitric acid and conc. sulfuric acid (21.6 ml), which was prepared by dropwise adding conc. sulfuric acid (10.8 ml) to 70% nitric acid (15.1 ml) under ice-cooling, and the mixture was stirred for 1 hour at the same temperature. Ice-water was added to the reaction mixture, and the resulting precipitates were filtered off. The filtrate was concentrated, and the residue was purified by flash chromatography (dichloromethane:methanol=20:1 including 1% acetic acid) to give 2,6-dimethyl-3-nitrobenzoic acid (7.0 g) as a colorless crystal.

mp: 109–112° C.; NMR (CDCl$_3$, $\delta$): 2.48 (3H, s), 2.57 (2H, s), 7.22 (1H, d, J=8 Hz), 7.87 (1H, d, J=8 Hz).

(2) To a solution of 2,6-dimethyl-3-nitrobenzoic acid (3.09 g) in tetrahydrofuran (5 ml) was added borane-methyl sulfide complex (2.41 g) under ice-cooling, and the mixture was stirred for 30 minutes at the same temperature, for 1 hour at ambient temperature, and then for 4 hours under heating. To the mixture was added 1N hydrochloric acid under ice-cooling, and the mixture was allowed to stand overnight. The mixture was extracted with ethyl acetate twice, and the combined organic layer was washed with saturated sodium bicarbonate solution, water and brine, dried over magnesium sulfate and concentrated. The residue was recrystallized with diisopropyl ether to give 2,6-dimethyl-3-nitrobenzyl alcohol (2.296 g) as a pale yellow crystal.

mp: 99–101° C.; NMR (CDCl$_3$, $\delta$): 1.45 (1H, t, J=5 Hz), 2.50 (3H, s), 2.56 (3H, s), 4.80 (2H, d, J=5 Hz), 7.15 (1H, d, J=8 Hz), 7.64 (1H, d, J=8 Hz).

(3) To a solution of 2,6-dimethyl-3-nitrobenzyl alcohol (1.5 g) and triethylamine (1.01 g) in dichloromethane (15 ml) was dropwise added methanesulfonyl chloride (1.04 g) under ice-cooling, and the mixture was stirred for 30 minutes at the same temperature. The reaction mixture was washed with saturated sodium bicarbonate solution and water, dried over magnesium sulfate and concentrated in vacuo to give a mixture of 2,6-dimethyl-3-nitrobenzyl methanesulfonate and 2,6-dimethyl-3-nitrobenzyl chloride, which was used as a starting compound at the following example without further purification.

(4) To a mixture of 2,6-dimethyl-3-nitrobenzyl methanesulfonate and 2,6-dimethyl-3-nitrobenzyl chloride obtained above in N,N-dimethylformamide (13 ml) was added sodium hydride (60% in oil, 335 mg) under ice-bath cooling, and the mixture was stirred for 15 minutes. To the mixture was added 8-hydroxy-2-methylquinoline (1.27 g), and the mixture was stirred for 1 hour at ambient temperature. Water was added thereto, and the resulting precipitate was collected by filtration to give 8-(2,6-dimethyl-3-nitrobenzyloxy)-2-methylquinoline (2.53 g).

mp: 150–152° C.; NMR (CDCl$_3$, $\delta$): 2.58 (3H, s), 2.65 (3H, s), 2.73 (3H, s), 5.39 (2H, s), 7.18–7.33 (3H, m), 7.38–7.50 (2H, m), 6.60 (1H, s), 7.72 (1H, d, J=8 Hz), 8.04 (1H, d, J=8 Hz).

(5) To a suspension of 8-(2,6-dimethyl-3-nitrobenzyloxy)-2-methylquinoline (2.34 g), ferric chloride (70.6 mg) and carbon (70.6 mg) in methanol (35 ml) was added hydrazine monohydrate (1.09 g) at 65° C., and the mixture was refluxed for 2 hours. Methanol (20 ml) was added thereto, and the mixture was refluxed for 1 hour. After cooling chloroform was added thereto, and the resulting precipitates were filtered off. The filtrate was concentrated and the residue was dissolved in chloroform. The solution was washed with saturated sodium bicarbonate solution, water and brine, dried over magnesium sulfate and concentrated. The residue was crystallized with ethyl acetate to give 8-(3-amino-2,6-dimethylbenzyloxy)-2-methylquinoline (1.67 g) as a pale brown crystal.

mp: 204–205° C.; NMR (CDCl$_3$, δ): 2.27 (3H, s), 2.37 (3H, s), 2.72 (3H, s), 3.57 (2H, br s), 5.32 (2H, s), 6.67 (1H, d, J=8 Hz), 6.91 (1H, d, J=8 Hz), 7.18–7.31 (2H, m), 7.36–7.42 (2H, m), 8.00 (1H, d, J=8 Hz).

Example 1

(1) To a solution of 3-(tert-butyldiphenylsilyloxymethyl)-2,4-dichloroaniline (6.08 g) in acetic acid (15 ml) was added 2,5-dimethoxytetrahydrofuran (1.87 g). The mixture was stirred at 90° C. for 1 hour and evaporated under reduced pressure. The residue was purified by a silica gel column chromatography eluted with n-hexane-ethyl acetate to give 1-[3-(tert-butyldiphenylsilyloxymethyl)-2,4-dichlorophenyl]pyrrole (5.82 g) as a pale yellow oil.

NMR (CDCl$_3$, δ): 1.06 (9H, s), 4.98 (2H, s), 6.32 (2H, d, J=4 Hz), 6.83 (2H, d, J=4 Hz), 7.22 (1H, d, J=10 Hz), 7.32–7.48 (7H), 7.74 (4H, d, J=8 Hz).

(2) To a solution of 1-[3-(tert-butyldiphenylsilyloxymethyl)-2,4-dichlorophenyl]pyrrole (1.20 g) in anhydrous dichloromethane (12 ml) was added a solution of chlorosulfonyl isocyanate (0.28 ml) in anhydrous dichloromethane (2.8 ml) dropwise in a dry ice-carbon tetrachloride bath. The mixture was stirred at the same temperature for 30 minutes and then at ambient temperature for additional 1 hour. Anhydrous dimethylformamide (0.4 ml) was added to this mixture dropwise in a dry ice-carbon tetrachloride bath. After stirring at the same temperature for 30 minutes and at ambient temperature for additional 1 hour, the reaction mixture was treated with 4N-hydrochloric acid under ice-water cooling for 30 minutes. The organic layer was isolated and the aqueous layer was extracted with chloroform twice. The combined organic phases were washed with saturated aqueous sodium hydrogen carbonate, dried over magnesium sulfate and evaporated in vacuo. The residue was purified by a silica gel column chromatography eluted with n-hexane—ethyl acetate to give 1-[3-(tert-butyldiphenylsilyloxymethyl)-2,4-dichlorophenyl]-2-cyanopyrrole (930 mg) as a pale yellow oil.

NMR (CDCl$_3$, δ): 1.07 (9H, s), 4.98 (2H, s), 6.38 (1H, t, J=4 Hz), 6.93 (1H, d, J=4 Hz), 6.98 (1H, d, J=4 Hz), 7.31 (1H, d, J=8 Hz), 7.33–7.48 (7H), 7.68–7.77 (4H).

(3) To a solution of 1-[3-(tert-butyldiphenylsilyloxymethyl)-2,4-dichlorophenyl]-2-cyanopyrrole (820 mg) in anhydrous tetrahydrofuran (16 ml) was added lithium aluminum hydride (74 mg) and the mixture was stirred at ambient temperature for 1 hour. The reaction mixture was quenched by adding water (2 ml) dropwise under ice-water cooling. Ethyl acetate (50 ml) and water (50 ml) were added thereto and the precipitate was filtered off. The organic layer was isolated and the aqueous layer was extracted with ethyl acetate. The combined organic phases were washed with brine, dried over magnesium sulfate and evaporated in vacuo. The residue was purified by a silica gel column chromatography eluted with chloroform-methanol to give 2-aminomethyl-1-[3-(tert-butyldiphenylsilyloxymethyl)-2,4-dichlorophenyl]pyrrole (414 mg) as a pale yellow oil.

NMR (CDCl$_3$, δ): 1.06 (9H, s), 3.52 (1H, d, J=15 Hz), 3.63 (1H, d, J=15 Hz), 4.97 (2H, s), 6.19–6.30 (2H), 6.63 (1H, d, J=4 Hz), 7.30 (1H, d, J=8 Hz), 7.34–7.48 (7H), 7.68–7.79 (4H).

(4) To a solution of 2-aminomethyl-1-[3-(tert-butyldiphenylsilyloxymethyl)-2,4-dichlorophenyl]pyrrole (465 mg) in anhydrous dimethylformamide (7 ml) were added 4-(methylcarbamoyl)cinnamic acid (206 mg), 1-ethyl-3-(3-dimethylaminopropyl)carbodiimide hydrochloride (219 mg) and 1-hydroxybenzotriazole (185 mg). The mixture was stirred at ambient temperature for 3 hours and partitioned between ethyl acetate and water. The organic layer was isolated and the aqueous layer was extracted with ethyl acetate. The organic layers were combined, washed with saturated aqueous sodium hydrogen carbonate and brine, dried over magnesium sulfate and evaporated in vacuo. The residue was triturated with diisopropyl ether to give 1-[3-(tert-butyldiphenylsilyloxymethyl)-2,4-dichlorophenyl]-2-[4-(methylcarbamoyl)cinnamoylaminomethyl]pyrrole (622 mg) as a brownish powder.

NMR (CDCl$_3$, δ): 1.02 (9H, s), 3.02 (3H, d, J=6 Hz), 4.32 (2H, d, J=6 Hz), 4.88 (2H, s), 5.62 (1H, t-like), 6.10 (1H, br s), 6.24 (1H, d, J=16 Hz), 6.27–6.32 (2H), 6.68 (1H, d, J=4 Hz), 7.23–7.50 (11H), 7.64–7.74 (6H).

(5) To a solution of 1-[3-(tert-butyldiphenylsilyloxymethyl)-2,4-dichlorophenyl]-2-[4-(methylcarbamoyl)cinnamoylaminomethyl]pyrrole (620 mg) in tetrahydrofuran (6 ml) was added 1N solution of tetrabutylammonium fluoride in tetrahydrofuran (2.5 ml). The mixture was stirred at ambient temperature for 6 hours and partitioned between ethyl acetate and water. The organic layer was isolated and the aqueous layer was extracted with ethyl acetate. The combined organic layers were washed with 1N hydrochloric acid and brine, dried over magnesium sulfate and evaporated in vacuo. The residue was triturated with methanol to give 1-(2,4-dichloro-3-hydroxymethylphenyl)-2-[4-(methylcarbamoyl)cinnamoylaminomethyl]pyrrole (197 mg) as a brownish powder.

NMR (DMSO-d$_6$, δ): 2.79 (3H, d, J=6 Hz), 4.06 (1H, dd, J=16, 6 Hz), 4.21 (1H, dd, J=16, 6 Hz), 4.70 (2H, d, J=6 Hz), 5.30 (1H, t, J=6 Hz), 6.16–6.23 (2H), 6.64 (1H, d, J=16 Hz), 6.76 (1H, br s), 7.34 (1H, d, J=16 Hz) 7.46 (1H, d, J=8 Hz), 7.53–7.63 (3H), 7.86 (2H, d, J=8 Hz), 8.28 (1H, t-like), 8.48 (1H, br s).

(6) To a mixture of 1-(2,4-dichloro-3-hydroxymethylphenyl)-2-[4-(methylcarbamoyl)cinnamoylaminomethyl]pyrrole (148 mg), triethylamine (0.11 ml) and anhydrous dimethylformamide (1 ml) was added a 1M solution of methanesulfonyl chloride in dimethylformamide (0.77 ml) under ice-water cooling. The mixture was stirred at ambient temperature for 4 hours and partitioned between chloroform and saturated aqueous solution of sodium hydrogen carbonate. The organic layer was isolated, dried over magnesium sulfate and evaporated in vacuo to give a brown oil. The residue was purified by preparative thin layer chromatography (chloroform-methanol) to give 1-(2,4-dichloro-3-chloromethylphenyl)-2-[4-(methylcarbamoyl)cinnamoylaminomethyl]pyrrole (120 mg) as an amorphous powder.

NMR (CDCl₃—CD₃OD, δ): 2.99 (3H, d, J=5 Hz), 4.28 (1H, d, J=16 Hz), 4.38 (1H, d, J=16 Hz), 4.86 (2H, s), 6.26–6.40 (4H), 6.69 (1H, br s), 6.83 (1H, br s), 7.34 (1H, d, J=8 Hz), 7.43 (1H, d, J=8 Hz), 7.50 (2H, d, J=8 Hz), 7.75 (2H, d, J=8 Hz).

(7) A mixture of 1-(2,4-dichloro-3-chloromethylphenyl)-2-[4-(methylcarbamoyl)cinnamoylaminomethyl]pyrrole (50 mg), 2-methyl-8-hydroxyquinoline (17 mg) and potassium carbonate (44 mg) in N,N-dimethylformamide (2 ml) was stirred at ambient temperature for 1 day. The mixture was poured into water and extracted with chloroform. The organic layer was washed with water and brine, dried over magnesium sulfate and evaporated in vacuo. The residue was purified by preparative thin-layer chromatography on silica gel to give 1-[2,4-dichloro-3-(2-methylquinolin-8-yloxymethyl)phenyl]-2-[4-(methylcarbamoyl)-cinnamoylaminomethyl]pyrrole (40 ml) as an amorphous powder.

NMR (CDCl₃, δ): 2.57 (3H, s), 2.91 (3H, d, J=6 Hz), 4.23 (1H, dd, J=4, 16 Hz), 4.44 (1H, dd, J=4, 16 Hz), 5.41–5.56 (2H, m), 6.23 (1H, dd, J=4, 3 Hz), 6.32 (1H, br s), 6.40 (1H, d, J=16 Hz), 6.69 (1H, br s), 6.92 (1H, t-like), 6.99 (1H, q-like), 7.14 (1H, t, J=8 Hz), 7.20–7.29 (6H, m), 7.43 (2H, d, J=8 Hz), 7.60 (2H, d, J=8 Hz), 8.03 (1H, d, J=8 Hz).

(8) To a suspension of 1-[2,4-dichloro-3-(2-methylquinolin-8-yloxymethyl)phenyl]-2-(4-(methylcarbamoyl)-cinnamoylaminomethyl]pyrrole (35 mg) in methanol (2 ml) was added 10% solution of hydrogen chloride in methanol (0.3 ml) and allowed to stand for 10 minutes. The reaction mixture was evaporated in vacuo and hydrogen chloride was azeotropically removed with methanol. The residue was dried at ambient temperature for 6 hours in vacuo and solidified with ethyl acetate to give 1-[2,4-dichloro-3-(2-methylquinolin-8-yloxymethyl)phenyl]-2-[4-(methylcarbamoyl)-cinnamoylaminomethyl]pyrrole hydrochloride (32 mg) as an amorphous powder.

NMR (DMSO-d₆, δ): 2.79(3H, d, J=5 Hz), 2.85 (3H, s), 4.15–4.28 (1H, m), 4.38–4.53 (1H, br peak), 5.51 (1H, d, J=10 Hz), 5.60 (1H, d, J=10 Hz), 6.20–6.28 (2H, m), 6.60 (1H, d, J=16 Hz), 6.83–6.88 (1H, m), 7.32 (1H, d, J=16 Hz), 7.53–7.62 (3H, m), 7.62–7.97 (7H, m), 8.40–8.53 (2H, m).

Example 2

(1) 1-[2,4-Dichloro-3-(2-methylquinolin-8-yloxymethyl)-phenyl]pyrrole was obtained by reacting 8-(3-amino-2,6-dichlorobenzyloxy)-2-methylquinoline with 2,5-dimethoxytetrahydrofuran according to a similar manner to that of Example 1-(1).

NMR (CDCl₃, δ): 2.75 (3H, s), 5.68 (2H, s), 6,33 (2H, d, J=3 Hz), 6.87 (2H, d, J=3 Hz), 7.24–7.48 (6H), 8.02 (1H, d, J=8 Hz).

(2) 1-[2,4-Dichloro-3-(2-methylquinolin-8-yloxymethyl)-phenyl]-2-cyanopyrrole was obtained according to a similar manner to that of Example 1-(2).

NMR (CDCl₃, δ): 2.76 (3H, s), 5.69 (2H, s), 6.39 (1H, t, J=4 Hz), 6.95–7.02 (2H), 7.23–7.56 (6H), 8.03 (1H, d, J=8 Hz).

(3) 2-Aminomethyl-1-[2,4-dichloro-3-(2-methylquinolin-8-yloxymethyl)phenyl]pyrrole was obtained according to a similar manner to that of Example 1-(3).

NMR (CDCl₃, δ): 2.75 (3H, s), 3.55 (1H, d, J=16 Hz), 3.66 (1H, d, J=16 Hz), 5.70 (2H, s), 6.21 (1H, d, J=4 Hz), 6.28 (1H, t, J=4 Hz), 6.64 (1H, d, J=4 Hz), 7.23–7.51 (6H), 8.02 (1H, d, J=8 Hz).

(4) To a solution of 2-aminomethyl-1-[2,4-dichloro-3-(2-methylquinolin-8-yloxymethyl)phenyl]pyrrole (100 mg) and 4-(dimethylcarbamoyl)cinnamic acid (58.5 mg) in N,N-dimethylformamide (2 ml) were added 1-ethyl-3-(3-dimethylaminopropyl)carbodiimide hydrochloride (55.8 mg) and 1-hydroxybenzotriazole (49.2 mg) at ambient temperature, and the mixture was allowed to stand for 18 hours. The reaction mixture was poured into water and extracted with chloroform. The separated organic layer was washed with water, saturated sodium bicarbonate solution and brine, dried over magnesium sulfate and evaporated in vacuo. The residue was purified by preparative thin layer chromatography (chloroform:methanol=20:1, V/V) to give 1-[2,4-dichloro-3-(2-methylquinolin-8-yloxymethyl) phenyl]-2-[4-(dimethylcarbamoyl)cinnamoylaminomethyl] pyrrole (122 mg) as an amorphous powder.

NMR (CDCl₃, δ): 2.63 (3H, s), 2.92 (3H, br s), 3.09 (3H, br s), 4.25–4.35 (1H, m), 4.41–4.52 (1H, m), 5.52 (1H, d, J=10 Hz), 5.60 (1H, d, J=10 Hz), 6.24–6.37 (4H, m), 6.67 (1H, s-like), 7.13–7.30 (6H, m), 7.30–7.51 (5H, m), 8.02 (1H, d, J=8 Hz).

its hydrochloride

NMR (DMSO-d₆, δ): 2.89 (3H, s), 2.91 (3H, br s), 2.98 (3H, br s), 4.22 (1H, dd, J=15, 3 Hz), 3.43–3.55 (1H, m), 5.53 (1H, d, J=10 Hz), 5.62 (1H, d, J=10 Hz), 6.20–6.23 (1H, m), 6.24–6.28 (1H, m), 6.58 (1H, d, J=16 Hz), 6.82–6.86 (1H, m), 7.31 (1H, d, J=16 Hz), 7.43 (2H, d, J=8 Hz), 7.50–7.62 (3H, m), 7.68 (1H, d, J=8 Hz), 7.73–8.02 (4H, m), 8.49 (1H, t, J=7 Hz), 8.99 (1H, br peak).

Example 3

The following compounds were obtained according to a similar manner to that of Example 2-(4).

(1) 2-(4-Acetamido-3-methylcinnamoylaminomethyl)-1-[2,4-dichloro-3-(2-methylquinolin-8-yloxymethyl)phenyl]-pyrrole NMR (CDCl₃, δ): 2.13 (3H, s), 2.22 (3H, br s), 2.65 (3H, s), 4.27–4.49 (2H, m), 5.46–5.62 (2H, m), 6.18–6.43 (4H, m), 6.63–6.70 (1H, m), 6.98 (1H, br s), 7.07–7.20 (3H, m), 7.20–7.30 (2H, m), 7.30–7.50 (4H, m), 7.69–7.81 (1H, m), 8.04 (1H, d, J=8 Hz).

its hydrochloride

NMR (DMSO-d₆, δ): 2.07 (3H, s), 2.20 (3H, s), 2.86 (3H, s), 4.13–4.25 (1H, m), 4.45 (1H, br peak), 5.52 (1H, d, J=10 Hz), 5.61 (1H, d, J=10 Hz), 6.17–6.26 (2H, m), 6.44 (1H, d, J=16 Hz), 6.81–6.86 (1H, m), 7.20 (1H, d, J=16 Hz), 7.26–7.33 (2H, m), 7.52 (1H, d, J=8 Hz), 4.56 (1H, d, J=8 Hz), 7.62–8.00 (5H, m), 8.36 (1H, t-like), 8.94 (1H, br peak), 9.35 (1H, s).

(2) 1-[2,4-Dichloro-3-(2-methylquinolin-8-yloxymethyl) phenyl]-2-[4-(2-oxopyrrolidin-1-yl)-cinnamoylaminomethyl]pyrrole NMR (CDCl₃, δ): 2.10–2.24 (2H, m), 2.63 (2H, t, J=7.5 Hz), 2.67 (3H, s), 3.83 (2H, t, J=7.5 Hz), 4.23–4.33 (1H, m), 4.41–4.53 (1H, m), 5.49–5.63 (2H, m), 6.16–6.31 (3H, m), 6.31–6.39 (1H, m), 6.64–6.70 (1H, m), 7.12–7.20 (1H, m), 7.20–7.30 (3H, m), 7.33–7.55 (7H, m), 8.05 (1H, d, J=8 Hz).

its hydrochloride

NMR (DMSO-d₆, δ): 2.00–2.14 (2H, m), 2.48–2.58 (2H, m), 2.85 (3H, s), 3.83 (2H, t, J=7 Hz), 4.13–4.26 (1H, m), 4.44 (1H, br peak), 5.51 (1H, d, J=10 Hz), 5.62 (1H, d, J=10 Hz), 6.19–6.27 (2H, m), 6.45 (1H, d, J=16 Hz), 6.85 (1H, d, J=2 Hz), 7.24 (1H, d, J=16 Hz), 7.50 (2H, d, J=8 Hz), 7.58 (1H, d, J=8 Hz), 7.62–7.95 (7H, m), 8.31–8.43 (1H, m), 8.93 (1H, br peak).

(3) 1-[2,4-Dichloro-3-(2-methylquinolin-8-yloxymethyl) phenyl]-2-[3-methoxy-4-(methylcarbamoyl) cinnamoylaminomethyl]pyrrole NMR (CDCl₃, δ): 2.63 (3H, s), 2.99 (3H, d, J=6 Hz), 3.77 (3H, s), 4.30–4.41 (1H, m), 4.41–4.53 (1H, m), 5.48–5.63 (2H, m), 6.28 (1H, t, J=3 Hz), 6.31–6.37 (1H, m), 6.37–6.47 (2H, m), 6.65–6.70 (1H, m), 6.86–6.95 (2H, m), 7.12–7.20 (1H, m), 7.20–7.28 (1H, m), 7.33–7.50 (5H, m), 7.70–7.79 (1H, m), 7.97 (1H, d, J=8 Hz), 8.03 (1H, d, J=8 Hz).

its hydrochloride

NMR (DMSO-d₆, δ): 2.80 (3H, d, J=5 Hz), 2.87 (3H, s), 3.90 (3H, s), 4.17–4.27 (1H, m), 4.34–4.47 (1H, m), 5.53 (1H, d, J=10 Hz), 5.63 (1H, d, J=10 Hz), 6.19–6.29 (2H, m), 6.64 (1H, d, J=16 Hz), 6.85 (1H, d, J=2 Hz), 7.16 (1H, d, J=8 Hz), 7.21 (1H, s-like), 7.33 (1H, d, J=16 Hz), 7.11 (1H, d, J=8 Hz), 7.18–7.99 (6H, m), 8.15 (1H, q-like), 8.44 (1H, t-like), 8.94 (1H, br peak).

(4) 1-[2,4-Dichloro-3-(2-methylquinolin-8-yloxymethyl)phenyl]-2-[4-[(2-pyridylmethyl)carbamoyl]cinnamoylaminomethyl]pyrrole NMR (DMSO-d₆, δ): 2.59 (3H, s), 4.10 (1H, dd, J=4, 15 Hz), 4.24–4.35 (1H, m), 4.59 (2H, d, J=7 Hz), 5.37 (1H, d, J=5 Hz), 6.18–6.26 (2H, m), 6.68 (1H, d, J=16 Hz), 6.88 (1H, d, J=3 Hz), 7.14 (1H, d, J=8 Hz), 7.27 (1H, dd, J=6, 8 Hz), 7.30–7.37 (2H, m), 7.37–7.44 (2H, m), 7.51 (1H, d, J=8 Hz), 7.60–7.69 (3H, m), 7.71 (1H, d, J=8 Hz), 7.77 (1H, t, J=8 Hz), 7.98 (2H, d, J=8 Hz), 8.20 (1H, d, J=8 Hz), 8.30 (1H, t, J=6 Hz), 7.50–7.54 (1H, m), 9.18 (1H, t, J=5 Hz).

its dihydrochloride

NMR (DMSO-d₆, δ): 2.85 (3H, s), 4.16–4.28 (1H, m), 4.39–4.53 (1H, m), 5.54 (1H, d, J=10 Hz), 5.63 (1H, d, J=10 Hz), 6.20–6.24 (1H, m), 6.24–6.28 (1H, m), 6.65 (1H, d, J=16 Hz), 6.85 (1H, d, J=2 Hz), 7.35 (1H, d, J=16 Hz), 7.57–8.03 (12H, m), 8.27 (1H, t, J=8 Hz), 8.50 (1H, t, J=5 Hz), 8.74 (1H, d, J=5 Hz), 8.93 (1H, br peak), 9.46 (1H, t, J=7 Hz).

(5) 1-[2,4-Dichloro-3-(2-methylquinolin-8-yloxymethyl)phenyl]-2-[3-[4-[(2-pyridylmethyl)carbamoyl]phenyl]propionylaminomethyl]pyrrole NMR (CDCl₃, δ): 2.33 (2H, t, J=7.5 Hz), 2.62 (3H, s), 2.86 (2H, t, J=7.5 Hz), 4.05–4.16 (1H, m), 4.25–4.37 (1H, m), 4.75 (2H, d, J=5 Hz), 5.60 (2H, s), 6.09 (1H, br peak), 6.21–6.29 (2H, m), 6.61–6.67 (1H, m), 7.05 (2H, d, J=8 Hz), 7.19–7.37 (5H, m), 7.37–7.44 (2H, m), 7.44–7.51 (2H, m), 7.55–7.64 (2H, m), 7.64–7.74 (2H, m), 8.00 (1H, d, J=8 Hz), 8.54–8.60 (1H, m).

its dihydrochloride

NMR (DMSO-d₆, δ): 2.21–2.38 (2H, m), 2.67–2.79 (2H, m), 2.87 (3H, s), 3.98–4.09 (1H, m), 4.32–4.43 (1H, m), 4.76 (2H, d, J=6 Hz), 5.57 (1H, d, J=10 Hz), 5.71 (1H, d, J=10 Hz), 6.13–6.21 (2H, m), 6.83 (1H, d, J=2 Hz), 7.26 (2H, d, J=8 Hz), 7.57 (1H, d, J=8 Hz), 7.73–7.99 (9H, m), 8.25 (1H, t, J=5 Hz), 8.36 (1H, t, J=8 Hz), 8.77 (1H, d, J=5 Hz), 8.97 (1H, d, J=8 Hz), 9.36 (1H, t, J=5 Hz).

(6) 1-[2,4-Dichloro-3-(2-methylquinolin-8-yloxymethyl)phenyl]-2-[4-(methanesulfonamido)-cinnamoylaminomethyl]pyrrole NMR (DMSO-d₆, δ): 2.59 (3H, s), 3.03 (3H, s), 4.01–4.13 (1H, m), 4.19–4.33 (1H, m), 5.38 (2H, d, J=5 Hz), 6.16–6.25 (2H, m), 6.49 (1H, d, J=16 Hz), 6.86 (1H, d, J=2 Hz), 7.16–7.31 (4H, m), 7.37–7.46 (2H, m), 7.46–7.55 (3H, m), 7.62 (1H, d, J=8 Hz), 7.71 (1H, d, J=8 Hz), 8.16–8.25 (2H, m), 10.02 (1H, s).

its hydrochloride

NMR (DMSO-d₆, δ): 2.83 (3H, s), 3.02 (3H, s), 4.14–4.25 (1H, m), 4.41 (1H, br peak), 5.47–5.65 (2H, m), 6.17–6.26 (2H, m), 6.43 (1H, d, J=16 Hz), 6.81–6.86 (1H, m), 7.18–7.28 (3H, m), 7.47 (2H, d, J=8 Hz), 7.58 (1H, d, J=8 Hz), 7.69 (1H, d, J=8 Hz), 7.70–7.95 (5H, m), 8.38 (1H, t-like), 8.92 (1H, br peak).

(7) 1-[2,4-Dichloro-3-(2-methylquinolin-8-yloxymethyl)phenyl]-2-[4-[N-(2-methoxyacetyl)-N-(pyridin-3-ylmethyl)amino]cinnamoylaminomethyl]pyrrole NMR (DMSO-d₆, δ): 2.60 (3H, s), 3.20 (3H, s), 3.86 (2H, s), 4.04–4.16 (1H, m), 4.16–4.28 (1H, m), 4.90 (2H, s), 5.36–5.52 (2H, m), 6.16–6.24 (2H, m), 6.57 (1H, d, J=16 Hz), 6.85–6.90 (1H, m), 7.23–7.37 (5H, m), 7.37–7.47 (2H, m), 7.47–7.57 (3H, m), 7.57–7.66 (2H, m), 7.71 (1H, d, J=8 Hz), 8.20 (1H, d, J=8 Hz), 8.26 (1H, t, J=5 Hz), 8.37 (1H, s-like), 8.44 (1H, d, J=5 Hz).

its dihydrochloride

NMR (DMSO-d₆, δ): 2.85 (3H, s), 3.20 (3H, s), 3.87 (2H, s), 4.14–4.24 (1H, m), 4.35–4.47 (1H, m), 5.02 (2H, s), 5.55 (1H, d, J=10 Hz), 5.63 (1H, d, J=10 Hz), 6.20–6.27 (2H, m), 6.55 (1H, d, J=16 Hz), 6.83 (1H, d, J=2 Hz), 7.30 (1H, d, J=16 Hz), 7.35 (2H, d, J=8 Hz), 7.53 (2H, d, J=8 Hz), 7.60 (1H, d, J=8 Hz), 7.69 (1H, d, J=8 Hz), 7.75–7.92 (5H, m), 8.23 (1H, d, J=8 Hz), 8.46 (1H, t, J=7 Hz), 8.67–8.76 (2H, m), 8.90 (1H, d, J=8 Hz).

(8) 2-[(E)-3-(6-Acetamidopyridin-3-yl)acryloylaminomethyl]-1-[2,4-dichloro-3-(2-methylquinolin-8-yloxymethyl)phenyl]pyrrole NMR (CDCl₃, δ): 2.11 (3H, s), 2.59 (3H, s), 4.03–4.17 (1H, m), 4.17–4.32 (1H, m), 5.42 (2H, d, J=3 Hz), 6.16–6.25 (2H, m), 6.57 (1H, d, J=16 Hz), 6.86 (1H, d, J=3 Hz), 7.25 (1H, d, J=8 Hz), 7.31 (1H, d, J=16 Hz), 7.36–7.47 (2H, m), 7.53 (1H, d, J=8 Hz), 7.63 (1H, d, J=8 Hz), 7.71 (1H, d, J=8 Hz), 7.91–7.98 (1H, m), 8.11 (1H, d, J=8 Hz), 8.17–8.30 (2H, m), 8.45 (1H, s-like), 10.66 (1H, s).

its dihydrochloride

NMR (DMSO-d₆, δ): 2.11 (3H, s), 2.91 (3H, s), 4.13–4.24 (1H, m), 4.45–4.68 (1H, m), 5.56 (1H, d, J=10 Hz), 5.65 (1H, d, J=10 Hz), 6.19–6.27 (2H, m), 6.51 (1H, d, J=16 Hz), 6.81–6.87 (1H, m), 7.27 (1H, d, J=16 Hz), 7.57 (1H, d, J=8 Hz), 7.67 (1H, d, J=8 Hz), 7.77–8.03 (5H, m), 8.09 (1H, d, J=8 Hz), 8.41 (1H, s-like), 8.43–8.50 (1H, m), 8.97–9.09 (1H, m), 10.72 (1H, s).

(9) 2-[(E)-3-(6-Aminopyridin-3-yl)acryloylaminomethyl]-1-[2,4-dichloro-3-(2-methylquinolin-8-yloxymethyl)phenyl]pyrrole NMR (DMSO₆, δ): 2.59 (3H, s), 4.00–4.10 (1H, m), 4.19–4.21 (1H, m), 5.32–5.45 (2H, m), 6.16–6.22 (2H, m), 6.29 (1H, d, J=16 Hz), 6.38–6.45 (2H, m), 6.48 (1H, d, J=8 Hz), 6.83–6.87 (1H, m), 7.11–7.23 (2H, m), 7.37–7.48 (2H, m), 7.48–7.58 (2H, m), 7.61 (1H, d, J=8 Hz), 7.70 (1H, d, J=8 Hz), 7.99–8.09 (2H, m), 8.20 (1H, d, J=8 Hz).

Example 4

To a mixture of 2-[(E)-3-(6-aminopyridin-3-yl)acryloylaminomethyl]-1-[2,4-dichloro-3-(2-methylquinolin-8-yloxymethyl)phenyl]pyrrole (152 mg) and triethylamine (96 mg) in dichloromethane (3 ml) was added 2-methylnicotinoyl chloride hydrochloride (115 mg) under nitrogen in ice water bath and stirred for 1 hour at the same temperature. The reaction solvent was concentrated in vacuo and the residue was dissolved in methanol. To the solution was added 1M sodium hydroxide solution (0.5 ml) and stirred for 30 minutes. The solution was evaporated and partitioned between chloroform and water. The organic layer was washed with water and brine, dried over magnesium sulfate and evaporated in vacuo. The residue was purified by preparative thin-layer chromatography on silica gel (ethyl acetate) to give 1-[2,4-dichloro-3-(2-methylquinolin-8-yloxymethyl)phenyl]-2-[(E)-3-[6-[2-methylnicotinamido]pyridin-3-yl]acryloylaminomethyl]pyrrole (124 mg) as an amorphous powder.

NMR (DMSO₆, δ): 2.57 (3H, s), 4.26 (3H, s), 4.06–4.17 (1H, m), 4.21–4.33 (1H, m), 5.35–5.47 (2H, m), 6.18–6.25

(2H, m), 6.63 (1H, d, J=16 Hz), 6.85–6.90 (1H, m), 7.24 (1H, d, J=8 Hz), 7.29–7.36 (2H, m), 7.36–7.47 (3H, m), 7.53 (1H, d, J=8 Hz), 7.64 (1H, d, J=8 Hz), 7.73 (1H, d, J=8 Hz), 7.88 (1H, d, J=8 Hz), 8.03 (1H, d, J=8 Hz), 8.16–8.31 (3H, m), 8.51–8.57 (2H, m).
its trihydrochloride
NMR (DMSO-$d_6$, δ): 2.70 (3H, s), 2.87 (3H, s), 4.13–4.27 (1H, m), 4.38–4.52 (1H, m), 5.55 (1H, d, J=10 Hz), 5.64 (1H, d, J=10 Hz), 6.20–6.28 (2H, m), 6.60 (1H, d, J=16 Hz), 6.83–6.88 (1H, m), 7.33 (1H, d, J=16 Hz), 7.60 (1H, d, J=8 Hz), 7.63–7.72 (2H, m), 7.72–7.97 (5H, m), 8.03 (1H, dd, J=2, 8 Hz), 8.23 (1H, d, J=8 Hz), 8.30 (1H, d, J=8 Hz), 8.43–8.53 (2H, m), 8.73 (1H, d, J=6 Hz), 8.92 (1H, br peak).

Example 5

A mixture of 2-aminomethyl-1-[2,4-dichloro-3-(2-methylquinolin-8-yloxymethyl)phenyl]pyrrole (100 mg), phenyl 3-(dimethylcarbamoyl)phenylcarbamate (70 mg) and triethylamine (49 mg) in N,N-dimethylformamide (3 ml) was stirred at 80° C. for 2 hours. The mixture was poured into water and extracted with chloroform. The organic layer was washed with water and brine, dried over magnesium sulfate and evaporated in vacuo. The residue was purified by preparative thin-layer chromatography on silica gel to give 1-[2,4-dichloro-3-(2-methylquinolin-8-yloxymethyl)phenyl]-2-[N'-[3-(dimethylcarbamoyl)phenyl]ureidomethyl]pyrrole (98 mg) as an amorphous powder.
NMR (CDCl$_3$, δ): 2.10 (3H, s), 2.28 (3H, br s), 2.96 (3H, br s), 4.17 (1H, d, J=15 Hz), 4.91–5.14 (2H, m), 5.30 (1H, d, J=10 Hz), 5.64 (1H, d, J=10 Hz), 6.14–6.25 (2H, m), 6.58–6.66 (1H, m), 6.91 (1H, d, J=8 Hz), 7.05 (1H, t, J=8 Hz), 7.15 (1H, d, J=8 Hz), 7.18–7.34 (4H, m), 7.34–7.55 (4H, m), 8.10 (1H, d, J=8 Hz), 9.29 (1H, s).
its hydrochloride
NMR (DMSO-$d_6$, δ): 2.74–2.93 (9H, m), 4.07–4.18 (1H, m), 4.18–4.30 (1H, m), 5.48 (1H, d, J=10 Hz), 5.58 (1H, d, J=10 Hz), 6.18–6.25 (2H, m), 6.50 (1H, br peak), 6.78–6.83 (1H, m), 6.83–6.91 (1H, m), 7.20–7.30 (2H, m), 7.36 (1H, s), 7.62 (1H, d, J=8 Hz), 7.70 (1H, d, J=8 Hz), 7.73–7.95 (4H, m), 8.78 (1H, s), 8.92 (1H, br peak).

Example 6

1-[2,4-Dichloro-3-(4-methoxy-2-methylquinolin-8-yloxymethyl)phenyl]-2-[4-(methylcarbamoyl) cinnamoylaminomethyl]pyrrole is obtained by reacting 1-(2,4-dichloro-3-chloromethylphenyl)-2-[4-(methylcarbamoyl)-cinnamoylaminomethyl]pyrrole with 4-methoxy-2-methyl-8-hydroxyquinoline according to a similar manner to that of Example 1-(7).

Example 7

1-[2,4-Dichloro-3-(4-dimethylamino-2-methylquinolin-8-yloxymethyl)phenyl]-2-[4-(methylcarbamoyl) cinnamoylaminomethyl]pyrrole is obtained by reacting 1-(2,4-dichloro-3-chloromethylphenyl)-2-[4-(methylcarbamoyl) cinnamoylaminomethyl]pyrrole with 4-dimethylamino-2-methyl-8-hydroxyquinoline according to a similar manner to that of Example 1-(7).

Example 8

1-[2,4-Dichloro-3-(2-methoxy-1-methyl-1H-benzimidazol-4-yloxymethyl)phenyl]-2-[4-(methylcarbamoyl)cinnamoylaminomethyl]pyrrole is obtained by reacting 1-(2,4-dichloro-3-chloromethylphenyl)-2-[4-(methylcarbamoyl) cinnamoylaminomethyl]pyrrole with 2-methoxy-1-methyl-4-hydroxy-1H-benzimidazole according to a similar manner to that of Example 1-(7).

Example 9

1-[2,4-Dichloro-3-(2-methylquinazolin-8-yloxymethyl) phenyl]-2-[4-(methylcarbamoyl)cinnamoylaminomethyl] pyrrole is obtained by reacting 1-(2,4-dichloro-3-chloromethylphenyl)-2-[4-(methylcarbamoyl) cinnamoylaminomethyl]pyrrole with 2-methyl-8-hydroxyquinazoline according to a similar manner to that of Example 1-(7).

Example 10

1-[2,4-Dichloro-3-(2-methylquinoxalin-8-yloxymethyl) phenyl]-2-[4-(methylcarbamoyl)cinnamoylaminomethyl] pyrrole is obtained by reacting 1-(2,4-dichloro-3-chloromethylphenyl)-2-[4-(methylcarbamoyl) cinnamoylaminomethyl]pyrrole with 2-methyl-8-hydroxyquinoxaline according to a similar manner to that of Example 1-(7).

Example 11

1-[2,4-Dichloro-3-(2,3-dimethylbenzofuran-7-yloxymethyl)phenyl]-2-[4-(methylcarbamoyl) cinnamoylaminomethyl]pyrrole is obtained by reacting 1-(2,4-dichloro-3-chloromethylphenyl)-2-[4-(methylcarbamoyl) cinnamoylaminomethyl]pyrrole with 2,3-dimethyl-7-hydroxybenzofurane according to a similar manner to that of Example 1-(7).

Example 12

1-[2,4-Dichloro-3-(2-methylbenzoxazol-4-yloxymethyl) phenyl]-2-[4-(methylcarbamoyl)cinnamoylaminomethyl] pyrrole is obtained by reacting 1-(2,4-dichloro-3-chloromethylphenyl)-2-[4-(methylcarbamoyl) cinnamoylaminomethyl]pyrrole with 2-methyl-4-hydroxybenzoxazole according to a similar manner to that of Example 1-(7).

Example 13

(1) 1-[3-(3-Bromo-2-methylimidazo[1,2-]pyridin-8-yloxymethyl)-2,4-dichlorophenyl]pyrrole is obtained by reacting 8-(3-amino-2,6-dichlorobenzyloxy)-3-bromo-2-methylimidazo[1,2-a]pyridine with 2,5-dimethoxytetrahydrofuran according to a similar manner to that of Example 1-(1).
(2) 1-[3-(3-Bromo-2-methylimidazo[1,2-a]pyridin-8-yloxymethyl)-2,4-dichlorophenyl]-2-cyanopyrrole is obtained according to a similar manner to that of Example 1-(2).
(3) 2-Aminomethyl-1-[3-(3-bromo-2-methylimidazo[1,2-a]-pyridin-8-yloxymethyl)-2,4-dichlorophenyl]pyrrole is obtained according to a similar manner to that of Example 1-(3).
(4) 1-[3-(3-Bromo-2-methylimidazo[1,2-a]pyridin-8-yloxymethyl)-2,4-dichlorophenyl]-2-[4-(dimethylcarbamoyl)cinnamoylaminomethyl]pyrrole is obtained according to a similar manner to that of Example 2-(4).

Example 14

(1) 1-[2,4-Dimethyl-3-(2-methylquinolin-8-yloxymethyl) phenyl]pyrrole is obtained by reacting 8-(3-amino-2,6- dimethylbenzyloxy)-2-methylquinoline with 2,5-dimethoxytetrahydrofuran according to a similar manner to that of Example 1-(1).

(2) 1-[2,4-Dimethyl-3-(2-methylquinolin-8-yloxymethyl) phenyl]-2-cyanopyrrole is obtained according to a similar manner to that of Example 1-(2).

(3) 2-Aminomethyl-1-[2,4-dimethyl-3-(2-methylquinolin-8-yloxymethyl)phenyl]pyrrole is obtained according to a similar manner to that of Example 1-(3).

(4) 2-[(E)-3-(6-Acetamidopyridin-3-yl) acryloylaminomethyl]-1-[2,4-dimethyl-3-(2-methylquinolin-8-yloxymethyl)phenyl]pyrrole is obtained according to a similar manner to that of Example 2-(4).

Preparation 7

The solution of 4-chloro-8-hydroxy-2-methylquinoline (2.0 g), imidazole (3.52 g) in dioxane (20 ml) was refluxed for 18 hours. The cooled reaction mixture was added chloroform and aqueous sodium bicarbonate solution. The organic layer was washed with water, dried over magnesium sulfate and evaporated in vacuo. The residue was crystallized from ether to give 8-hydroxy-4-(imidazol-1-yl)-2-methylquinoline (1.99 g) as colorless crystals.

mp: 192–196° C.; NMR (CDCl$_3$, δ): 2.79 (3H, s), 7.20–7.37 (5H, m), 7.45 (1H, t, J=7.5 Hz), 7.86 (1H, s).

Preparation 8

8-Hydroxy-2-methyl-4-(pyrazol-1-yl)quinoline was obtained by reacting 4-chloro-8-hydroxy-2-methylquinoline with pyrazole according to a similar manner to that of Preparation 7.

mp: 53–54° C.; NMR (CDCl$_3$, δ): 2.78 (3H, s), 6.60 (1H, d, J=3 Hz), 7.20 (1H, d, J=8 Hz), 7.44 (1H, t, J=8 Hz), 7.46 (1H, s), 7.64 (1H, d, J=8 Hz), 7.79 (1H, br s), 7.98 (1H, d, J=3 Hz).

Preparation 9

(1) A mixture of 8-hydroxy-2-methylimidazo[1,2-a] pyridine (10 g), acetic anhydride (10.3 g) and pyridine (10.7 g) in anhydrous dichloromethane (100 ml) was stirred for 1 hour at ambient temperature and allowed to stand overnight. The mixture was washed with water, and the organic layer was separated. The aqueous layer was neutralized with sodium bicarbonate and extracted with chloroform. The combined organic layers were washed with saturated sodium bicarbonate solution, dried over magnesium sulfate and evaporated in vacuo to give 8-acetoxy-2-methylimidazo[1,2-a]pyridine (13.1 g) as oil.

(2) To a solution of 8-acetoxy-2-methylimidazo[1,2-a] pyridine (100 mg) in ethanol (1 ml) was added N-bromosuccinimide (103 mg) under ice-cooling, and the mixture was stirred for 30 minutes at the same temperature. The mixture was diluted with ethyl acetate and washed with saturated sodium bicarbonate solution, dried over magnesium sulfate and evaporated in vacuo. The residue was purified by preparative thin layer chromatography (ethyl acetate) to give 8-acetoxy-3-bromo-2-methylimidazo[1,2-a] pyridine (123 mg) as oil.

NMR (CDCl$_3$, δ): 2.46 (3H, s), 2.48 (3H, s), 6.88 (1H, t, J=8 Hz), 7.06 (1H, d, J=8 Hz), 7.97 (1H, d, J=8 Hz).

(3) To a solution of 8-acetoxy-3-bromo-2-methylimidazo [1,2-a]pyridine (235 mg) in methanol (2.5 ml) was added 1N sodium hydroxide solution (2.0 ml) under ice-cooling, and the mixture was stirred for 30 minutes at the same temperature. The mixture was neutralized with 1N hydrochloric acid, and the resulting precipitates were collected by filtration and washed with water to give 3-bromo-8-hydroxy-2-methylimidazo[1,2-a]pyridine (150 mg) as brown powder.

NMR (CDCl$_3$, δ): 2.47 (3H, s), 6.80 (1H, d, J=8 Hz), 6.88 (1H, t, J=8 Hz), 7.18 (1H, d, J=8 Hz).

Preparation 10

(1) 2-[(E)-3-(6-Acetamidopyridin-3-yl) acryloylaminomethyl]-1-(3-tert-butyldiphenylsilyloxymethyl-2,4-dichlorophenyl)pyrrole was obtained from 2-aminomethyl-1-(3-tert-butyldiphenylsilyloxymethyl-2,4-dichlorophenyl)pyrrole and (E)-3-(6-acetamidopyridin-3-yl)acrylic acid according to a similar manner to that of Example 1-(4).

NMR (DMSO-d$_6$, δ): 0.98 (9H, s), 2.10 (2H, s), 2.15 (1H, s), 4.03 (1H, dd, J=15, 6 Hz), 4.22 (1H, dd, J=15, 6 Hz), 4.89 (2H, s), 6.16–6.22 (2H), 6.52 (1H, d, J=15 Hz), 6.76 (1H, d, J=2 Hz), 7.17–8.49 (17H), 8.80 (1H, br s).

(2) 2-[(E)-3-(6-Acetamidopyridin-3-yl) acryloylaminomethyl]-1-(2,4-dichloro-3-hydroxymethylphenyl)pyrrole was obtained according to a similar manner to that of Example 1-(5).

NMR (DMSO-d$_6$, δ): 2.12 (3H, s), 4.04 (1H, dd, J=15, 6 Hz), 4.19 (1H, dd, J=15, 6 Hz), 4.72 (2H, d, J=6 Hz), 5.30 (1H, t, J=6 Hz), 6.17–6.22 (2H), 6.56 (1H, d, J=15 Hz), 6.76 (1H, d, J=3 Hz), 7,29 (1H, d, J=15 Hz), 7.45 (1H, d, J=8 Hz), 7.57 (1H, d, J=8 Hz), 7.89–8.26 (4H), 8.43 (1H, br s).

(3) 2-[(E)-3-(6-Acetamidopyridin-3-yl) acryloylaminomethyl]-1-[2,4-dichloro-3-(methanesulfonyloxymethyl)phenyl]pyrrole was obtained according to a similar manner to that of Example 24-(3).

NMR (CDCl$_3$, δ): 2.23 (3H, s), 3.08 (3H, s), 4.29 (1H, dd, J=15, 6 Hz), 4.41 (1H, dd, J=15, 6 Hz), 5.49–5.70 (3H), 6.25 (1H, d, J=15 Hz), 6.29–6.36(2H), 6.68 (1H, d, J=2 Hz) 7.22–7.50 (3H), 7.82 (1H, dd, J=8, 2 Hz), 8.22 (1H, d, J=8 Hz), 8.35 (1H, d, J=2 Hz).

Example 15

1-[2,4-Dichloro-3-(2-methylquinolin-8-yloxymethyl) phenyl]-2-[(E)-3-[6-[(E)-2-(pyridin-4-yl)vinyl]pyridin-3-yl] acryloylaminomethyl]pyrrole was obtained from 2-aminomethyl-1-[2,4-dichloro-3-(2-methylquinolin-8-yloxymethyl)phenyl]pyrrole and (E)-3-[6-[(E)-2-(pyridin-4-yl)vinyl]pyridin-3-yl]acrylic acid according to a similar manner to that of Example 2-(4).

NMR (CDCl$_3$, δ): 2.63 (3H, s), 4.27–4.39 (1H, m), 4.44–4.55 (1H, m), 5.55–5.66 (2H, m), 6.25–6.31(1H, m), 6.35 (1H, br s), 6.45 (1H, d, J=16 Hz), 6.58 (1H, t-like), 6.65–6.70 (1H, m), 7.02 (1H, d, J=8 Hz), 7.17–7.27 (3H, m), 7.35–7.57 (9H, m), 8.03 (1H, d, J=8 Hz), 8.50–8.55 (1H, m), 8.60 (2H, d, J=6 Hz).

its trihydrochloride

NMR (DMSO-d$_6$, δ): 2.81 (3H, s), 4.17–4.45 (2H, m), 5.49–5.65 (2H, m), 6.19–6.30 (2H, m), 6.72 (1H, d, J=16 Hz), 6.83–6.88 (1H, m), 7.40 (1H, d, J=16 Hz), 7.60 (1H, d, J=8 Hz), 7.64–7.83 (7H, m), 7.87 (1H, d, J=16 Hz), 8.00 (1H, d, J=16 Hz), 8.04 (1H, dd, J=2, 8 Hz), 8.23 (2H, d, J=6 Hz), 8.51 (1H, t-like), 8.79–8.89 (3H, m).

Example 16

(1) 1-[2,4-Dichloro-3-(2-methylquinolin-8-yloxymethyl) phenyl]-2-[(E)-3-(6-ethoxycarbonylpyridin-3-yl) acryloylaminomethyl]pyrrole was obtained from 2-aminomethyl-1-[2,4-dichloro-3-(2-methylquinolin-8-yloxymethyl)phenyl]pyrrole and (E)-3-(6-ethoxycarbonylpyridin-3-yl)acrylic acid according to a similar manner to that of Example 2-(4).

NMR (CDCl$_3$, δ): 1.43 (3H, t, J=7.5 Hz), 2.61 (3H, s), 4.41–4.53 (4H, m), 5.54 (1H, d, J=10 Hz), 5.62 (1H, d, J=10 Hz), 6.27–6.30 (1H, m), 6.31–6.35 (1H, m), 6.45 (1H, t-like), 6.59 (1H, d, J=16 Hz), 6.66–6.70 (1H, m), 7.19–7.30 (1H, m), 7.39 (1H, d, J=8 Hz), 7.42–7.54 (4H, m), 7.60 (1H, dd, J=2, 8 Hz), 7.76 (1H, d, J=8 Hz), 8.04 (1H, d, J=8 Hz), 8.67 (1H, d, J=2 Hz).

(2) To a suspension of 1-[2,4-dichloro-3-(2-methylquinolin-8-yloxymethyl)phenyl]-2-[(E)-3-(6-ethoxycarbonylpyridin-3-yl)acryloylaminomethyl]pyrrole (116 mg) in ethanol was added 1N sodium hydroxide solution (0.3 ml) at ambient temperature, and the mixture was stirred at 50° C. for 2 hours. The solvent was removed in vacuo, and the residue was dissolved in water. The aqueous solution was washed with diethyl ether and adjusted to pH 5 with 1N hydrochloric acid. The resulting precipitates were collected by filtration and washed with water and diethyl ether to give 2-[(E)-3-(6-carboxypyridin-3-yl) acryloylaminomethyl]-1-[2,4-dichloro-3-(2-methylquinolin-8-yloxymethyl)phenyl]pyrrole (77 mg) as amorphous powder.

NMR (DMSO-$d_6$, δ): 2.60 (3H, s), 2.08–4.21 (1H, m), 4.21–4.32 (1H, m), 5.43 (2H, s), 6.18–6.27 (2H, m), 6.80 (1H, d, J=16 Hz), 6.86–6.90 (1H, m), 7.27 (1H, d, J=8 Hz), 7.37–7.49 (3H, m), 7.53 (1H, d, J=8 Hz), 7.62 (1H, d, J=8 Hz), 7.72 (1H, d, J=8 Hz), 8.02–8.14 (2H, m), 8.21 (1H, d, J=8 Hz), 8.41 (1H, t-like), 8.85 (1H, d, J=2 Hz).

To a suspension of 2-[(E)-3-(6-carboxypyridin-3-yl) acryloylaminomethyl]-1-[2,4-dichloro-3-(2-methylquinolin-8-yloxymethyl)phenyl]pyrrole (60 mg) in water (1.5 ml) was added 1N sodium hydroxide solution (0.1 ml) at ambient temperature, and the mixture was lyophilized to give the sodium salt of 2-[(E)-3-(6-carboxypyridin-3-yl) acryloylaminomethyl]-1-[2,4-dichloro-3-(2-methylquinolin-8-yloxymethyl)phenyl]pyrrole (46 mg) as amorphous powder.

NMR ($D_2O$, δ): 2.57 (3H, s), 4.19–4.32 (1H, m), 4.38–4.51 (1H, m), 5.15–5.56 (2H, m), 6.30–6.47 (3H, m), 6.84–6.92 (1H, m), 7.05–7.19 (2H, m), 7.24–7.70 (7H, m), 7.96–8.10 (1H, m), 8.24 (1H, s-like).

(3) To a solution of 2-[(E)-3-(6-carboxypyridin-3-yl) acryloylaminomethyl]-1-[2,4-dichloro-3-(2-methylquinolin-8-yloxymethyl)phenyl]pyrrole (60 mg) and methylamine hydrochloride (7.59 mg) in N,N-dimethylformamide (2 ml) were added 1-ethyl-3-(3-dimethylaminopropyl)carbodiimide (19 mg) and 1-hydroxybenzotriazole (20.7 mg) at ambient temperature, and the mixture was allowed to stand for 1 day at the same temperature. The reaction mixture was poured into water and extracted with chloroform. The extract was washed with water and saturated sodium bicarbonate solution, dried over magnesium sulfate and evaporated in vacuo. The residue was purified by preparative thin layer chromatography (chloroform:methanol=10:1, V/V) to give 1-[2,4-dichloro-3-(2-methylquinolin-8-yloxymethyl)phenyl]-2-[(E)-3-[6-(methylcarbamoyl)pyridin-3-yl]acryloylaminomethyl] pyrrole (58 mg) as amorphous powder.

NMR (CDCl$_3$, δ): 2.60 (3H, s), 3.00 (3H, d, J=6 Hz), 4.34 (1H, dd, J=4, 15 Hz), 4.52 (1H, dd, J=4, 15 Hz), 5.54 (1H, d, J=10 Hz), 5.61 (1H, d, J=10 Hz), 6.25–6.31 (1H, m), 6.31–6.39 (1H, m), 6.47–6.61 (2H, m), 6.66–6.71 (1H, m), 7.18–7.31 (2H, m), 7.36–7.58 (6H, m), 7.78 (1H, d, J=8 Hz), 7.81–7.91 (1H, m), 8.04 (1H, d, J=8 Hz), 8.39 (1H, s-like).
its dihydrochloride NMR (DMSO-$d_6$, δ): 2.81 (3H, d, J=6 Hz), 2.90 (3H, s), 4.14–4.28 (1H, m), 4.40–4.60 (1H,m, overlapped with H$_2$O), 5.56 (1H, d, J=10 Hz), 5.65 (1H, d, J=10 Hz), 6.20–6.25 (1H, m), 6.25–6.29 (1H, m), 6.73 (1H, d, J=16 Hz), 6.83–6.86 (1H, m), 7.41(1H, d, J=16 Hz), 7.60 (1H, d, J=8 Hz), 7.69 (1H, d, J=8 Hz), 7.79–7.93 (3H, m), 7.96 (1H, br d), 8.03 (1H, d, J=8 Hz), 8.08 (1H, dd, J=8, 2 Hz), 8.58 (1H, t-like), 8.73 (1H, s-like), 8.77 (1H, q-like), 9.01 (1H, br peak).

Example 17

2-[(E)-3-(6-Carbamoylpyridin-3-yl) acryloylaminomethyl]-1-[2,4-dichloro-3-(2-methylquinolin-8-yloxymethyl)phenyl]pyrrole was obtained from 2-[(E)-3-(6-carboxypyridin-3-yl) acryloylaminomethyl]-1-[2,4-dichloro-3-(2-methylquinolin-8-yloxymethyl)phenyl]pyrrole and conc. ammonia solution according to a similar manner to that of Example 16-(3).

NMR (DMSO-$d_6$, δ): 2.60 (3H, s), 4.13 (1H, dd, J=4, 16 Hz), 4.27 (1H, dd, J=4, 16 Hz), 5.43 (2H, s), 6.18–6.26 (2H, m), 6.77 (1H, d, J=16 Hz), 6.84–6.90 (1H, m), 7.24 (1H, d, J=8 Hz), 7.37–7.56 (4H, m), 7.62 (1H, d, J=8 Hz), 7.64–7.74 (2H, m), 8.05 (1H, d, J=8 Hz), 8.08–8.18 (2H, m), 8.20 (1H, d, J=8 Hz), 8.38 (1H, t-like), 8.77 (1H, s).
its dihydrochloride NMR (DMSO-$d_6$, δ): 2.90 (3H, s), 4.21 (1H, d, J=15 Hz), 4.50 (1H, dd, J=6, 15 Hz), 5.57 (1H, d, J=10 Hz), 5.66 (1H, d, J=10 Hz), 6.20–6.25 (1H, m), 5.26–6.30 (1H, m), 6.73 (1H, d, J=16 Hz), 6.83–6.87 (1H, m), 7.40 (1H, d, J=16 Hz), 7.59 (1H, d, J=8 Hz), 7.65–7.74 (2H, m), 7.80–7.94 (3H, m), 7.98 (1H, d, J=8 Hz), 8.03–8.16 (3H, m), 8.59 (1H, t-like), 8.73 (1H, s-like), 8.97–9.08 (1H, m).

Example 18

(1) To a mixture of 1-(3-tert-butyldiphenylsilyloxymethyl-2,4-dichlorophenyl)-2-cyanopyrrole (900 mg) and silicic acid (100 mg) in carbon tetrachloride (15 ml) was added a solution of tert-butyl hypochlorite (222 mg) in carbon tetrachloride (10 ml) in water bath, and the mixture was stirred for 30 minutes at the same temperature. The reaction mixture was filtered, and the filtrate was evaporated in vacuo. The residue was purified by silica gel column chromatography eluting with a mixture of n-hexane and ethyl acetate (15:1, V/V) to give 1-(3-tert-butyldiphenylsilyloxymethyl-2,4-dichlorophenyl)-4-chloro-2-cyanopyrrole (290 mg) as an oil.

NMR (CDCl$_3$, δ): 1.07 (9H, s), 4.98 (2H, s), 6.90 (2H, s), 7.30 (1H, d, J=8 Hz), 7.36–7.52 (7H, m), 7.75 (4H, d-like).

(2) 2-Aminomethyl-1-(3-tert-butyldiphenylsilyloxymethyl-2,4-dichlorophenyl)-4-chloropyrrole was obtained according to a similar manner to that of Example 1-(3).

NMR (CDCl$_3$, δ): 3.43 (1H, br d, J=15 Hz), 3.57 (1H, br d, J=15 Hz), 4.55 (2H, s), 6.16 (1H, s-like), 6.56 (1H, d, J=2 Hz), 7.26 (1H, d, J=8 Hz), 7.33–7.48 (7H, m), 7.72 (4H, d-like).

(3) 1-(3-tert-Butyldiphenylsilyloxymethyl-2,4-dichlorophenyl)-2-[4-(methylcarbamoyl) cinnamoylaminomethyl]-4-chloropyrrole was obtained according to a similar manner to that of Example 1-(4).

NMR (CDCl$_3$, δ): 1.03 (9H, s), 3.02 (3H, d, J=6 Hz), 4.24 (2H, d, J=6 Hz), 4.87 (2H, s), 5.60 (1H, t-like), 6.07 (1H, br peak), 6.20–6.29 (2H, m), 6.63 (1H, d, J=2 Hz), 7.21–7.27 (1H, m), 7.30–7.51 (10H, m), 7.64–7.73 (6H, m).

(4) 4-Chloro-1-(2,4-dichloro-3-hydroxymethylphenyl)-2-[4-(methylcarbamoyl)cinnamoylaminomethyl]pyrrole was obtained according to a similar-manner to that of Example 1-(5).

NMR (DMSO-$d_6$, δ): 2.78 (3H, d, J=6 Hz), 3.94–4.06 (1H, m), 4.06–4.18 (1H, m), 4.20 (2H, d, J=6 Hz), 5.33 (1H, t-like), 6.24 (1H, d, J=2 Hz), 6.61 (1H, d, J=16 Hz), 6.98 (1H, d, J=2 Hz), 7.34 (1H, d, J=16 Hz), 7.48(1H, d, J=8 Hz), 7.55–7.63 (3H, m), 7.85 (2H, d, J=8 Hz), 8.32 (1H, t-like), 8.46 (1H, q-like).

(5) 4-Chloro-1-(2,4-dichloro-3-chloromethylphenyl)-2-[4-(methylcarbamoyl)cinnamoylaminomethyl]pyrrole was obtained according to a similar manner to that of Example 1-(6).

NMR (CDCl$_3$—CD$_3$OD, δ): 3.00 (3H, s), 4.22 (1H, d, J=15 Hz), 4.31 (1H, d, J=15 Hz), 4.85 (2H, s), 6.27 (1H, s-like), 6.34 (1H, d, J=16 Hz), 6.64 (1H, d, J=2 Hz), 7.33 (1H, d, J=8 Hz), 7.41–7.56 (4H, m), 7.74 (2H, d, J=8 Hz).

(6) 4-Chloro-1-[2,4-dichloro-3-(2-methylquinolin-8-yloxymethyl)phenyl]-2-[4-(methylcarbamoyl)cinnamoylaminomethyl]pyrrole was obtained according to a similar manner to that of Example 1-(7).

NMR (CDCl$_3$, δ): 2.61 (3H, s), 3.96 (3H, d, J=6 Hz), 4.22 (1H, dd, J=4, 16 Hz), 4.38 (1H, dd, J=4, 16 Hz), 5.49 (1H, d, J=10 Hz), 5.56 (1H, d, J=10 Hz), 6.28 (1H, s-like), 6.33 (1H, br peak), 6.38 (1H, d, J=16 Hz), 6.53 (1H, t-like), 6.60–6.63 (1H, m), 7.16 (1H, d, J=8 Hz), 7.20–7.33 (4H, m), 7.36–7.51 (4H, m), 7.55 (2H, d, J=8 Hz), 8.02 (1H, d, J=8 Hz).

its hydrochloride

NMR (DMSO-d$_6$, δ): 2.74–2.87 (6H, m), 4.11–4.22 (1H, m), 4.30 (1H, br peak), 5.45–5.62 (2H, m), 2.28–6.33 (1H, m), 6.60 (1H, d, J=16 Hz), 7.06 (1H, s-like), 7.34 (1H, d, J=16 Hz), 7.54–7.96 (10H, m), 8.33 (1H, s), 8.45–8.66 (2H, m).

Example 19

(1) To a solution of 1-(3-tert-butyldiphenylsilyloxymethyl-2,4-dichlorophenyl)pyrrole (1.0 g) in tetrahydrofuran (10 ml) was added N-chlorosuccinimide (292 mg) at ambient temperature, and the mixture was allowed to stand for 1 day. The reaction mixture was poured into water and extracted with ethyl acetate. The organic layer was washed with water and brine, dried over magnesium sulfate and evaporated in vacuo. The residue was chromatographed on silica gel eluting with a mixture of n-hexane and ethyl acetate (10:1, V/V) to give 1-(3-tert-butyldiphenylsilyloxymethyl-2,4-dichlorophenyl)-2-chloropyrrole (1.0 g) as an oil.

NMR (CDCl$_3$, δ): 1.04 (9H, s), 4.48 (2H, s), 6.17–6.23 (1H, m), 6.26–6.31 (1H, m), 6.63–6.69 (1H, m), 7.20–7.27 (1H, m), 7.33–7.49 (7H, m), 7.69–7.79 (4H, m).

(2) 1-(3-tert-Butyldiphenylsilyloxymethyl-2,4-dichlorophenyl)-5-chloro-2-cyanopyrrole was obtained according to a similar manner to that of Example 1-(2).

NMR (CDCl$_3$, δ): 1.05 (9H, s), 4.98 (2H, s-like), 6.30 (1H, d, J=4 Hz), 6.95 (1H, d, J=4 Hz), 7.30 (1H, d, J=8 Hz), 7.35–7.50 (7H, m), 7.73 (4H, d-like).

(3) 2-Aminomethyl-1-(3-tert-butyldiphenylsilyloxymethyl-2,4-dichlorophenyl)-5-chloropyrrole was obtained according to a similar manner to that of Example 1-(3).

NMR (CDCl$_3$, δ): 1.04 (9H, s), 3.45 (1H, d, J=15 Hz), 3.55 (1H, d, J=15 Hz), 4.94 (2H, s), 6.12–6.20 (2H, m), 7.27 (1H, d, J=8 Hz), 7.32–7.48 (7H, m), 7.72 (4H, d-like).

(4) 1-(3-tert-Butyldiphenylsilyloxymethyl-2,4-dichlorophenyl)-2-[4-(methylcarbamoyl)cinnamoylaminomethyl]-5-chloropyrrole was obtained according to a similar manner to that of Example 1-(4).

NMR (CDCl$_3$, δ): 1.00 (9H, s), 3.02 (3H, d, J=6 Hz), 4.26 (2H, d, J=6 Hz), 4.83 (1H, d, J=10 Hz), 4.90 (1H, d, J=10 Hz), 5.60 (1H, t-like), 6.08 (1H, q-like), 6.16–6.29 (3H, m), 7.23–7.30 (1H, m), 7.30–7.50 (10H, m), 7.64–7.73 (6H, m).

(5) 5-Chloro-1-(2,4-dichloro-3-hydroxymethylphenyl)-2-[4-(methylcarbamoyl)cinnamoylaminomethyl]pyrrole was obtained according to a similar manner to that of Example 1-(5).

NMR (DMSO-d$_6$, δ): 2.78 (3H, d, J=6 Hz), 3.97 (1H, dd, J=4, 15 Hz), 4.16 (1H, dd, J=4, 15 Hz), 4.68 (2H, d, J=7 Hz), 5.35 (1H, t-like), 6.26 (2H, s-like), 6.61 (1H, d, J=16 Hz), 7.31 (1H, d, J=16 Hz), 7.49 (1H, d, J=8 Hz), 7.55–7.65 (3H, m), 7.85 (2H, d, J=8 Hz), 8.27 (1H, t-like), 8.48 (1H, q-like).

(6) 5-Chloro-1-(2,4-dichloro-3-chloromethylphenyl)-2-[4-(methylcarbamoyl)cinnamoylaminomethyl]pyrrole was obtained according to a similar manner to that of Example 1-(6).

NMR (CDCl$_3$—CD$_3$OD, δ): 3.00 (3H, s), 4.21 (1H, d, J=16 Hz), 4.35 (1H, d, J=16 Hz), 4.84 (2H, s), 6.11 (1H, t-like), 6.18 (1H, d, J=4 Hz), 6.28 (1H, d, J=4 Hz), 6.31 (1H, d, J=16 Hz), 6.60 (1H, q-like), 7.32 (1H, d, J=8 Hz), 7.41–7.54 (4H, m), 7.74 (2H, d, J=8 Hz).

(7) 5-Chloro-1-[2,4-dichloro-3-(2-methylquinolin-8-yloxymethyl)phenyl]-2-[4-(methylcarbamoyl)cinnamoylaminomethyl]pyrrole was obtained according to a similar manner to that of Example 1-(7).

NMR (CDCl$_3$, δ): 2.55 (3H, s), 2.98 (3H, d, J=6 Hz), 3.90 (1H, dd, J=7, 15 Hz), 4.65 (1H, dd, J=7, 15 Hz), 5.52 (1H, d, J=10 Hz), 5.61 (1H, d, J=10 Hz), 6.07 (1H, br peak), 6.14 (1H, d, J=4 Hz), 6.35 (1H, d, J=16 Hz), 6.41 (1H, d, J=4 Hz), 6.98 (2H, d, J=8 Hz), 7.18–7.25 (4H, m), 7.37–7.53 (4H, m), 7.58 (1H, d, J=8 Hz), 7.83 (1H, t-like), 8.13 (1H, d, J=8 Hz).

its hydrochloride

NMR (DMSO-d$_6$, δ): 2.80 (3H, d, J=6 Hz), 2.85 (3H, s), 4.19 (1H, dd, J=4, 15 Hz), 4.24–4.38 (1H, m), 5.49 (1H, d, J=10 Hz), 5.60 (1H, d, J=10 Hz), 6.25–6.33 (2H, m), 6.61 (1H, d, J=16 Hz), 7.33 (1H, d, J=16 Hz), 7.50–7.68 (4H, m), 7.74 (2H, d, J=8 Hz), 7.78–7.93 (4H, m), 8.40–8.56 (3H, m).

Example 20

(1) 1-(3-tert-Butyldiphenylsilyloxymethyl-4-chlorophenyl)pyrrole was obtained by reacting 3-(tert-butyldiphenylsilyloxymethyl)-4-chloroaniline with 2,5-dimethoxytetrahydrofuran according to a similar manner to that of Example 1-(1).

NMR (CDCl$_3$, δ): 1.14 (9H, s), 4.85 (2H, s), 6.35–6.40 (2H, m), 7.07–7.12 (2H, m), 7.21 (1H, dd, J=8, 2 Hz), 7.31 (1H, d, J=8 Hz), 7.34–7.49 (6H, m), 7.70 (4H, d-like), 7.82 (1H, d, J=2 Hz).

(2) 1-(3-tert-Butyldiphenylsilyloxymethyl-4-chlorophenyl)-2-cyanopyrrole was obtained according to a similar manner to that of Example 1-(2).

NMR (CDCl$_3$, δ): 1.13 (9H, s), 4.84 (2H, s), 6.34–6.40 (1H, m), 7.00–7.04 (1H, m), 7.04–7.08 (1H, m), 7.28–7.50 (8H, m), 7.63–7.74 (4H, m), 7.78–7.84 (1H, m).

(3) 2-Aminomethyl-1-(3-tert-butyldiphenylsilyloxymethyl-4-chlorophenyl)pyrrole was obtained according to a similar manner to that of Example 1-(3).

NMR (CDCl$_3$, δ): 1.10 (9H, s), 3.85 (2H, s), 4.85 (2H, s), 6.21–6.30 (2H, m), 6.77–6.83 (1H, m), 7.21–7.29 (1H, m), 7.33–7.50 (7H, m), 7.69 (4H, d-like), 7.74–7.78 (1H, m).

(4) 1-(3-tert-Butyldiphenylsilyloxymethyl-4-chlorophenyl)-2-[4-(methylcarbamoyl)cinnamoylaminomethyl]pyrrole was obtained according to a similar manner to that of Example 1-(4).

NMR (CDCl$_3$, δ): 1.10 (9H, s), 3.01 (3H, d, J=6 Hz), 4.55 (2H, d, J=6 Hz), 4.83 (2H, s), 5.66 (1H, t-like), 6.13 (1H, q-like), 6.25–6.36 (3H, m), 6.80–6.85 (1H, m), 7.16 (1H, dd, J=8, 2 Hz), 7.33–7.50 (9H, m), 7.56 (1H, d, J=16 Hz), 7.63–7.75 (7H, m).

(5) 1-(4-Chloro-3-hydroxymethylphenyl)-2-[4-(methylcarbamoyl)cinnamoylaminomethyl]pyrrole was obtained according to a similar manner to that of Example 1-(5).

NMR (DMSO-d$_6$, δ): 2.78 (3H, d, J=6 Hz), 4.31 (2H, d, J=6 Hz), 4.58 (2H, d, J=6 Hz), 5.49 (1H, t-like), 6.17–6.24

(2H, m), 6.20 (1H, d, J=16 Hz), 6.89–6.94 (1H, m), 7.33 (1H, dd, J=8, 2 Hz), 7.41 (1H, d, J=16 Hz), 7.47–7.55 (2H, m), 7.61 (2H, d, J=8 Hz), 7.85 (2H, d, J=8 Hz), 8.40–8.51 (2H, m).

(6) 1-(4-Chloro-3-chloromethylphenyl)-2-[4-(methylcarbamoyl)cinnamoylaminomethyl]pyrrole was obtained according to a similar manner to that of Example 1-(6).

NMR (DMSO-$d_6$, δ): 2.78 (3H, d, J=6 Hz), 4.34 (2H, d, J=6 Hz), 6.83 (2H, s), 6.17–6.26 (2H, m), 6.69 (1H, d, J=16 Hz), 6.93–6.98 (1H, m), 7.36–7.48 (2H, m), 7.55–7.70 (4H, m), 7.84 (2H, d, J=8 Hz), 8.40–8.51 (2H, m).

(7) 1-[4-Chloro-3-(2-methylquinolin-8-yloxymethyl) phenyl]-2-[4-(methylcarbamoyl)cinnamoylaminomethyl] pyrrole NMR (CDCl$_3$—CD$_3$OD, δ): 2.71 (3H, s), 3.00 (3H, d, J=6 Hz), 4.38–4.44 (2H, m), 5.44 (2H, s), 6.15 (1H, d, J=16 Hz), 6.19–6.23 (1H, m), 6.26 (1H, br peak), 6.33–6.37 (1H, m), 6.74–6.78(1H, m), 6.91–7.00 (1H, m), 7.10 (1H, dd, J=2, 6 Hz), 7.18 (2H, d, J=8 Hz), 7.22–7.31 (2H, m), 7.34–7.52 (4H, m), 7.55 (2H, d, J=8 Hz), 7.92–7.95 (1H, m), 8.04 (1H, d, J=8 Hz).

its hydrochloride

NMR (DMSO-$d_6$, δ): 2.75 (3H, s), 2.90 (3H, s), 4.30 (2H, s), 5.55 (2H, s), 6.15–6.25 (2H, m), 6.60 (1H, d, J=16 Hz), 6.91–6.98 (1H, m), 7.27 (1H, d, J=16 Hz), 7.42–7.56 (3H, m), 7.56–7.95 (8H, m), 8.41–8.55 (2H, m), 8.84 (1H, br peak).

Example 21

A mixture of 4-hydroxy-2-methoxy-1-methyl-1H-benzimidazole (47.4 mg), 2-[(E)-3-(6-acetamidopyridin-3-yl)acryloylaminomethyl]-1-[2,4-dichloro-3-(methanesulfonyloxymethyl)phenyl]pyrrole (143 mg) and potassium carbonate (110 mg) in N,N-dimethylformamide (4 ml) was stirred at ambient temperature for 3.5 days. The mixture was partitioned between chloroform and water. The separated organic layer was dried over magnesium sulfate and evaporated in vacuo. The residue was purified by preparative thin layer chromatography (chloroform:methanol=9:1, V/V) to give 2-[(E)-3-(6-acetamidopyridin-3-yl)acryloylaminomethyl]-1-[2,4-dichloro-3-(2-methoxy-1-methyl-1H-benzimidazol-4-yloxymethyl)phenyl]pyrrole (39 mg) as colorless crystals.

mp: 233–240° C.; NMR (CDCl$_3$, δ): 2.22 (3H, s), 3.53 (3H, s), 4.11 (3H, s), 4.31 (1H, dd, J=15, 6 Hz), 4.46 (1H, dd, J=15, 6 Hz), 5.57 (2H, s), 6.11–6.38 (4H), 6.69 (1H, s-like), 6.78 (1H, d, J=8 Hz), 6.88 (1H, d, J=8 Hz), 7.12 (1H, t, J=8 Hz), 7.22–7.50 (3H), 7.64 (1H, dd, J=8 Hz), 8.00–8.26 (3H).

Example 22

2-[(E)-3-(6-Acetamidopyridin-3-yl) acryloylaminomethyl]-1-[2,4-dichloro-3-(3-bromo-2-methylimidazo[1,2-a]pyridin-8-yloxymethyl)phenyl] pyrrole was obtained from 3-bromo-8-hydroxy-2-methylimidazo[1,2-a]pyridine and 2-[(E)-3-(6-acetamidopyridin-3-yl)acryloylaminomethyl]-1-[2,4-dichloro-3-(methanesulfonyloxymethyl)phenyl]pyrrole according to a similar manner to that of Example 21.

mp: 236–238° C.; NMR (CDCl$_3$, δ): 2.21 (3H, s), 2.37 (3H, s), 4.24 (1H, dd, J=15 Hz), 4.49 (1H, dd, J=15 Hz), 5.42 (1H, d, J=12 Hz), 5.48 (1H, d, J=12 Hz), 6.22–6.38 (3H), 6.64–6.70 (2H), 6.86 (1H, t, J=8 Hz), 7.34–7.56 (4H), 7.79 (1H, d, J=8 Hz), 7.96 (1H, s), 8.19 (1H, s).

its dihydrochloride

NMR (DMSO-$d_6$, δ): 2.12 (3H, s), 2.40 (3H, s), 4.19 (2H, s-like), 5.59 (2H, s), 6.19–6.28 (2H), 6.59 (1H, d, J=16 Hz), 6.81 (1H, s), 7.30 (1H, d, J=16 Hz), 7.45 (1H, br s), 7.56–7.70 (2H), 7.75 (1H, d, J=8 Hz), 7.94 (1H, d, J=8 Hz), 8.10 (1H, d, J=8 Hz), 8.25–8.45 (3H).

Example 23

(1) 1-[3-(tert-Butyldiphenylsilyloxymethyl)-2,4-dichlorophenyl]-2-[(E)-3-[6-[(E)-2-(pyridin-4-yl)vinyl] pyridin-3-yl]acryloylaminomethyl]pyrrole was obtained from 1-[3-(tert-butyldiphenylsilyloxymethyl)-2,4-dichlorophenyl]-2-aminomethylpyrrole and (E)-3-[6-[(E)-2-(pyridin-4-yl)vinyl]pyridin-3-yl]acrylic acid according to a similar manner to that of Example 1-(4).

NMR (CDCl$_3$, δ): 1.02 (9H, s), 4.30–4.36 (2H, m), 4.90 (2H, s), 5.60 (1H, br s), 6.22–6.34 (3H, m), 6.69 (1H, br s), 7.24–7.52 (12H, m), 7.66–7.75 (5H, m), 8.59–8.69 (4H, m).

(2) 1-(2,4-Dichloro-3-hydroxymethylphenyl)-2-[(E)-3-[6-[(E)-2-(pyridin-4-yl)vinyl]pyridin-3-yl] acryloylaminomethyl]-pyrrole was obtained according to a similar manner to that of Example 1-(5).

NMR (CDCl$_3$—CD$_3$OD, δ): 4.30 (1H, br d, J=15 Hz), 4.48 (1H, br d, J=15 Hz), 4.96 (2H, s), 6.24–6.34 (2H, m), 6.37 (1H, d, J=15 Hz), 6.59 (1H, br t, J=5 Hz), 6.68 (1H, m), 7.22–7.33 (2H, m), 7.35–7.50 (5H, m), 7.58 (1H, d, J=15 Hz), 7.80 (1H, dd, J=8, 3 Hz), 8.58 (2H, d, J=7 Hz), 8.71 (1H, d, J=2 Hz).

(3) To a solution of 1-(2,4-dichloro-3-hydroxymethylphenyl)-2-[(E)-3-[6-[(E)-2-(pyridin-4-yl) vinyl]pyridin-3-yl]acryloylaminomethyl]pyrrole (70 mg) and triethylamine (28 mg) in N,N-dimethylformamide (1 ml) was added methanesulfonyl chloride (16.7 mg) under ice-cooling, and the mixture was stirred for 30 minutes at the same temperature. To the mixture were added 3-bromo-8-hydroxy-2-methylimidazo[1,2-a]pyridine (31.4 mg) and potassium carbonate (95.7 mg) at ambient temperature, and the mixture was stirred at the same temperature overnight. Water was added thereto, the resulting precipitates were collected by filtration. The residue was purified by preparative thin layer chromatography (chloroform:methanol=10:1, V/V) to give 1-(3-(3-bromo-2-methylimidazo[1,2-a] pyridin-8-yloxymethyl)-2,4-dichlorophenyl]-2-[(E)-3-[6-[(E)-2-(pyridin-4-yl)vinyl]pyridin-3-yl] acryloylaminomethyl]pyrrole (76 mg) as yellow amorphous.

NMR (CDCl$_3$, δ): 2.40 (3H, s), 4.29–4.49 (2H, m), 5.44 (2H, s), 5.98 (1H, br s), 6.27–6.35 (2H, m), 6.39 (1H, d, J=15 Hz), 6.60 (1H, br d, J=7.5 Hz), 6.70 (1H, m), 6.79 (1H, t, J=7.5 Hz), 7.28–7.49 (7H, m), 7.55 (1H, d, J=15 Hz)., 7.62–7.77 (2H, m), 8.59–8.69 (2H, m).

its trihydrochloride

NMR (CDCl$_3$—CD$_3$OD, δ): 2.65 (3H, s), 4.28 (1H, br d, J=15 Hz), 4.78 (1H, br d, J=15 Hz), 5.60 (1H, br d, J=10 Hz), 5.71 (1H, br d, J=10 Hz), 6.30 (1H, t, J=2 Hz), 6.49 (1H, d, J=2 Hz), 6.71 (1H, br s), 7.03 (1H, d, J=15 Hz), 7.25–7.35 (1H, overlapped with H$_2$O), 7.45–7.60 (4H, m), 8.08–8.19 (2H, m), 8.30–8.41 (3H, m), 8.51 (1H, br s), 8.79 (1H, br s), 8.85 (2H, br d, J=7 Hz), 9.05 (1H, br s).

Example 24

(1) To a mixture of 2-aminomethyl-1-(3-tert-butyldiphenylsilyloxymethyl-2,4-dichlorophenyl)pyrrole (87 mg) and pyridine (20.3 mg) in dichloromethane (1 ml) was added acetic anhydride (20.9 mg) under ice-cooling, and the mixture was stirred for 3 hours at ambient temperature. The mixture was poured into water and extracted with dichloromethane. The organic layer was washed with 1N hydrochloric acid, water, saturated sodium bicarbonate solution and brine, dried over magnesium sulfate and evaporated in vacuo to give 2-acetamidomethyl-1-(3-tert-butyldiphenylsilyloxymethyl-2,4-dichlorophenyl)pyrrole (94 mg) as amorphous powder.

NMR (CDCl$_3$, δ): 1.05 (9H, s), 2.79 (3H, s), 4.19 (2H, d, J=6 Hz), 4.94 (2H, s), 5.38 (1H, br peak), 6.23–6.30 (2H, m), 6.65 (1H, d, J=2 Hz), 7.17 (1H, d, J=8 Hz), 7.25 (1H, d, J=8 Hz), 7.34–7.49 (6H, m), 7.70–7.78 (4H, m).

(2) 2-Acetamidomethyl-1-(2,4-dichloro-3-hydroxymethylphenyl)pyrrole was obtained according to a similar manner to that of Example 1-(5).

NMR (CDCl$_3$, δ): 1.81 (3H, s), 2.65 (1H, br s), 4.25 (2H, t, J=6 Hz), 5.01 (2H, br s), 5.44 (1H, br s), 6.23–6.31 (2H, m), 6.89 (1H, br s), 7.25 (1H, d, J=8 Hz), 7.44 (1H, d, J=8 Hz).

(3) To a mixture of 2-acetamidomethyl-1-(2,4-dichloro-3-hydroxymethylphenyl)pyrrole (51 mg) and triethylamine (19.8 mg) in dichloromethane (2 ml) was added methanesulfonyl chloride (20.5 mg) under nitrogen atmosphere in ice-methanol bath, and the mixture was stirred for 2 hours at the same temperature. The reaction mixture was poured into water and extracted with chloroform. The extract was washed with water, saturated sodium bicarbonate solution and brine, dried over magensium sulfate and evaporated in vacuo to give 2-acetamidomethyl-1-[2,4-dichloro-3-(methanesulfonyloxymethyl)phenyl]pyrrole (64 mg) as oil.

NMR (CDCl$_3$, δ): 1.84 (3H, s), 3.12 (3H, s), 4.18–4.23 (2H, m), 5.58 (2H, s), 6.25–6.31 (2H, m), 6.63–6.69 (1H, m), 7.38 (1H, d, J=8 Hz), 7.50 (1H, d, J=8 Hz).

(4) 2-Acetamidomethyl-1-[2,4-dichloro-3-[4-(imidazol-1-yl)-2-methylquinolin-8-yloxymethyl]phenyl]pyrrole was obtained according to a similar manner to that of Example 21.

NMR (CDCl$_3$, δ): 1.85 (3H, s), 2.79 (3H, s), 4.24 (2H, d, J=6 Hz), 5.61 (1H, br peak), 5.67 (2H, s), 6.29 (1H, s-like), 6.65–6.72 (1H, m), 7.29–7.55 (8H, m), 7.83 (1H, s).

Example 25

2-Acetamidomethyl-1-[2,4-dichloro-3-[2-methyl-4-(pyrazol-1-yl)quinolin-8-yloxymethyl]phenyl]pyrrole was obtained from 8-hydroxy-2-methyl-4-(pyrazol-1-yl)quinoline and 2-acetamidomethyl-1-[2,4-dichloro-3-(methanesulfonyloxymethyl)phenyl]pyrrole according to a similar manner to that of Example 21.

NMR (CDCl$_3$, δ): 1.84 (3H, s), 2.78 (3H, s), 4.21 (2H, t, J=5 Hz), 5.62 (1H, br s), 5.18 (2H, s), 6.24–6.31 (2H, m), 6.59 (1H, br s), 6.68 (1H, d, J=2 Hz), 7.29–7.52 (5H, m), 7.75 (1H, d, J=8 Hz), 7.85–7.93 (3H, m).
its dihydrochloride NMR (CDCl$_3$—CD$_3$OD, δ): 1.98 (3H, br s), 3.19 (3H, br s), 4.15 (1H, br d, J=15 Hz), 4.73 (1H, br d, J=15 Hz), 5.65 (1H, br d, J=10 Hz), 5.71 (1H, br d, J=10 Hz), 6.26 (1H, s), 6.78 (1H, br s), 7.46 (1H, br d, J=8 Hz), 7.55–7.69 (2H, m), 7.87 (1H, br t, J=8 Hz), 8.05 (1H, br s), 8.13 (1H, br s), 8.53 (1H, br s), 8.61 (1H, br d, J=8 Hz).

Example 26

(1) 2-Butyramidomethyl-1-[2,4-dichloro-3-(tert-butyldiphenylsilyloxymethyl)phenyl]pyrrole was obtained by reacting 2-aminomethyl-1-[3-(tert-butyldiphenylsilyloxymethyl)-2,4-dichlorophenyl]pyrrole with butyric anhydride according to a similar manner to that of Example 24-(1).

NMR (CDCl$_3$, δ): 0.81 (3H, t, J=7 Hz), 1.70 (2H, q, J=7 Hz), 2.44 (2H, t, J=7 Hz), 4.94 (2H, s), 5.35 (1H, br peak), 6.22–6.30 (2H, m), 6.62–6.68 (1H, m), 7.24 (1H, d, J=8 Hz), 7.31–7.48 (7H, m), 7.68–7.80 (4H, m).

(2) 2-Butyramidomethyl-1-(2,4-dichloro-3-hydroxymethylphenyl)pyrrole was obtained according to a similar manner to that of Example 1-(5).

NMR (CDCl$_3$, δ): 0.87 (3H, t, J=7.5 Hz), 1.45–1.60 (2H, m), 1.93–2.04 (2H, m), 2.59 (1H, br t, J=6 Hz), 4.20 (1H, dd, J=15, 5 Hz), 4.31 (1H, dd, J=15, 5 Hz), 4.95–5.06 (2H, m), 5.49 (1H, br s), 6.22–6.31 (2H, m), 6.69 (1H, m), 7.23 (1H, d, J=8 Hz), 7.43 (1H, d, J=8 Hz).

(3) 2-Butyramidomethyl-1-[2,4-dichloro-3-(methanesulfonyloxymethyl)phenyl]pyrrole was obtained according to a similar manner to that of Example 24-(3).

(4) 2-Butyramidomethyl-1-[2,4-dichloro-3-[2-methyl-4-(pyrazol-1-yl)quinolin-8-yloxymethyl]phenyl]pyrrole was obtained according to a similar manner to that of Example 21.

NMR (CDCl$_3$, δ): 0.85 (3H, t, J=7.5 Hz), 1.49–1.64 (2H, m), 2.03 (2H, t, J=7.5 Hz), 2.79 (3H, s), 4.12–4.32 (2H, m), 5.54 (1H, br s), 5.68 (2H, s), 6.23–6.31 (2H, m), 6.60 (1H, m), 6.69 (1H, m), 7.30–7.37 (2H, m), 7.41 (1H, d, J=8 Hz), 7.45–7.53 (2H, m), 7.77 (1H, br d, J=8 Hz), 7.85–7.94 (2H, m).
its dihydrochloride NMR (CDCl$_3$—CD$_3$OD, δ): 0.78–0.88 (3H, m), 1.34–1.50 (2H, m), 1.89–2.13 (2H, m), 3.14 (3H, br s), 4.12 (1H, br d, J=15 Hz), 4.86 (1H, br d, J=15 Hz), 5.60 (1H, br d, J=10 Hz), 5.77 (1H, br d, J=10 Hz), 6.27 (1H, s), 6.79 (1H, br s), 7.41 (1H, br d, J=8 Hz), 7.56 (1H, br d, J=8 Hz), 7.65 (1H, br s), 7.87 (1H, br s), 8.04 (1H, br s), 8.30 (1H, br s), 8.65–8.75 (2H, m).

Example 27

(1) To a solution of 1-(3-tert-butyldiphenylsilyloxymethyl-2,4-dichlorophenyl)-2-cyanopyrrole (2.44 g) in dichloromethane (25 ml) was added diisobutylaluminum hydride (1.5 M solution in toluene, 4.9 ml) under nitrogen atmosphere in water bath, and the mixture was stirred for 30 minutes at the same temperature. The reaction mixture was cooled in ice water bath, and to the mixture were added dropwise methanol (1 ml) and water (1 ml). The mixture was stirred for 1 hour, quenched with 1N sodium hydroxide solution and extracted with chloroform. The organic layer was washed with a saturated aqueous sodium hydrogen carbonate solution and brine, dried over magnesium sulfate and evaporated in vacuo. The residue was chromatographed on silica gel eluting with a mixture of n-hexane and ethyl acetate (20:1, V/V) to give 1-(3-tert-butyldiphenylsilyloxymethyl-2,4-dichlorophenyl)-2-formylpyrrole (1.9 g) as an oil.

NMR (CDCl$_3$, δ): 1.06 (9H, s), 4.97 (2H, s), 6.42–6.48 (2H, m), 6.90–6.97 (1H, m), 7.09–7.11 (1H, m), 7.21–7.28 (1H, m), 7.32–7.48 (7H, m), 7.69–7.80 (4H, m), 9.50 (1H, s).

(2) 1-(2,4-Dichloro-3-hydroxymethylphenyl)-2-formylpyrrole was obtained according to a similar manner to that of Example 1-(5).

NMR (CDCl$_3$, δ): 2.15 (1H, t-like), 5.02 (2H, d, J=6 Hz), 6.43–6.50 (1H, m), 6.90–6.98 (1H, m), 7.09–7.15 (1H, m), 7.27 (1H, d, J=8 Hz), 7.45 (1H, d, J=8 Hz), 9.53 (1H, s).

(3) 1-(2,4-Dichloro-3-methanesulfonyloxymethylphenyl)-2-formylpyrrole was obtained according to a similar manner to that of Example 24-(3).

NMR (CDCl$_3$, δ): 3.09 (3H, s), 5.58 (2H, s), 6.46–6.51 (1H, m), 6.93–6.97 (1H, m), 7.10–7.15 (1H, m), 7.37 (1H, d, J=8 Hz), 7.49 (1H, d, J=8 Hz), 9.53 (1H, s).

(4) 1-[2,4-Dichloro-3-[2-methyl-4-(pyrazol-1-yl)quinolin-8-yloxymethyl]phenyl]-2-formylpyrrole was obtained according to a similar manner to that of Example 21.

NMR (CDCl$_3$, δ): 2.80 (3H, s), 5.65 (1H, d, J=10 Hz), 5.72 (1H, d, J=10 Hz), 6.43–6.48 (1H, m), 6.55–6.60 (1H, m), 6.95–7.00 (1H, m), 7.09–7.14 (1H, m), 7.29–7.50 (5H, m), 7.74 (1H, d, J=8 Hz), 7.84–7.92 (2H, m), 9.51 (1H, s).

Example 28

To a solution of 1-[2,4-dichloro-3-[2-methyl-4-(pyrazol-1-yl)quinolin-8-yloxymethyl]phenyl]-2-formylpyrrole (23 mg) in methanol (0.5 ml) was added sodium borohydride (1.91 mg) udner ice-cooling, and the mixture was stirred for 2 hours. To the mixture was dropwise added aqueous solution of ammonium chloride under ice-cooling, and the mixture was stirred for 1 hour. The mixture was concentrated in vacuo, and ethyl acetate and water were added thereto. The separated organic layer was washed with water and brine, dried over magnesium sulfate and evaporated in vacuo. The residue was purified by preparative thin layer chromatography (chloroform:methanol=20:1, V/V) to give 1-[2,4-dichloro-3-[2-methyl-4-(pyrazol-1-yl)quinolin-8-yloxymethyl]phenyl]-2-hydroxymethylpyrrole (11 mg) as amorphous powder.

NMR (CDCl$_3$—CD$_3$OD, δ): 2.77 (3H, s), 4.40 (2H, d, J=6 Hz), 5.60 (1H, br peak), 5.70 (1H, br peak), 6.24–6.30 (1H, m), 6.30–6.34 (1H, m), 6.57–6.62 (1H, m), 6.68–6.73 (1H, m), 7.33 (1H, d, J=8 Hz), 7.38–7.54 (4H, m), 7.74 (1H, d, J=8 Hz), 7.86–7.94 (2H, m).

Example 29

A mixture of 1-[2,4-dichloro-3-[2-methyl-4-(pyrazol-1-yl)quinolin-8-yloxymethyl]phenyl]-2-formylpyrrole (80 mg), hydroxylamine hydrochloride (18 mg), sodium acetate (21 mg) and ethanol (60% solution in water, 1.5 ml) was stirred at 60° C. for 1 hour. After cooling to ambient temperature, the reaction mixture was concentrated in vacuo. The residue was dissolved in ethyl acetate, washed with water and brine, dried over magnesium sulfate and evaporated in vacuo. The residue was purified by preparative thin-layer chromatography (n-hexane:ethyl acetate=1:1, V/V) to give 1-[2,4-dichloro-3-[2-methyl-4-(pyrazol-1-yl)quinolin-8-yloxymethyl]phenyl]-2-((E)-hydroxyiminomethyl)pyrrole (45 mg) as an amorphous powder and 1-[2,4-dichloro-3-[2-methyl-4-(pyrazol-1-yl)quinolin-8-yloxymethyl]phenyl]-2-((Z)-hydroxyiminomethyl)pyrrole (14 mg) as an amorphous powder.

1-[2,4-Dichloro-3-[2-methyl-4-(pyrazol-1-yl)quinolin-8-yloxymethyl]phenyl]-2-((E)-hydroxyiminomethyl)pyrrole NMR (CDCl$_3$, δ): 2.75 (3H, s), 5.55–5.66 (2H, m), 6.32–6.39 (1H, m), 6.50–6.56 (1H, m), 6.56–6.61 (1H, m), 6.77–7.81 (1H, m), 7.28–7.37 (2H, m), 7.40 (1H, s), 7.44–7.53 (2H, m), 7.74 (1H, d, J=8 Hz), 7.85–7.92 (3H, m), 9.00 (1H, s).

1-[2,4-Dichloro-3-[2-methyl-4-(pyrazol-1-yl)quinolin-8-yloxymethyl]phenyl]-2-((Z)-hydroxyiminomethyl)pyrrole NMR (CDCl$_3$, δ): 2.78 (3H, s), 5.70 (2H, s), 6.41–6.48 (1H, m), 6.55–6.61 (1H, m), 6.78–6.83 (1H, m), 6.83–6.88 (1H, m), 7.30–7.53 (7H, m), 7.75 (1H, d, J=8 Hz), 7.85–7.94 (2H, m).

Example 30

(1) 1-(3-tert-Butyldiphenylsilyloxymethyl-2,4-dichlorophenyl)-2-formylpyrrole (1.51 g) was dissolved in a mixture of water (8 ml) and tert-butyl alcohol (30 ml), and 2-methyl-2-butene (923 mg) and sodium dihydrogen phosphate (392 mg) were added to the mixture in water bath. To the mixture was added portionwise sodium chlorite (1.19 g), and the mixture was stirred for 1 day at the same temperature. The reaction mixture was cooled in an ice bath, adjusted to pH 4 with 1M hydrochloric acid and extracted with chloroform. The organic layer was separated, dried over magnesium sulfate and evaporated in vacuo. The residue was chromatographed on silica gel eluting with chloroform-n-hexane-methanol to give 1-(3-tert-butyldiphenylsilyloxymethyl-2,4-dichlorophenyl)-2-carboxypyrrole (1.12 g) as an oil.

NMR (CDCl$_3$, δ): 1.03 (9H, s), 2.93 (2H, s), 6.28–6.37 (1H, m), 6.79–6.86 (1H, m), 7.08–7.15 (1H, m), 7.18 (1H, d, J=8 Hz), 7.28–7.47 (7H, m), 7.67–7.79 (4H, m).

(2) A mixture of 1-(3-tert-butyldiphenylsilyloxymethyl-2,4-dichlorophenyl)-2-carboxypyrrole (1.12 g), potassium carbonate (360 mg) and iodoethane (490 mg) in N,N-dimethylformamide (10 ml) was stirred for 16 hours at 60° C. The reaction mixture was poured into water and extracted with ethyl acetate. The organic layer was washed with 1M hydrochloric acid, water and brine and dried over magnesium sulfate. The solvent was evaporated to give 1-(3-tert-butyldiphenylsilyloxymethyl-2,4-dichlorophenyl)-2-ethoxycarbonylpyrrole (1.22 g) as an oil.

NMR (CDCl$_3$, δ): 1.05 (3H, s), 1.14 (3H, t, J=7.5 Hz), 4.10 (2H, q, J=7.5 Hz), 4.95 (2H, s), 6.31–6.36 (1H, m), 6.78–6.83 (1H, m), 7.08–7.13 (1H, m), 7.23 (1H, d, J=8 Hz), 7.31–7.48 (7H, m), 7.68–7.78 (4H, m).

(3) 1-(2,4-Dichloro-3-hydroxymethylphenyl)-2-ethoxycarbonylpyrrole was obtained according to a similar manner to that of Example 1-(5).

NMR (CDCl$_3$, δ): 1.20 (3H, t, J=7.5 Hz), 2.13 (1H, t, J=7.5 Hz), 4.14 (2H, q, J=7.5 Hz), 5.01 (2H, d, J=7.5 Hz), 6.32–6.38 (1H, m), 6.77–6.83 (1H, m), 7.08–7.13 (1H, m), 7.27 (1H, d, J=8 Hz), 7.41 (1H, d, J=8 Hz).

(4) 1-(2,4-Dichloro-3-methanesulfonyloxymethylphenyl)-2-ethoxycarbonylpyrrole was obtained according to a similar manner to that of Example 24-(3).

NMR (CDCl$_3$, δ): 1.21 (3H, t, J=7.5 Hz), 3.08 (3H, s), 4.14 (2H, q, J=7.5 Hz), 5.57 (2H, s), 6.33–6.40 (1H, m), 6.78–6.85 (1H, m), 7.08–7.13 (1H, m), 7.37 (1H, d, J=8 Hz), 7.47 (1H, d, J=8 Hz).

(5) 1-[2,4-Dichloro-3-[2-methyl-4-(pyrazol-1-yl)quinolin-8-yloxymethyl]phenyl]-2-ethoxycarbonylpyrrole was obtained according to a similar manner to that of Example 21.

NMR (CDCl$_3$, δ): 1.21 (3H, t, J=7.5 Hz), 2.78 (3H, s), 4.15 (2H, q, J=7.5 Hz), 5.64 (1H, d, J=10 Hz), 5.72 (1H, d, J=10 Hz), 6.32–6.37 (1H, m), 6.56–6.60 (1H, m), 6.81–6.87 (1H, m), 7.08–7.14 (1H, m), 7.32 (2H, d, J=8 Hz), 7.36–7.50 (3H, m), 7.73 (1H, d, J=8 Hz), 7.83–7.93 (2H, m).

(6) To a solution of 1-[2,4-dichloro-3-[2-methyl-4-(pyrazol-1-yl)quinolin-8-yloxymethyl]phenyl]-2-ethoxycarbonylpyrrole (395 mg) in 1,4-dioxane (5 ml) was added 1N sodium hydroxide solution (1.8 ml), and the mixture was refluxed for 2 days. The solvent was removed in vacuo and the residue was dissolved in water. The aqueous solution was washed with diethyl ether and adjusted to pH 5 with 1N hydrochloric acid. The mixture was extracted with chloroform, and the extract was dried over magnesium sulfate and evaporated in vacuo to give 2-carboxy-1-[2,4-dichloro-3-[2-methyl-4-(pyrazol-1-yl)quinolin-8-yloxymethyl]phenyl]pyrrole (296 mg) as amorphous powder.

NMR (CDCl$_3$, δ): 2.75 (3H, s), 5.66 (1H, d, J=10 Hz), 5.76 (1H, d, J=10 Hz), 6.28–6.34 (1H, m), 6.54–6.60 (1H, m), 6.75–7.81 (1H, m), 7.04–7.10 (1H, m), 7.23 (1H, d, J=8 Hz), 7.28–7.44 (4H, m), 7.62 (1H, d, J=8HZ), 7.83–7.90 (2H, m).

Example 31

(1) To a solution of 2-carboxy-1-[2,4-dichloro-3-[2-methyl-4-(pyrazol-1-yl)quinolin-8-yloxymethyl]phenyl]pyrrole (80 mg) in N,N-dimethylformamide (2 ml) were added 1-ethyl-3-(3-dimethylaminopropyl)carbodiimide hydrochloride (37.3 mg) and 1-hydroxybenzotriazole (30.7 mg) at ambient temperature, and the mixture was stirred for 1.5 hours at the same temperature. To the mixture was added conc. ammonia solution (12 mg) at ambient temperature, and the mixture was stirred for 2 days at the same temperature. The reaction mixture was poured into water and extracted with chloroform. The separated organic layer was washed with water, saturated sodium bicarbonate solution and brine, dried over magnesium sulfate and evaporated in vacuo. The residue was purified by preparative thin layer chromatography (chloroform:methanol=20:1, V/V) to give 2-carbamoyl-1-[2,4-dichloro-3-[2-methyl-4-(pyrazol-1-yl)quinolin-8-yloxymethyl]phenyl]pyrrole (31 mg) as amorphous powder.

NMR (CDCl$_3$, δ): 2.78 (3H, s), 5.44 (2H, br peak), 5.63 (1H, d, J=10 Hz), 5.70 (1H, d, J=10 Hz), 6.30–6.37 (1H, m), 6.55–6.60 (1H, m), 6.75–6.80 (1H, m), 6.80–6.85 (1H, m), 7.29–7.49 (6H, m), 7.73 (1H, d, J=8 Hz), 7.84–7.93 (2H, m).

(2) 1-[2,4-Dichloro-3-[2-methyl-4-(pyrazol-1-yl)quinolin-8-yloxymethyl]phenyl]-2-(methylcarbamoyl)pyrrole was obtained from 2-carboxy-1-[2,4-dichloro-3-[2-methyl-4-(pyrazol-1-yl)quinolin-8-yloxymethyl]phenyl]pyrrole and methylamine hydrochloride according to a similar manner to that of Example 31-(1).

NMR (CDCl$_3$, δ): 2.79 (3H, s), 2.85 (3H, d, J=6 Hz), 5.63 (1H, d, J=10 Hz), 5.70 (1H, d, J=10 Hz), 5.90 (1H, br peak), 6.30–6.33 (1H, m), 6.56–6.61 (1H, m), 6.65–6.70 (1H, m), 6.77–6.82 (1H, m), 7.30–7.41 (3H, m), 7.41–7.50 (2H, m), 7.73 (1H, d, J=8 Hz), 7.85–7.93 (2H, m).

Example 32

(1) To a mixture of 2-aminomethyl-1-[3-(tert-butyldiphenylsilyloxymethyl)-2,4-dichlorophenyl]pyrrole (167 mg) and triethylamine (39.8 mg) in dichloromethane (2 ml) was added propionyl chloride (33.4 mg) under ice-cooling, and the mixture was stirred for 1 hour at the same temperature and for 3 hours at ambient temperature. The mixture was poured into water and extracted with chloroform. The organic layer was washed with water and brine, dried over magnesium sulfate and evaporated in vacuo to give 1-(3-tert-butyldiphenylsilyloxymethyl-2,4-dichlorophenyl)-2-(propionamidomethyl)pyrrole (185 mg) as oil.

NMR (CDCl$_3$, δ): 0.99 (3H, t, J=7.5 Hz), 2.01 (2H, q, J=7.5 Hz), 4.21 (2H, d, J=5 Hz), 4.95 (2H, s), 5.36 (1H, br peak), 6.22–6.31 (2H, m), 6.63–6.68 (1H, m), 7.21–7.28 (1H, m), 7.33–7.53 (7H, m), 7.67–7.79 (4H, m).

(2) 1-(2,4-Dichloro-3-hydroxymethylphenyl)-2-(propionamidomethyl)pyrrole was obtained according to a similar manner to that of Example 1-(5).

NMR (CDCl$_3$, δ): 1.01 (3H, t, J=7.5 Hz), 2.02 (2H, q, J=7.5 Hz), 4.20 (1H, dd, J=5, 15 Hz), 4.35 (1H, dd, J=5, 15 Hz), 5.00 (1H, s-like), 6.22–6.30 (2H, m), 6.64–6.70 (1H, m), 7.23 (1H, d, J=8 Hz), 7.43 (1H, d, J=8 Hz), 8.45 (1H, br peak).

(3) 1-(2,4-Dichloro-3-methanesulfonyloxymethylphenyl)-2-(propionamidomethyl)pyrrole was obtained according to a similar manner to that of Example 24-(3).

NMR (CDCl$_3$, δ): 1.04 (3H, t, J=7.5 Hz), 2.06 (2H, q, J=7.5 Hz), 3.12 (3H, s), 4.23 (2H, br d, J=5 Hz), 5.40 (1H, br s), 5.57 (2H, s), 6.26–6.31 (2H, m), 6.67 (1H, br s), 7.39 (1H, d, J=8 Hz), 7.50 (1H, d, J=8 Hz).

(4) 1-[2,4-Dichloro-3-[4-(imidazol-1-yl)-2-methylquinolin-8-yloxymethyl]phenyl]-2-(propionamidomethyl)pyrrole was obtained according to a similar manner to that of Example 21.

NMR (CDCl$_3$, δ): 1.05 (3H, t, J=7.5 Hz), 2.09 (2H, q, J=7.5 Hz), 2.80 (3H, s), 4.25 (2H, br d, J=5 Hz), 5.53 (1H, br s), 5.67 (2H, s), 6.28 (2H, br s), 6.70 (1H, br s), 7.28–7.53 (8H, m), 7.84 (1H, br s).

its dihydrochloride

NMR (CDCl$_3$—CD$_3$OD, δ): 0.93 (3H, br t, J=7.5 Hz), 1.86–2.15 (2H, m), 3.15 (3H, br s), 4.09 (1H, br d, J=15 Hz), 4.49 (1H, br d, J=15 Hz), 5.61 (1H, br d, J=10 Hz), 5.81 (1H, br d, J=10 Hz), 6.28 (2H, s), 7.39 (1H, d, J=8 Hz), 7.55 (1H, d, J=8 Hz), 7.66–7.78 (2H, m), 7.83 (1H, br s), 8.01 (1H, br s), 8.45 (1H, br s), 8.67 (1H, br s).

Example 33

1-[2,4-Dichloro-3-[4-(imidazol-1-yl)-2-methylquinolin-8-yloxymethyl]phenyl1-2-[4-(methylcarbamoyl)cinnamoylaminomethyl]pyrrole was obtained from 8-hydroxy-4-(imidazol-1-yl)-2-methylquinoline and 1-(2,4-dichloro-3-chloromethylphenyl)-2-[4-(methylcarbamoyl)cinnamoylaminomethyl]pyrrole according to a similar manner to that of Example 1-(7).

NMR (CDCl$_3$, δ): 2.71 (3H, s), 3.00 (3H, d, J=6 Hz), 4.40 (2H, d, J=6 Hz), 5.51–5.64 (2H, m), 5.98 (1H, t-like), 6.24 (1H, q-like), 6.28–6.31 (1H, m), 6.31–6.41 (2H, m), 6.69–6.73 (1H, m), 7.21 (1H, s), 7.23 (1H, d, J=8 Hz), 7.30–7.53 (9H, m), 7.61 (2H, d, J=8 Hz), 7.80 (1H, s).

its dihydrochloride

NMR (DMSO-d$_6$, δ): 2.70 (3H, s), 2.79 (3H, d, J=6 Hz), 4.04–4.34 (2H, m), 5.39–5.54 (2H, m), 6.19–6.28 (2H, m), 6.67 (1H, d, J=16 Hz), 6.85–6.90 (1H, m), 7.26 (1H, d, J=8 Hz), 7.36 (1H, d, J=16 Hz), 7.44 (1H, d, J=8 Hz), 7.54–7.70 (4H, m), 7.74 (1H, d, J=8 Hz), 7.81–7.90 (3H, m), 8.04 (1H, s), 8.22 (1H, s), 8.32 (1H, t-like), 8.53 (1H, q-like), 9.62 (1H, s).

Example 34

(1) 1-(3-tert-Butyldiphenylsilyloxymethyl-2,4-dichlorophenyl)-2-[4-(dimethylcarbamoyl)cinnamoylaminomethyl]pyrrole was obtained from 2-aminomethyl-1-(3-tert-butyldiphenylsilyloxymethyl-2,4-dichlorophenyl)pyrrole and 4-(dimethylcarbamoyl)cinnamic acid according to a similar manner to that of Example 1-(4).

NMR (CDCl$_3$, δ): 1.02 (9H, s), 2.93–3.19 (6H, m), 4.27–4.37 (2H, m), 4.93 (2H, s), 5.59 (1H, t-like), 6.23 (1H, d, J=16 Hz), 6.27–6.33 (2H, m), 6.65–6.71 (1H, m), 7.21–7.48 (13H, m), 7.66–7.78 (5H, m).

(2) 1-(2,4-Dichloro-3-hydroxymethylphenyl)-2-[4-(dimethylcarbamoyl)cinnamoylaminomethyl]pyrrole was obtained according to a similar manner to that of Example 1-(5).

NMR (CDCl$_3$, δ): 2.60 (1H, t-like), 3.00 (3H, s), 3.12 (3H, s), 4.34 (1H, dd, J=4, 15 Hz), 4.50 (1H, dd, J=4, 15 Hz), 4.92–5.00 (2H, m), 5.62 (1H, t-like), 6.20 (1H, d, J=16 Hz), 6.27–6.30 (2H, m), 6.67–6.73 (1H, m), 7.22–7.28 (1H, m), 7.35–7.51 (6H, m).

(3) 1-(2,4-Dichloro-3-methanesulfonyloxymethylphenyl)-2-[4-(dimethylcarbamoyl)cinnamoylaminomethyl]pyrrole was obtained according to a similar manner to that of Example 24-(3).

NMR (CDCl$_3$, δ): 2.94–3.17 (9H, m), 4.35 (2H, d, J=5 Hz), 5.51 (2H, d, J=5 Hz), 5.73 (1H, br peak), 6.23–6.36 (3H, m), 6.65–6.71 (1H, m), 7.37–7.57 (7H, m).

(4) 1-[2,4-Dichloro-3-[4-(imidazol-1-yl)-2-methylquinolin-8-yloxymethyl)phenyl]-2-[4-(dimethylcarbamoyl)cinnamoylaminomethyl]pyrrole was obtained according to a similar manner to that of Example 21.

NMR (CDCl$_3$, δ): 2.73 (3H, s), 2.95 (3H, s), 3.10 (3H, s), 4.41 (2H, d, J=6 Hz), 5.59 (2H, d, J=5 Hz), 5.98 (1H, t-like), 6.26–6.40 (3H, m), 6.68–6.73 (1H, m), 7.20–7.44 (8H, m), 7.44–7.54 (3H, m), 7.84 (1H, s-like).

its dihydrochloride

NMR (DMSO-d$_6$, δ): 2.70 (3H, s), 2.91 (3H, br s), 2.98 (3H, br s), 4.11 (1H, dd, J=5, 15 Hz), 4.28 (1H, dd, J=5, 15 Hz), 5.55 (2H, d, J=5 Hz), 6.18–6.28 (2H, m), 6.65 (1H, d, J=16 Hz), 6.88 (1H, d, J=2 Hz), 7.24 (1H, d, J=8 Hz), 7.35 (1H, d, J=16 Hz), 7.40–7.48 (3H, m), 7.55–7.68 (4H, m), 7.73 (1H, d, J=8 Hz), 7.83 (1H, s-like), 8.00–8.05 (1H, m), 8.21–8.25 (1H, m), 8.33 (1H, t-like), 9.63 (1H, s).

Example 35

(1) 1-(3-tert-Butyldiphenylsilyloxymethyl-2,4-dichlorophenyl)-2-[4-[N-(2-pyridylmethyl)carbamoyl]-cinnamoylaminomethyl]pyrrole was obtained from 2-aminomethyl-1-(3-tert-butyldiphenylsilyloxymethyl-2,4-dichlorophenyl)pyrrole and 4-[N-(2-pyridylmethyl) carbamoyl]cinnamic acid according to a similar manner to that of Example 1-(4).

NMR (CDCl$_3$, δ): 4.33 (2H, d, J=5 Hz), 4.77 (2H, d, J=5 Hz), 4.90 (2H, s), 5.60 (1H, t-like), 6.19–6.34 (3H, m), 6.65–6.70 (1H, m), 7.20–7.80 (21H, m), 8.58 (1H, d, J=6 Hz).

(2) 1-(2,4-Dichloro-3-hydroxymethylphenyl)-2-[4-[N-(2-pyridylmethyl)carbamoyl]cinnamoylaminomethyl]pyrrole was obtained according to a similar manner to that of Example 1-(5).

NMR (DMSO-d$_6$, δ): 4.06 (1H, dd, J=5, 15 Hz), 4.20 (1H, dd, J=5, 15 Hz), 4.58 (2H, d, J=7 Hz), 4.71 (2H, d, J=5 Hz), 5.30 (1H, t, J=7 Hz), 6.18–6.24 (2H, m), 6.65 (1H, d, J=16 Hz), 6.74–6.79 (1H, m), 7.28 (1H, dd, J=6, 8 Hz), 7.30–7.40 (2H, m), 7.45 (1H, d, J=8 Hz), 7.57 (1H, d, J=8 Hz), 7.63 (2H, d, J=8 Hz), 7.76 (1H, t, J=8 Hz), 7.95 (2H, d, J=8 Hz), 8.30 (1H, t, J=6 Hz), 8.51 (1H, d, J=6 Hz), 9.16 (1H, t, J=6 Hz).

(3) 1-(2,4-Dichloro-3-chloromethylphenyl)-2-[4-[N-(2-pyridylmethyl)carbamoyl]cinnamoylaminomethyl]pyrrole was obtained according to a similar manner to that of Example 1-(6).

NMR (CDCl$_3$, δ): 4.27–4.48 (2H, m), 4.77 (2H, d, J=5 Hz), 4.85 (2H, s), 5.61 (1H, br peak), 6.24–6.36 (3H, m), 6.67–6.72 (1H, m), 7.20–7.28 (1H, m), 7.33 (2H, d, J=8 Hz), 7.44–7.57 (4H, m), 7.57–7.75 (2H, m), 7.88 (2H, d, J=8 Hz), 8.59 (1H, d, J=6 Hz).

(4) 1-[2,4-Dichloro-3-[4-(imidazol-1-yl)-2-methylquinolin-8-yloxymethyl]phenyl]-2-[4-[N-(2-pyridylmethyl)carbamoyl]cinnamoylaminomethyl]pyrrole was obtained according to a similar to that of Example 1-(7).

NMR (CDCl$_3$, δ): 2.70 (3H, s), 4.41 (2H, d, J=5 Hz), 4.73 (2H, d, J=5 Hz), 5.50–5.59 (2H, m), 6.01 (1H, br peak), 6.25–6.30 (1H, m), 6.30–6.35 (1H, m), 6.39 (1H, d, J=16 Hz), 6.67–6.72 (1H, m), 7.15–7.53 (13H, m), 7.60 (1H, br peak), 7.64–7.75 (3H, m), 7.82 (1H, br s), 8.50–8.58 (1H, m).

its trihydrochloride

NMR (DMSO-d$_6$, δ): 2.69 (3H, s), 4.11 (1H, dd, J=5, 15 Hz), 4.27 (1H, dd, J=5, 15 Hz), 4.79 (1H, d, J=5 Hz), 5.41–5.54 (2H, m), 6.18–6.28 (2H, m), 6.72 (1H, d, J=16 Hz), 6.86–6.90 (1H, m), 7.23 (1H, d, J=8 Hz), 7.38 (1H, d, J=16 Hz), 7.46 (1H, d, J=8 Hz), 7.59 (1H, t, J=8 Hz), 7.62–7.89 (7H, m), 7.98 (2H, d, J=8 Hz), 8.03–8.05 (1H, m), 8.20–8.24 (1H, m), 8.30–8.42 (2H, m), 8.77 (1H, d, J=6 Hz), 9.50 (1H, t-like), 9.60–9.64 (1H, m).

Example 36

(1) 1-(3-tert-Butyldiphenylsilyloxymethyl-2,4-dichlorophenyl)-2-[4-[N-(4-pyridyl)carbamoyl] cinnamoylaminomethyl]pyrrole was obtained from 2-aminomethyl-1-(3-tert-butyldiphenylsilyloxymethyl-2,4-dichlorophenyl)pyrrole and 4-(N-(4-pyridyl)carbamoyl] cinnamic acid according to a similar manner to that of Example 1-(4).

NMR (CDCl$_3$, δ): 4.31 (2H, d, J=5 Hz), 4.88 (2H, s), 5.67 (1H, t-like), 6.20–6.32 (3H, m), 6.65–6.70 (1H, m), 7.30–7.75 (17H, m), 7.80 (2H, d, J=8 Hz), 8.21 (1H, s), 8.54 (2H, d, J=6 Hz).

(2) 1-(2,4-Dichloro-3-hydroxymethylphenyl)-2-[4-[N-(4-pyridyl)carbamoyl]cinnamoylaminomethyl]pyrrole was obtained according to a similar manner to that of Example 1-(5).

NMR (DMSO-d$_6$, δ): 4.06 (1H, dd, J=5, 15 Hz), 4.21 (1H, dd, J=5, 15 Hz), 4.70 (2H, d, J=5 Hz), 5.30 (1H, t-like), 6.18–6.25 (2H, m), 6.70 (1H, d, J=16 Hz), 6.75–6.80 (1H, m), 7.38 (1H, d, J=16 Hz), 7.46 (1H, d, J=8 Hz), 7.57 (1H, d, J=8 Hz), 7.69 (2H, d, J=8 Hz), 7.78 (2H, d, J=6 Hz), 8.00 (2H, d, J=8 Hz), 8.31 (1H, t-like), 8.39 (2H, d, J=6 Hz).

(3) 1-[2,4-Dichloro-3-[4-(imidazol-1-yl)-2-methylquinolin-8-yloxymethyl]phenyl]-2-[4-[N-(4-pyridyl)carbamoyl]cinnamoylaminomethyl]pyrrole was obtained according to a similar manner to that of Example 23-(3).

NMR (CDCl$_3$, δ): 2.67 (3H, s), 4.23–4.37 (1H, m), 4.37–4.53 (1H, m), 5.51–5.65 (1H, m), 6.15 (1H, br peak), 6.23–6.38 (3H, m), 6.68 (1H, s), 7.11–7.50 (1H, m), 7.60–7.83 (5H, m), 8.46–8.61 (1H, m), 8.61–8.77 (1H, m).

its trihydrochloride

NMR (CDCl$_3$—CD$_3$OD, δ): 3.00 (3H, s), 4.20 (1H, d, J=15 Hz), 4.98 (1H, d, J=15 Hz), 5.67 (1H, d, J=10 Hz), 5.83 (1H, d, J=10 Hz), 6.25–6.32 (1H, m), 6.32–6.38 (1H, m), 6.51 (1H, d, J=16 Hz), 6.74–6.80 (1H, m), 7.37 (1H, d, J=16 Hz), 7.43–7.53 (2H, m), 7.53–7.70 (4H, m), 7.80–8.28 (6H, m), 8.52 (2H, d, J=6 Hz), 8.61 (2H, d, J=6 Hz), 9.70 (1H, br peak).

Example 37

1-[2,4-Dichloro-3-[2-methyl-4-(morpholino)quinolin-8-yloxymethyl]phenyl]-2-[4-(dimethylcarbamoyl) cinnamoylaminomethyl]pyrrole was obtained from 8-hydroxy-2-methyl-4-(morpholino)quinoline and 1-[2,4-dichloro-3-(methanesulfonyloxymethyl)phenyl]-2-[4-(dimethylcarbamoyl)cinnamoylaminomethyl]pyrrole according to a similar manner to that of Example 21.

NMR (CDCl$_3$, δ): 2.59 (3H, s), 2.92 (3H, s), 3.29 (3H, s), 3.13–3.27 (4H, m), 3.91–4.03 (4H, m), 4.28 (1H, dd, J=5, 15 Hz), 4.46 (1H, dd, J=5, 15 Hz), 5.50 (1H, d, J=10 Hz), 5.57 (1H, d, J=10 Hz), 6.23–6.30 (1H, m), 6.30–6.41 (2H, m), 6.51 (1H, br peak), 6.63–6.70 (1H, m), 6.70–6.75 (1H, m), 7.04–7.50 (9H, m), 7.64 (1H, d, J=8 Hz).
its dihydrochloride
NMR (DMSO-d$_6$, δ): 2.65 (3H, s), 2.90 (3H, br s), 2,98 (3H, br s), 3.65–3.95 (8H, m), 4.18 (1H, dd, J=4, 15 Hz), 4.60 (1H, dd, J=8, 15 Hz), 5.48 (1H, d, J=10 Hz), 5.60 (1H, d, J=10 Hz), 6.17–6.24 (1H, m), 6.24–6.29 (1H, m), 6.53 (1H, d, J=16 Hz), 6.81–6.86 (1H, m), 7.16–7.31 (2H, m), 7.31–7.47 (2H, m), 7.47–7.57 (3H, m), 7.57–7.78 (4H, m), 8.47 (1H, t-like).

Example 38

1-[2,4-Dichloro-3-[2-methyl-4-(morpholino)quinolin-8-yloxymethyl]phenyl]-2-[4-[N-(2-pyridylmethyl) carbamoyl]-cinnamoylaminomethyl]pyrrole was obtained from 8-hydroxy-2-methyl-4-(morpholino)quinoline and 1-(2,4-dichloro-3-chloromethylphenyl)-2-(4-[N-(2-pyridylmethyl)carbamoyl]-cinnamoylaminomethyl]pyrrole according to a similar manner to that of Example 1-(7).

NMR (CDCl$_3$, δ): 2.55 (3H, s), 3.08–3.26 (4H, m), 3.87–4.02 (4H, m), 4.26 (1H, dd, J=5, 15 Hz), 4.48–4.58 (1H, m), 4.74 (2H, d, J=5 Hz), 5.50 (1H, d, J=10 Hz), 5.58 (1H, d, J=10 Hz), 6.24–6.31 (1H, m), 6.31–6.44 (2H, m), 6.58 (1H, br peak), 6.64–6.71 (2H, m), 7.15 (1H, d, J=8 Hz), 7.20–7.52 (7H, m), 7.52–7.74 (5H, m), 8.59 (1H, d, J=5 Hz).
its trihydrochloride
NMR (DMSO-d$_6$, δ): 2.65 (3H, s), 3.67–3.87 (8H, m), 4.17 (1H, dd, J=5, 15 Hz), 4.58 (1H, dd, J=7, 15 Hz), 4.73 (2H, d, J=5 Hz), 5.49 (1H, d, J=10 Hz), 5.61 (1H, d, J=10 Hz), 6.20–6.24 (1H, m), 6.24–6.28 (1H, m), 6.60 (1H, d, J=16 Hz), 6.82–6.85 (1H, m), 7.25 (1H, s), 7.30 (1H, d, J=16 Hz), 7.50–7.77 (10H, m), 7.95 (2H, d, J=8 Hz), 8.22 (1H, t-like), 8.47–8.54 (1H, m), 8.71 (1H, d, J=6 Hz), 9.43 (1H, t-like).

Example 39

1-[2,4-Dichloro-3-[2-methyl-4-(morpholino)quinolin-8-yloxymethyl]phenyl]-2-[4-[N-(4-pyridyl)carbamoyl] cinnamoylaminomethyl]pyrrole was obtained from 8-hydroxy-2-methyl-4-(morpholino)quinoline and 1-(2,4-dichloro-3-hydroxymethylphenyl)-2-[4-[N-(4-pyridyl) carbamoyl]-cinnamoylaminomethyl]pyrrole according to a similar manner to that of Example 23-(3).

NMR (CDCl$_3$, δ): 2.46 (3H, s), 3.26 (4H, br peak), 3.90–4.01 (4H, m), 4.17 (1H, br peak), 4.47 (1H, br peak), 5.41 (2H, br s), 6.19–6.26 (1H, m), 6.26–6.30 (1H, m), 6.35 (1H, d, J=16 Hz), 6.61–6.68 (1H, m), 6.70–6.78 (1H, m), 7.06–7.24 (6H, m), 7.24 (1H, t, J=8 Hz), 7.63 (1H, d, J=8 Hz), 7.68–7.83 (4H, m), 8.44 (2H, br peak), 9.82 (1H, br peak).
its trihydrochloride
NMR (CDCl$_3$—CD$_3$OD, δ): 2.73 (3H, s), 3.75–3.90 (4H, m), 3.90–4.07 (4H, m), 4.15 (1H, d, J=15 Hz), 5.10 (1H, d, J=15 Hz), 5.55 (1H, d, J=10 Hz), 5.75 (1H, d, J=10 Hz), 6.22–6.33 (2H, m), 6.45 (1H, d, J=16 Hz), 6.71–6.78 (1H, m), 7.00–7.10 (1H, m), 7.27 (1H, d, J=16 Hz), 7.39 (2H, s-like), 7.50–7.78 (5H, m), 8.05–8.16 (2H, m), 8.56 (4H, s-like).

Example 40

(1) To a solution of 3-bromo-1-tert-butyldiphenylsilyloxymethyl-2,6-dimethylbenzene (454 mg) in anhydrous tetrahydrofuran (2.5 ml) was added 1.6N solution of n-butyllithium in n-hexane (0.63 ml) dropwise in a dry-ice acetone bath, and the mixture was stirred at the same temperature for 1 hour. To this mixture was added a solution of zinc chloride (140 mg) in tetrahydrofuran (1.4 ml) dropwise under dry-ice acetone cooling. The dry-ice acetone bath was removed, and the reaction mixture was stirred at ambient temperature for 1 hour. This mixture was added to a solution of 2-bromobenzonitrile and tetrakis (triphenylphosphine)palladium (O) (23 mg) in tetrahydrofuran (1 ml) dropwise at ambient temperature. The reaction mixture was stirred at the same temperature for 7 hours and stood overnight in the dark. The mxiture was diluted with ethyl acetate, washed with 1N hydrochloric acid, brine and saturated aqueous sodium bicarbonate solution, dried over magnesium sulfate and evaporated in vacuo. The residue was purified by a silica gel column chromatography (n-hexane:ethyl acetate=25:1, V/V) to give 2-(3-tert-butyldiphenylsilyloxymethyl-2,4-dimethylphenyl) benzonitrile as a colorless oil (233 mg).

NMR (CDCl$_3$, δ): 1.06 (9H, s), 2.08 (3H, s), 2.28 (3H, s), 4.79 (2H, s), 7.04 (1H, d, J=8 Hz), 7.08 (1H, d, J=8 Hz), 7.32–7.75 (14H).

(2) 2-(3-Hydroxymethyl-2,4-dimethylphenyl)benzonitrile was obtained according to a similar manner to that of Example 1-(5).

NMR (CDCl$_3$, δ): 2.27 (3H, s), 2.50 (3H, s), 4.82 (2H, s), 7.07 (1H, d, J=8 Hz), 7.14 (1H, d, J=8 Hz), 7.36 (1H, d, J=8 Hz), 7.45 (1H, t, J=8 Hz), 7.63 (1H, t, J=8 Hz), 7.74 (1H, d, J=8 Hz).

(3) 2-(3-Methanesulfonyloxymethyl-2,4-dimethylphenyl) benzonitrile was obtained according to a similar manner to that of Example 24-(3).

(4) 8-[3-(2-Cyanophenyl)-2,6-dimethylbenzyloxy]-2-methylquinoline was obtained according to a similar manner to that of Example 21.

NMR (CDCl$_3$, δ): 2.33 (3H, s), 2.55 (3H, s), 2.73 (3H, s), 5.40 (1H, d, J=12 Hz), 5.46 (1H, d, J=12 Hz), 7.13 (1H, d, J=8 Hz), 7.18 (1H, d, J=8 Hz), 7.23–7.48 (6H), 7.63 (1H, t, J=8 Hz), 7.74 (1H, d, J=8 Hz), 8.02 (1H, d, J=8 Hz).

(5) 8-[3-(2-Aminomethylphenyl)-2,6-dimethylbenzyloxy]-2-methylquinoline was obtained according to a similar manner to that of Example 1-(3).

(6) 2-Methyl-8-[2,6-dimethyl-3-[2-[4-(methylcarbamoyl)-cinnamoylaminomethyl]phenyl] benzyloxylquinoline was obtained according to a similar manner to that of Example 2-(4).

NMR (CDCl$_3$, δ): 2.10 (3H, s), 2.20 (3H, s), 2.55 (3H, s), 3.00 (3H, d, J=6 Hz), 4.29 (1H, dd, J=16, 6 Hz), 4.48 (1H, dd, J=16, 6 Hz), 5.30 (2H, s), 6.45 (1H, d, J=16 Hz), 6.55 (1H, br s), 6.88–7.78 (6H), 8.23 (1H, d, J=8 Hz).

Example 41

(1) To a mixture of 3-aminophenylboronic acid hemisulfate (472 mg) in toluene (11 ml) were added tetrakis (triphenylphosphine)palladium (O) (64 mg), 2M sodium carbonate solution (5.5 ml), methanol (2.8 ml) and 1-tert-butyldiphenylsilyloxymethyl-2,6-dimethyl-3-bromobenzene (1.0 g) at ambient temperature, and the mixture was heated at 80° C. After 5 hours, the cooled reaction mixture was extracted with chloroform and the organic layer was washed with aqueous sodium bicarbonate solution and brine. The organic layer was dried over magnesium sulfate and evaporated in vacuo. The residue was purified by flash silica gel chromatography eluted with n-hexane-ethyl acetate to give 3-(3-aminophenyl)-1-tert-butyldiphenylsilyloxymethyl-2,6-dimethylbenzene (350 mg) as pale yellow oil.

NMR (CDCl$_3$, δ): 1.05 (9H, s), 2.14 (3H, s), 2.26 (3H, s), 3.67 (2H, br s), 4.77 (2H, s), 6.56–6.80 (3H, m), 7.00 (1H, d, J=8 Hz), 7.06 (1H, d, J=8 Hz), 7.16 (1H, t, J=8 Hz), 7.32–7.48 (6H, m), 7.70 (4H, br d, J=8 Hz).

(2) 3-(3-Acetamidophenyl)-1-tert-butyldiphenylsilyloxymethyl-2,6-dimethylbenzene was obtained according to a similar manner to that of Example 24-(1).

NMR (CDCl$_3$, δ): 1.05 (9H, s), 2.14 (3H, s), 2.19 (3H, s), 2.27 (3H, s), 4.78 (2H, s), 6.98–7.08 (3H, m), 7.13 (1H, br s), 7.27–7.48 (8H, m), 7.57 (1H, br d, J=8 Hz), 7.70 (4H, br d, J=8 Hz), (3) 3-(3-Acetamidophenyl)-1-hydroxymethyl-2,6-dimethylbenzene was obtained according to a similar manner to that of Example 1-(5).

NMR (CDCl$_3$, δ): 2.17 (3H, s), 2.31 (3H, s), 2.49 (3H, s), 4.81 (2H, br s), 7.00 (1H, br d, J=8 Hz), 7.05–7.10 (2H, m), 7.19 (1H, br s), 7.30–7.40 (2H, m), 7.51 (1H, br d, J=8 Hz).

(4) 3-(3-Acetamidophenyl)-1-chloromethyl-2,6-dimethylbenzene was obtained according to a similar manner to that of Example 1-(6).

NMR (CDCl$_3$, δ): 2.18 (3H, s), 2.32 (3H, s), 2.49 (3H, s), 4.74 (2H, s), 7.01 (1H, br d, J=8 Hz), 7.05–7.15 (2H, m), 7.20 (1H, br s), 7.30–7.43 (2H, m), 7.52 (1H, br d, J=8 Hz).

(5) 8-[3-(3-Acetamidophenyl)-2,6-dimethylbenzyloxy]-2-methylquinoline was obtained according to a similar manner to that of Example 1-(7).

mp: 197–199° C.; NMR (CDCl$_3$, δ): 2.01 (3H, s), 2.24 (3H, s), 2.48 (3H, s), 2.69 (3H, s), 5.35 (2H, s), 6.97 (1H, br d, J=8 Hz), 7.06–7.32 (5H, m), 7.36–7.49 (4H, m), 8.04 (1H, d, J=8 Hz), 8.32 (1H, br s).

Example 42

8-[3-(3-Acetamidophenyl)-2,6-dimethylbenzyloxy]-4-(imidazol-1-yl)-2-methylquinoline was obtained from 8-hydroxy-4-(imidazol-1-yl)-2-methylquinoline and 3-(3-acetamidophenyl)-1-chloromethyl-2,6-dimethylbenzene according to a similar manner to that of Example 1-(7).

mp: 214–216° C.; NMR (CDCl$_3$, δ): 2.12 (3H, s), 2.33 (3H, s), 2.50 (3H, s), 2;77 (3H, s), 5.40 (2H, s), 7.01 (1H, br d, J=8 Hz), 7.08–7.17 (2H, m), 7.24–7.41 (7H, m), 7.45–7.54 (2H, m), 7.68 (1H, br s), 7.84 (1H, br s).

Example 43

(1) 1-tert-Butyldiphenylsilyloxymethyl-2,6-dimethyl-3-[3-[4-(methylcarbamoyl)cinnamoylamino]phenyl]benzene was obtained from 3-(3-aminophenyl)-1-tert-butyldiphenylsilyloxymethyl-2,6-dimethylbenzene and 4-(methylcarbamoyl)cinnamic acid according to a similar manner to that of Example 1-(4).

mp: 245–247° C.; NMR (DMSO-d$_6$, δ): 1.01 (9H, s), 2.12 (3H, s), 2.21 (3H, s), 2.79 (3H, d, J=5 Hz), 4.79 (2H, s), 6.88–6.98 (2H, m), 7.01–7.11 (2H, m), 7.30–7.52 (7H, m), 7.59–7.75 (11H, m), 7.90 (2H, d, J=8 Hz), 8.51 (1H, br d, J=5 Hz).

(2) 1-Hydroxymethyl-2,6-dimethyl-3-[3-[4-(methylcarbamoyl)cinnamoylamino]phenyl]benzene was obtained according to a similar manner to that of Example 1-(5).

mp: 272–277° C.; NMR (DMSO-d$_6$, δ): 2.28 (3H, s), 2.40 (3H, s), 2.80 (3H, d, J=5 Hz), 4.57 (2H, d, J=6 Hz), 4.78 (1H, t, J=6 Hz), 6.87–7.10 (4H, m), 7.38 (1H, t, J=8 Hz), 7.57–7.74 (5H, m), 7.89 (2H, d, J=8 Hz), 8.50 (1H, br d, J=5 Hz).

(3) 1-Chloromethyl-2,6-dimethyl-3-[3-[4-(methylcarbamoyl)cinnamoylamino]phenyl]benzene was obtained according to a similar manner to that of Example 1-(6).

mp: 236.2–243.8° C.; NMR (DMSO-d$_6$, δ): 2.30 (3H, s), 2.44 (3H, s), 2.79 (3H, d, J=5 Hz), 4.88 (2H, s), 4.78 (1H, t, J=6 Hz), 6.90 (1H, d, J=15 Hz), 6.99 (1H, br d, J=8 Hz), 7.09–7.21 (2H, m), 7.40 (1H, t, J=8 Hz), 7.58–7.74 (5H, m), 7.89 (2H, d, J=8 Hz), 8.50 (1H, br d, J=5 Hz).

(4) 2-Methyl-8-[2,6-dimethyl-3-[3-[4-(methylcarbamoyl)cinnamoylamino]phenyl]benzyloxy]quinoline was obtained according to a similar manner to that of Example 1-(7).

mp: 234–238° C.; NMR (CDCl$_3$—CD$_3$OD, δ): 2.31 (3H, s), 2.46 (3H, s), 2.70 (3H, s), 2.98 (3H, s), 5.32 (2H, s), 6.74 (1H, d, J=15 Hz), 7.02–7.12 (2H, m), 7.18 (1H, br d, J=8 Hz), 7.29–7.59 (7H, m), 7.64–7.81 (4H, m), 8.01 (1H, br d, J=8 Hz), 8.09 (1H, d, J=8 Hz).

Example 44

4-(Imidazol-1-yl)-2-methyl-8-[2,6-dimethyl-3-[3-(4-(methylcarbamoyl)cinnamoylamino]phenyl]benzyloxy]quinoline was obtained from 8-hydroxy-4-(imidazol-1-yl)-2-methylquinoline and 1-chloromethyl-2,6-dimethyl-3-(3-[4-(methylcarbamoyl)cinnamoylamino]phenyl]benzene according to a similar manner to that of Example 1-(7).

mp: 245–247° C.; NMR (CDCl$_3$—CD$_3$OD, δ): 2.32 (3H, s), 2.47 (3H, s), 2.76 (3H, s), 2.98 (3H, s), 5.38 (2H, s), 6.72 (1H, d, J=15 Hz), 7.00–7.12 (2H, m), 7.18 (1H, d, J=8 Hz), 7.29–7.44 (6H, m), 7.50–7.59 (4H, m), 7.69 (1H, d, J=15 Hz), 7.76 (2H, d, J=8 Hz), 7.85 (1H, s), 7.91 (1H, br d, J=8 Hz).

Example 45

(1) 3-(3-tert-Butyldiphenylsilyloxymethyl-2,4-dimethylphenyl)-2-cyanothiophene was obtained from 3-bromo-1-tert-butyldiphenylsilyloxymethyl-2,6-dimethylbenzene and 3-bromo-2-cyanothiophene according to a similar manner to that of Example 40-(1).

NMR (CDCl$_3$, δ): 1.04 (9H, s), 2.13 (3H, s), 2.25 (3H, s), 4.76 (2H, s), 7.00–7.08 (2H, m), 7.13 (1H, d, J=8 Hz), 7.32–7.48 (6H, m), 7.56 (1H, d, J=6 Hz), 7.69 (4H, d-like).

(2) A mixture of 3-(3-tert-butyldiphenylsilyloxymethyl-2,4-dimethylphenyl)-2-cyanothiophene (471 mg) and 1M boranetetrahydrofuran complex (3 ml) was stirred for 30 minutes at 0° C. under nitrogen atmosphere and allowed to stand at ambient temperature overnight. To the mixture was added 4N hydrochloric acid (1.5 ml) under ice-cooling, and the mixture was stirred for 1 hour. The mixture was partitioned between ethyl acetate and water, and the separated organic layer was washed with water and brine, dried over magnesium sulfate and evaporated in vacuo. The residue was purified by silica gel column chromatography (chloroform:methanol=50:1, V/V) to give 2-aminomethyl-3-(3-tert-butyldiphenylsilyloxymethyl- 2,4-dimethylphenyl)thiophene (415 mg) as oil.

NMR (CDCl$_3$, δ): 1.05 (9H, s), 2.02 (3H, s), 2.27 (3H, s), 3.78 (2H, s), 4.76 (2H, s), 6.83 (1H, d, J=6 Hz), 7.00 (2H, s-like), 7.20 (1H, d, J=6 Hz), 7.30–7.48 (6H, m), 7.63–7.75 (4H, m).

(3) 3-(3-tert-Butyldiphenylsilyloxymethyl-2,4-dimethylphenyl)-2-[4-(methylcarbamoyl)cinnamoylaminomethyl]thiophene was obtained according to a similar manner to that of Example 1-(4).

NMR (CDCl$_3$, δ): 1.05 (9H, s), 2.05 (3H, s), 2.28 (3H, s), 3.02 (3H, d, J=6 Hz), 4.49 (2H, br peak), 4.77 (2H, s), 6.00 (1H, br peak), 6.29 (1H, br peak), 6.35 (1H, d, J=16 Hz), 6.85 (1H, d, J=6 Hz), 7.02 (2H, s-like), 7.25 (1H, d, J=8 Hz), 7.33–7.90 (15H,m).

(4) 3-(2,4-Dimethyl-3-hydroxymethylphenyl)-2-[4-(methylcarbamoyl)cinnamoylaminomethyl]thiophene was obtained according to a similar manner to that of Example 1-(5).

NMR (CDCl$_3$—CD$_3$OD, δ): 1.94 (1H, s), 2.23 (3H, s), 2.44 (3H, s), 3.00 (3H, s), 4.50 (2H, s), 4.80 (2H, s), 6.31 (1H, d, J=16 Hz), 6.41 (1H, br peak), 6.88 (1H, d, J=6 Hz), 7.02 (1H, d, J=8 Hz), 7.08 (1H, d, J=8 Hz), 7.23–7.30 (1H, m), 7.50 (2H, d, J=8 Hz), 7.55 (1H, d, J=16 Hz), 7.74 (2H, d, J=8 Hz).

(5) 3-(3-Chloromethyl-2,4-dimethylphenyl)-2-[4-(methylcarbamoyl)cinnamoylaminomethyl]thiophene was obtained according to a similar manner to that of Example 1-(6).

NMR (CDCl$_3$, δ): 2.24 (3H, s), 2.47 (3H, s), 3.02 (3H, d, J=6 Hz), 4.53 (2H, br s), 4.73 (2H, s), 5.73 (1H, br peak), 6.10 (1H, br peak), 6.34 (1H, d, J=16 Hz), 6.88 (1H, d, J=6 Hz), 7.04–7.13 (2H, m), 7.22–7.30 (1H, m), 7.52 (2H, d, J=8 Hz), 7.61 (1H, d, J=16 Hz), 7.74 (1H, d, J=8 Hz).

(6) 3-[2,4-Dimethyl-3-(2-methylquinolin-8-yloxymethyl)-phenyl]-2-[4-(methylcarbamoyl)-cinnamoylaminomethyl]thiophene was obtained according to a similar manner to that of Example 1-(7).

NMR (CDCl$_3$, δ):2.22 (3H, s), 2.50 (3H, s), 2.62 (3H, s), 2.99 (3H, d, J=6 Hz), 5.35 (2H, s), 6.08 (1H, br peak), 6.37 (1H, d, J=16 Hz), 6.87 (1H, d, J=6 Hz), 7.04 (1H, br peak), 7.17 (2H, s-like), 7.20–7.34 (4H, m), 7.42–7.60 (6H, m), 8.07 (1H, d, J=8 Hz).

its hydrochloride

NMR (DMSO-d$_6$, δ): 2.21 (3H, s), 2.43 (3H, s), 2.77 (3H, d, J=6 Hz), 2.88 (3H, s), 4.38 (2H, d, J=5 Hz), 5.45 (2H, s), 6.73 (1H, d, J=16 Hz), 6.93 (1H, d, J=5 Hz), 7.18–7.28 (2H, m), 7.47 (1H, d, J=16 Hz), 7.52 (1H, d, J=5 Hz), 7.62 (2H, d, J=8 Hz), 7.76–7.98 (6H, m), 8.51 (1H, q-like), 8.73 (1H, t-like), 8.92 (1H, br peak).

Example 46

(1) 2-[(E)-3-(6-Acetamidopyridin-3-yl)acryloylaminomethyl]-3-(3-tert-butyldiphenylsilyloxymethyl-2,4-dimethylphenyl)thiophene was obtained from 2-aminomethyl-3-(3-tert-butyldiphenylsilyloxymethyl-2,4-dimethylphenyl)thiophene and (E)-3-(6-acetamidopyridin-3-yl)acrylic acid according to a similar manner to that of Example 1-(4).

NMR (CDCl$_3$, δ): 1.05 (9H, s), 2.04 (3H, s), 2.22 (3H, s), 2.28 (3H, s), 4.50 (2H, br s), 4.77 (2H, s), 5.70 (1H, br peak), 6.26 (1H, d, J=16 Hz), 6.85 (1H, d, J=6 Hz), 6.99–7.07 (2H, m), 7.21–7.32 (1H, m), 7.31–7.50 (6H, m), 7.57 (1H, d, J=16 Hz), 7.70 (4H, d-like), 7.80 (1H, d, J=8 Hz), 8.03 (1H, s-like), 8.20 (1H, d, J=8 Hz), 8.33 (1H, s-like).

(2) 2-[(E)-3-(6-Acetamidopyridin-3-yl)acryloylaminomethyl]-3-(2,4-dimethyl-3-hydroxymethylphenyl)thiophene was obtained according to a similar manner to that of Example 1-(5).

NMR (CDCl$_3$, δ): 2.20 (3H, s), 2.25 (3H, s), 2.44 (3H, s), 4.53 (2H, d, J=6 Hz), 4.80 (2H, s), 5.66 (1H, br peak), 6.21 (1H, d, J=16 Hz), 6.89 (1H, d, J=6 Hz), 7.02 (1H, d, J=8 Hz), 7.08 (1H, d, J=8 Hz), 7.21–7.35 (1H, m), 7.53 (1H, d, J=16 Hz), 7.80 (1H, d, J=8 Hz), 7.94 (1H, s-like), 8.20 (1H, d, J=8 Hz), 8.33 (1H, s-like).

(3) To a mixture of 2-[(E)-3-(6-acetamidopyridin-3-yl)acryloylaminomethyl]-3-(2,4-dimethyl-3-hydroxymethylphenyl)thiophene (45 mg) and triethylamine (13.6 mg) in N,N-dimethylformamide (2 ml) was added methanesulfonyl chloride (14.2 mg) under ice-cooling, and the mixture was stirred for 1 hour at the same temperature and for 5 hours at ambient temperature. The mixture was poured into water and extracted with chloroform. The organic layer was washed with water and brine, dried over magnesium sulfate and evaporated in vacuo to give a residue containing 2-[(E)-3-(6-acetamidopyridin-3-yl)acryloylaminomethyl]-3-(2,4-dimethyl-3-chloromethylphenyl)thiophene. To a mixture of 8-hydroxy-2-methylquinoline (14.8 mg) and potassium carbonate (39 mg) in N,N-dimethylformamide (0.5 ml) was added a solution of the residue obtained above in N,N-dimethylformamide (1.5 ml) at ambient temperature, and the mixture was stirred for 6 hours at 50° C. The mixture was poured into water and extracted with chloroform. The organic layer was washed with water and brine, dried over magnesium sulfate and evaporated in vacuo. The residue was purified by preparative thin layer chromatography (chloroform:methanol=20:1, V/V) to give 2-[(E)-3-(6-acetamidopyridin-3-yl)acryloylaminomethyl]-3-[2,4-dimethyl-3-(2-methylquinolin-8-yloxymethyl)phenyl]thiophene (26 mg) as amorphous powder.

NMR (CDCl$_3$, δ): 2.18 (3H, s), 2.22 (3H, s), 2.50 (3H, s), 2.64 (3H, s), 5.35 (2H, s), 6.29 (1H, d, J=16 Hz), 6.86 (1H, d, J=8 Hz), 7.02 (1H, br peak), 7.15 (1H, s), 7.20–7.32 (5H, m), 7.36 (1H, dd, J=8, 2 Hz), 7.43–7.53 (2H, m), 7.86 (1H, d, J=8 Hz), 8.09 (1H, d, J=8 Hz), 8.17 (1H, s-like).

Example 47

(1) 2-Acetamidomethyl-3-(3-tert-butyldiphenylsilyloxymethyl-2,4-dimethylphenyl)thiophene was obtained from 2-aminomethyl-3-(3-tert-butyldiphenylsilyloxymethyl-2,4-dimethylphenyl)thiophene and acetic anhydride according to a similar manner to that of Example 24-(1).

NMR (CDCl$_3$, δ): 1.05 (9H, s), 1.91 (3H, s), 2.00 (3H, s), 2.26 (3H, s), 4.35 (2H, br s), 4.75 (2H, s), 5.50 (1H, br s), 6.83 (1H, d, J=6 Hz), 6.96 (1H, d, J=7.5 Hz), 7.02 (1H, d, J=7.5 Hz), 7.23 (1H, d, J=6 Hz), 7.31–7.49 (6H, m), 7.69 (4H, d-like).

(2) 2-Acetamidomethyl-3-(2,4-dimethyl-3-hydroxymethylphenyl)thiophene was obtained according to a similar manner to that of Example 1-(5).

NMR (CDCl$_3$, δ): 1.66 (1H, t-like), 1.89 (3H, s), 2.23 (3H, s), 2.49 (3H, s), 4.39 (2H, d, J=6 Hz), 4.81 (2H, s), 5.53 (1H, br s), 6.88 (1H, d, J=6 Hz), 7.00 (1H, d, J=8 Hz), 7.09 (1H, d, J=8 Hz), 7.22–7.28 (1H, m).

(3) 2-Acetamidomethyl-3-(3-methanesulfonyloxymethyl-2,4-dimethylphenyl)thiophene was obtained according to a similar manner to that of Example 24-(3).

NMR (CDCl$_3$, δ): 1.93 (3H, s), 2.22 (3H, s), 2.47 (3H, s), 3.69 (3H, s), 4.37 (2H, br peak), 4.73 (2H, s), 5.53 (1H, br peak), 6.86 (1H, d, J=5 Hz), 7.03 (1H, d, J=8 Hz), 7.10 (1H, d, J=8 Hz), 7.25 (1H, d, J=5 Hz).

(4) 2-Acetamidomethyl-3-[3-[2-methyl-4-(pyrazol-1-yl)quinolin-8-yloxymethyl]-2,4-dimethylphenyl]thiophene was obtained according to a similar manner to that of Example 21.

NMR (CDCl$_3$, δ): 1.90 (3H, s), 2.26 (3H, s), 2.55 (3H, s), 2.76 (3H, s), 4.40 (2H, d, J=6 Hz), 5.39 (2H, s), 6.08 (1H, br peak), 6.56–6.61 (1H, m), 6.87 (1H, d, J=5 Hz), 7.10 (1H, d, J=8 Hz), 7.15 (1H, d, J=8 Hz), 7.21–7.28 (1H, m), 7.32 (1H, d, J=8 Hz), 7.40 (1H, s), 7.48 (1H, t, J=8 Hz), 7.72 (1H, d, J=8 Hz), 7.86–7.93 (2H, m).

Example 48

(1) The mixture of 60% sodium hydride in oil (56 mg) and dimethyl sulfoxide (6 ml) was stirred at 60° C. under nitrogen atmosphere for 1 hour. To the mixture was added (2-phthalimidoethyl)triphenylphosphonium bromide (1.19 g) at ambient temperature, and the mixture was stirred for 30 minutes. To the mixture was added 8-(2,6-dichloro-3-formylbenzyloxy)-2-methylquinoline (400 mg) under water bath cooling, and the mixture was stirred overnight. To the reaction mixture was added water and extracted with chloroform. The organic layer was washed with water three times and brine, dried over magnesium sulfate and evaporated in vacuo. The residue was purified by flash silica gel chromatography eluted with n-hexane-ethyl acetate to give 8-[2,6-dichloro-3-((Z)-3-phthalimido-1-propenyl)benzyloxy]-2-methylquinoline as amorphous first and 8-[2,6-dichloro-3-((E)-3-phthalimido-1-propenyl)benzyloxy]-2-methylquinoline as amorphous second. The former was crystallized from diisopropyl ether to afford pale yellow crystals (138 mg). The latter was crystallized from diisopropyl ether to afford pale yellow crystals (192 mg).

8-[2,6-Dichloro-3-((Z)-3-phthalimido-1-propenyl)benzyloxy]-2-methylquinoline mp: 186–189° C.; NMR (CDCl$_3$, δ): 2.75 (3H, s), 4.42 (2H, d, J=7 Hz), 5.65 (2H, s), 5.83 (1H, dt, J=10, 7 Hz), 6.67 (1H, br d, J=10 Hz), 7.24–7.31 (2H, m), 7.36–7.47 (3H, m), 7.59 (1H, d, J=8 Hz), 7.69–7.77 (2H, m), 7.82–7.90 (2H, m), 8.01 (1H, d, J=8 Hz).

8-[2,6-Dichloro-3-((E)-3-phthalimido-1-propenyl)benzyloxy]-2-methylquinoline mp: 186–189° C.; NMR (CDCl$_3$, δ): 2.73 (3H, s), 4.49 (2H, d, J=7 Hz), 5.61 (2H, s), 6.22 (1H, dt, J=15, 7 Hz), 7.07 (1H, br d, J=15 Hz), 7.20–7.30 (3H, m), 7.33–7.46 (3H, m), 7.70–7.78 (2H, m), 7.84–7.91 (2H, m), 8.00 (1H, d, J=8 Hz).

(2) To a solution of 8-[2,6-dichloro-3-((E)-3-phthalimido-1-propenyl)benzyloxy]-2-methylquinoline (43 mg) in chloroform (1 ml) was added 2M solution of methylamine in methanol (0.5 ml), and the mixture was stirred in the dark at ambient temperature overnight. The mixture was evaporated in vacuo, and the residue was purified by preparative thin layer chromatography to give 8-[3-((E)-3-amino-1-propenyl)-2,6-dichlorobenzyloxy]-2-methylquinoline (27 mg) as pale yellow amorphous.

NMR (CDCl$_3$, δ): 2.74 (3H, s), 3.53 (2H, d, J=5 Hz), 5.63 (2H, s), 6.29 (1H, dt, J=15, 5 Hz), 6.90 (1H, br d, J=15 Hz), 7.23–7.48 (6H, m), 8.00 (1H, d, J=8 Hz).

(3) 8-[2,6-Dichloro-3-[(E)-3-[4-(methylcarbamoyl)cinnamoylamino]-1-propenyl]benzyloxy]-2-methylquinoline was obtained according to a similar manner to that of Example 2-(4).

NMR (CDCl$_3$—CD$_3$OD, δ): 2.65 (3H, br s), 2.94 (3H, br d, J=5 Hz), 4.15 (2H, br d, J=6 Hz), 5.52 (2H, s), 6.20 (1H, m), 6.61 (1H, d, J=15 Hz), 6.90 (1H, br d, J=15 Hz), 7.21–7.38 (2H, m), 7.40–7.49 (3H, m), 7.51–7.66 (4H, m), 7.79 (2H, br d, J=8 Hz), 8.07 (1H, d, J=8 Hz).

Example 49

(1) 8-[3-((Z)-3-Amino-1-propenyl)-2,6-dichlorobenzyloxy]-2-methylquinoline was obtained according to a similar manner to that of Example 48-(2).

NMR (CDCl$_3$, δ): 2.73 (3H, s), 3.46 (2H, d, J=7 Hz), 5.61 (2H, s), 5.92 (1H, dt, J=10, 7 Hz), 6.57 (1H, br d, J=10 Hz), 7.18 (1H, d, J=8 Hz), 7.24–7.47 (5H, m), 8.02 (1H, d, J=8 Hz).

(2) 8-[2,6-Dichloro-3-[(Z)-3-[4-(methylcarbamoyl)cinnamoylamino]-1-propenyl]benzyloxy]-2-methylquinoline was obtained according to a similar manner to that of Example 2-(4).

NMR (CDCl$_3$—CD$_3$OD, δ): 2.62 (3H, s), 2.95 (3H, br d, J=5 Hz), 4.05 (2H, br d, J=7 Hz), 5.53 (2H, s), 5.96 (1H, dt, J=10, 7 Hz), 6.52 (1H, d, J=15 Hz), 6.61 (1H, br d, J=10 Hz), 6.96 (1H, br s), 7.19–7.32 (4H, m), 7.41–7.50 (3H, m), 7.54 (1H, d, J=15 Hz), 7.68 (2H, d, J=8 Hz), 8.08 (1H, d, J=8 Hz).

Example 50

The following compounds were obtained according to a similar manner to that of Example 2-(4).

(1) 8-[2,6-Dichloro-3-[(Z)-3-[3-methoxy-4-(methylcarbamoyl)cinnamoylamino]-1-propenyl]benzyloxy]-2-methylquinoline mp: 222–225° C.; NMR (CDCl$_3$, δ): 2.61 (3H, s), 2.97 (3H, br d, J=5 Hz), 3.72 (3H, s), 3.99–4.07 (2H, m), 5.54 (2H, s), 5.68 (1H, dt, J=10, 7 Hz), 6.54 (1H, br d, J=10 Hz), 6.60 (1H, d, J=15 Hz), 6.95 (1H, br s), 7.06 (1H, br d, J=8 Hz), 7.14 (1H, br s), 7.19–7.30 (4H, m), 7.41–7.50 (3H, m), 7.75 (1H, br d, J=5 Hz), 8.04 (1H, d, J=8 Hz), 8.09 (1H, d, J=8 Hz).

its hydrochloride

NMR (CDCl$_3$—CD$_3$OD, δ): 3.00 (3H, s), 3.15 (3H, br s), 4.01 (3H, br s), 4.07–4.18 (2H, m), 5.65 (2H, s), 6.03 (1H, m), 6.62 (1H, br d, J=10 Hz), 6.93 (1H, br d, J=15 Hz), 7.12–7.25 (2H, m), 7.31–7.45 (2H, m), 7.53 (1H, br d, J=15 Hz), 7.64 (1H, br d, J=8 Hz), 7.69–7.91 (3H, m), 8.05 (1H, br d, J=8 Hz), 8.80 (1H, br s).

(2) 8-[2,6-Dichloro-3-[(Z)-3-[(E)-3-[6-[(E)-2-(pyridin-4-yl)vinyl]pyridin-3-yl]acryloylamino]-1-propenyl]benzyloxy]-2-methylquinoline NMR (CDCl$_3$, δ): 2.62 (3H, s), 4.02–4.10 (2H, m), 5.56 (2H, s), 5.88 (1H, dt, J=10, 7 Hz), 6.56 (1H, br d, J=10 Hz), 6.65 (1H, d, J=15 Hz), 7.19 (2H, s), 7.22–7.32 (5H,m), 7.39 (2H, br d, J=6 Hz), 7.43–7.59 (4H, m), 7.71 (1H, br d, J=8 Hz), 8.07 (1H, br d, J=8 Hz), 8.56–8.62 (2H, m), 8.66 (1H, br s).

its trihydrochloride

NMR (CDCl$_3$—CD$_3$OD, δ): 3.19 (3H, br s), 4.13 (2H, br d, J=7 Hz), 5.66 (2H, s), 6.02 (1H, m), 6.67 (1H, br d, J=10 Hz), 7.31–7.53 (4H, m), 7.68 (1H, br d, J=8 Hz), 7.79 (1H, br d, J=8 Hz), 7.85–7.95 (2H, m), 8.13–8.50 (5H, m), 8.79–8.91 (4H, m), 8.97 (1H, br s).

Example 51

(1) 1-tert-Butyldiphenylsilyloxymethyl-2,6-dimethyl-3-((Z)-1-methyl-3-trityloxy-1-propenyl)benzene was obtained from 3-bromo-1-tert-butyldiphenylsilyloxymethyl-2,6-dimethylbenzene and 2-iodo-4-trityloxy-2-butene according to a similar manner to that of Example 40-(1).

NMR (CDCl$_3$, δ): 1.00 (9H, s), 1.92 (3H, br s), 1.99 (3H, s), 2.19 (3H, s), 3.26–3.34 (2H, m), 4.62 (1H, br s), 4.66 (1H, br s), 5.63 (1H, br t, J=7 Hz), 6.77 (1H, d, J=8 Hz), 6.85 (1H, d, J=8 Hz), 7.08–7.20 (8H, m), 7.22–7.49 (13H, m), 7.65 (4H, d, J=8 Hz).

(2) A solution of 1-tert-butyldiphenylsilyloxymethyl-2,6-dimethyl-3-((Z)-1-methyl-3-trityloxy-1-propenyl)benzene (500 mg) in acetic acid (5 ml) was heated at 60° C. for 10 hours. The cooled reaction mixture was concentrated in vacuo and ethyl acetate was added thereto. The mixture was washed with aqueous sodium bicarbonate solution, water and brine, dried over magnesium sulfate and evaporated in vacuo. The residue was purified by flash silica gel chromatography eluted with n-hexane-ethyl acetate to give 1-tert-butyldiphenylsilyloxymethyl-2,6-dimethyl-3-((Z)-3-hydroxy-1-methyl-1-propenyl)benzene (92 mg) as colorless oil.

NMR (CDCl$_3$, δ): 1.02 (9H, s), 1.95 (3H, s), 2.09 (3H, s), 2.21 (3H, s), 3.77–3.85 (2H, m), 4.73 (2H, s), 5.70 (1H, br t, J=7 Hz), 6.83 (1H, d, J=8 Hz), 6.95 (1H, br d, J=8 Hz), 7.32–7.47 (6H, m), 7.68 (4H, d, J=8 Hz).

(3) To a mixture of 1-tert-butyldiphenylsilyloxymethyl-2,6-dimethyl-3-((Z)-3-hydroxy-1-methyl-1-propenyl) benzene (120 mg) and triethylamine (32.8 mg) in dichloromethane (1.2 ml) was dropwise added methanesulfonyl chloride (34 mg) under ice-cooling, and the mixture was stirred for 30 minutes at the same temperature. The mixture was washed with water, saturated sodium bicarbonate solution and brine, dried over magnesium sulfate and evaporated in vacuo to give 1-tert-butyldiphenylsilyloxymethyl-2,6-dimethyl-3-((Z)-3-methanesulfonyloxy-1-methyl-1-propenyl)benzene (132 mg) as colorless oil.

NMR (CDCl$_3$, δ): 1.04 (9H, s), 2.00 (3H, s), 2.09 (3H, s), 2.21 (3H, s), 2.81 (3H, s), 4.39 (2H, br d, J=7 Hz), 4.72 (2H, s), 5.71 (1H, br t, J=7 Hz), 6.82 (1H, d, J=8 Hz), 6.97 (1H, br d, J=8 Hz), 7.32–7.48 (6H, m), 7.64–7.71 (4H, m).

(4) To a solution of 1-tert-butyldiphenylsilyloxymethyl-2,6-dimethyl-3-((Z)-3-methanesulfonyloxy-1-methyl-1-propenyl)benzene (132 mg) in N,N-dimethylformamide was added potassium phthalimide (55 mg) at ambient temperature under nitrogen atmosphere, and the mixture was stirred at the same temperature overnight. The mixture was poured into water and extracted with ethyl acetate. The organic layer was washed with water, dried over magnesium sulfate and evaporated in vacuo. The residue was purified by preparative thin layer chromatography (n-hexane:ethyl acetate=4:1, V/V) to give 1-tert-butyldiphenylsilyloxymethyl-2,6-dimethyl-3-((Z)-1-methyl-3-phthalimido-1-propenyl)benzene (99 mg) as colorless oil.

NMR (CDCl$_3$, δ): 1.04 (9H, s), 1.91 (3H, br s), 2.15 (3H, s), 2.21 (3H, s), 3.99 (2H, br d, J=7 Hz), 4.73 (2H, s), 5.49 (1H, br t, J=7 Hz), 6.95 (1H, d, J=8 Hz), 7.00 (1H, d, J=8 Hz), 7.32–7.47 (6H, m), 7.61–7.74 (6H, m), 7.75–7.81 (2H, m).

(5) To a suspension of 1-tert-butyldiphenylsilyloxymethyl-2,6-dimethyl-3-((Z)-1-methyl-3-phthalimido-1-propenyl)benzene (94 mg) in ethanol (1 ml) was added hydrazine monohydrate (16.4 mg), and the mixture was refluxed for 1 hour. After cooling, the insoluble material was filtered off, and the filtrate was concentrated in vacuo. To the residue was added dichloromethane, and the insoluble material was filtered off. The filtrate was concentrated in vacuo to give 3-((Z)-3-amino-1-methyl-1-propenyl)-1-tert-butyldiphenylsilyloxymethyl-2,6-dimethylbenzene (66 mg) as pale yellow amorphous.

NMR (CDCl$_3$, δ): 1.03 (9H, s), 1.91 (3H, br s), 2.09 (3H, s), 2.20 (3H, s), 2.93 (2H, br d, J=7 Hz), 4.73 (2H, s), 5.58 (1H, br t, J=7 Hz), 6.83 (1H, d, J=8 Hz), 6.95 (1H, br d, J=8 Hz), 7.31–7.48 (6H, m), 7.63–7.72 (6H, m).

(6) 3-[(Z)-3-[(E)-3-[6-(Acetamido)pyridin-3-yl]acryloylamino]-1-methyl-1-propenyl]-1-tert-butyldiphenylsilyloxymethyl-2,6-dimethylbenzene was obtained according to a similar manner to that of Example 1-(4).

NMR (CDCl$_3$, δ): 1.02 (9H, s), 1.93 (3H, br s), 2.09 (3H, s), 2.21 (3H, s), 2.23 (3H, s), 3.50–3.83 (2H, m), 4.72 (2H, s), 5.40 (1H, br s), 5.59 (1H, br t, J=7 Hz), 6.25 (1H, d, J=15 Hz), 6.85 (1H, d, J=8 Hz), 6.98 (1H, br d, J=8 Hz), 7.32–7.46 (6H, m), 7.52 (1H, d, J=15 Hz), 7.68 (4H, d, J=8 Hz), 7.80 (1H, dd, J=8, 3 Hz), 7.97 (1H, br s), 8.20 (1H, br d, J=8 Hz), 8.32 (1H, br s). (7) 3-[(Z)-3-[(E)-3-[6-(Acetamido)pyridin-3-yl]acryloylamino]-1-methyl-1-propenyl]-1-hydroxymethyl-2,6-dimethylbenzene was obtained according to a similar manner to that of Example 1-(5).

mp: 160–165° C.; NMR (CDCl$_3$, δ): 1.96 (3H, br s), 2.21 (3H, s), 2.30 (3H, s), 2.41 (3H, s), 3.54–3.80 (2H, m), 4.77 (2H, d, J=5 Hz), 5.50 (1H, br t, J=5 Hz), 5.62 (1H, br t, J=7 Hz), 6.26 (1H, d, J=15 Hz), 6.88 (1H, d, J=8 Hz), 7.03 (1H, br d, J=8 Hz), 7.50 (1H, d, J=15 Hz), 7.80 (1H, dd, J=8, 3 Hz), 8.02 (1H, br s), 8.20 (1H, br d, J=8 Hz), 8.31 (1H, br s).

(8) 3-[(Z)-3-[(E)-3-[6-(Acetamido)pyridin-3-yl]acryloylamino]-1-methyl-1-propenyl]-1-chloromethyl-2,6-dimethylbenzene was obtained according to a similar manner to that of Example 1-(6).

NMR (CDCl$_3$, δ): 1.96 (3H, br s), 2.21 (3H, s), 2.31 (3H, s), 2.41 (3H, s), 3.53–3.82 (2H, m), 4.69 (2H, s), 5.47 (1H, br s), 5.63 (1H, br t, J=7 Hz), 6.28 (1H, d, J=15 Hz), 6.91 (1H, d, J=8 Hz), 7.05 (1H, br d, J=8 Hz), 7.51 (1H, d, J=15 Hz), 7.80 (1H, dd, J=8, 3 Hz), 7.99 (1H, br s), 8.20 (1H, br d, J=8 Hz), 8.33 (1H, br s).

(9) 8-[3-[(Z)-3-[(E)-3-[6-(Acetamido)pyridin-3-yl]acryloylamino]-1-methyl-1-propenyl]-2,6-dimethylbenzyloxy]-2-methylquinoline was obtained according to a similar manner to that of Example 1-(7).

NMR (CDCl$_3$, δ): 1.97 (3H, br s), 2.19 (3H, s), 2.32 (3H, s), 2.43 (3H, s), 2.64 (3H, s), 3.62–3.77 (2H, m), 5.32 (2H, s), 5.77 (1H, br t, J=7 Hz), 6.29 (1H, d, J=15 Hz), 6.40 (1H, br t, J=7 Hz), 6.97 (1H, d, J=8 Hz), 7.08 (1H, br d, J=8 Hz), 7.22–7.31 (2H, m), 7.41–7.52 (4H, m), 7.92–8.00 (2H, m), 8.07 (1H, d, J=8 Hz), 8.21 (1H, br s).

Example 52

(1) To a mixture of quinoline-5-carboxylic acid (4 g) in acetic acid (40 ml) was added borane-pyridine complex (8.59 g) at ambient temperature. After stirred for 18 hours, to the reaction mixture was added 1N hydrochloric acid and heated at 90° C. for 1 hour. The mixture was neutralized with aqueous sodium bicarbonate solution and ethyl acetate was added thereto. The precipitate was filtered off. The organic layer was separated, washed with water, dried over magnesium sulfate and evaporated in vacuo. The residue was purified by flash silica gel chromatography eluted with chloroform-methanol and crystallized from diisopropyl ether to give 1,2,3,4-tetrahydroquinoline-5-carboxylic acid (1.12 g) as pale brown crystals.

mp 135–138° C.; NMR (CDCl$_3$, δ): 1.89–1.99 (2H, m), 3.12 (2H, t, J=7 Hz), 3.30 (2H, t, J=7 Hz), 6.67 (1H, d, J=8 Hz), 7.02 (1H, t, J=8 Hz), 7.32 (1H, d, J=8 Hz).

(2) 1,2,3,4-Tetrahydro-5-hydroxymethylquinoline was obtained according to a similar manner to that of Preparation 6-(2).

mp: 120–122° C.; NMR (CDCl$_3$, δ): 1.92–2.03 (2H, m), 2.78 (2H, t, J=7 Hz), 3.28 (2H, t, J=7 Hz), 3.37 (1H, br s), 4.61 (2H, s), 6.45 (1H, d, J=8 Hz), 6.68 (1H, d, J=8 Hz), 6.98 (1H, t, J=8 Hz).

(3) To a mixture of 1,2,3,4-tetrahydro-5-hydroxymethylquinoline (50 mg) and triethylamine (93 mg) in dichloromethane (1 ml) was added phthalimidoacetyl chloride (151 mg) under ice-cooling, and the mixture was stirred for 2 hours at ambient temperature. The mixture was washed with water, saturated sodium bicarbonate solution and brine, dried over magnesium sulfate and evaporated in vacuo. The residue was crystallized from ethyl acetate to give 1,2,3,4-tetrahydro-1-phthalimidoacetyl-5-(phthalimidoacetoxymethyl)-quinoline (160 mg) as pale brown crystals.

mp: 244–246° C.; NMR (CDCl$_3$, δ): 1.98–2.09 (2H, m), 2.79 (2H, t, J=7 Hz), 3.81 (2H, t, J=7 Hz), 4.51 (2H, s), 4.59 (2H, br s), 5.23 (2H, s), 7.18–7.54 (3H, m), 7.69–7.79 (4H, m), 7.82–7.95 (4H, m).

(4) To a suspension of 1,2,3,4-tetrahydro-1-phthalimidoacetyl-5-(phthalimidoacetoxymethyl)quinoline (150 mg) in ethanol (3 ml) was added hydrazine monohydrate (83.8 mg), and the mixture was refluxed for 3 hours. After cooling, the insoluble material was filtered off, and the filtrate was concentrated in vacuo. To the residue was added dichloromethane, and the insoluble material was filtered off. The filtrate was concentrated in vacuo to give 1-glycyl-1,2,3,4-tetrahydro-5-hydroxymethylquinoline (60 mg) as pale yellow oil.

NMR (CDCl$_3$, δ): 1.93–2.04 (2H, m), 2.78 (2H, t, J=7 Hz), 3.55 (2H, s), 3.80–3.93 (4H, m), 4.70 (2H, s), 7.13–7.29 (3H, m).

(5) 1,2,3,4-Tetrahydro-5-hydroxymethyl-1-[4-(methylcarbamoyl)cinnamoylglycyl]quinoline was obtained according to a similar manner to that of Example 1-(4).

NMR (CDCl$_3$—CD$_3$OD, δ): 1.91–2.09 (2H, m), 2.80 (2H, br t, J=7 Hz), 3.00 (3H, s), 3.73–3.88 (2H, m), 4.23–4.35 (2H, m), 4.68 (2H, s), 6.57 (1H, d, J=15 Hz), 7.20–7.34 (3H, m), 7.51–7.64 (3H, m), 7.75 (2H, d, J=8 Hz).

(6) 1,2,3,4-Tetrahydro-5-methanesulfonyloxymethyl-1-[4-(methylcarbamoyl)cinnamoylglycyl]quinoline was obtained according to a similar manner to that of Example 24-(3).

NMR (CDCl$_3$, δ): 2.00–2.13 (2H, m), 2.79–2.90 (2H, m), 2.99 (3H, s), 3.03 (3H, d, J=5 Hz), 3.75–3.87 (2H, m), 4.28–4.36 (2H, m), 5.27 (2H, s), 6.18 (1H, br d, J=5 Hz), 6.55 (1H, d, J=15 Hz), 6.79 (1H, br s), 7.22–7.34 (3H, m), 7.56 (2H, d, J=8 Hz), 7.62 (1H, br d, J=15 Hz), 7.76 (2H, d, J=8 Hz).

(7) 1,2,3,4-Tetrahydro-1-[4-(methylcarbamoyl)cinnamoylglycyl]-5-(2-methylquinolin-8-yloxymethyl)quinoline was obtained accoridng to a similar manner to that of Example 21.

mp: 162° C. (dec.); NMR (CDCl$_3$, δ): 1.99–2.11 (2H, m), 2.77 (3H, s), 2.87–2.98 (2H, m), 3.00 (3H, d, J=5 Hz), 3.75–3.90 (2H, m), 4.29–4.37 (2H, m), 5.37 (2H, s), 6.18 (1H, br d, J=5 Hz), 6.54 (1H, d, J=15 Hz), 6.79 (1H, br s), 7.01 (1H, d, J=8 Hz), 7.18–7.44 (6H, m), 7.53 (2H, d, J=8 Hz), 7.60 (1H, br d, J=15 Hz), 7.75 (2H, d, J=8 Hz), 8.01 (1H, d, J=8 Hz).

Example 53

(1) To a solution of 2-(2,4-dichlorophenyl)-1,3-dioxolane (31.9 g) in tetrahydrofuran (220 ml) was added dropwise 1.6M n-butyllithium in hexane (110 ml) at –60 to –50° C. in a dry ice-acetone bath, and the mixture was stirred at –50° C. After 1 hour, to the reaction mixture was added N,N-dimethylformamide (56.4 ml). After 15 minutes, the mixture was stirred at ambient temperature for 1 hour then water (200 ml) was added thereto. The mixture was extracted with ethyl acetate (100 ml) twice, the organic layer was washed with water 3 times, dried over magnesium sulfate and evaporated in vacuo. The residue was purified by flash silica gel chromatography eluted with n-hexane-ethyl acetate (10:1, V/V) and crystallized with diisopropyl ether to give 2,6-dichloro-3-(1,3-dioxolan-2-yl)benzaldehyde (4.91 g) as colorless crystals.

mp: 96–98° C.; NMR (CDCl$_3$, δ): 4.04–4.20 (4H, m), 6.16 (1H, s), 7.44 (1H, d, J=8 Hz), 7.75 (1H, d, J=8 Hz), 10.05 (1H, s)

(2) To a suspension of 2,6-dichloro-3-(1,3-dioxolan-2-yl)-benzaldehyde (3.9 g) in methanol (19.5 ml) was added sodium borohydride (299 mg) under nitrogen atmosphere, and the mixture was stirred for 1 hour under ice-cooling. To the mixture was added water, and the mixture was extracted with ethyl acetate. The extract was washed with water and brine, dried over magnesium sulfate and evaporated in vacuo. The residue was crystallized from diisopropyl ether to give 2,6-dichloro-3-(1,3-dioxolan-2-yl)-1-hydroxymethylbenzene (3.69 g) as colorless crystals.

mp: 82–85° C.; NMR (CDCl$_3$, δ): 2.08 (1H, t, J=7 Hz), 4.02–4.18 (4H, m), 5.00 (2H, d, J=7 Hz), 6.13 (1H, s), 7.38 (1H, d, J=8 Hz), 7.54 (1H, d, J=8 Hz).

(3) 2,6-Dichloro-3-(1,3-dioxolan-2-yl)-1-(methanesulfonyloxymethyl)benzene was obtained according to a similar manner to that of Example 24-(3).

NMR (CDCl$_3$, δ): 3.10 (3H, s), 4.04–4.19 (4H, m), 5.58 (2H, s), 6.12 (1H, s), 7.41 (1H, d, J=8 Hz), 7.65 (1H, d, J=8 Hz).

(4) 8-[2,6-Dichloro-3-(1,3-dioxolan-2-yl)benzyloxy]-2-methylquinoline was obtained according to a similar manner to that of Example 21.

mp: 82–85° C.; NMR (CDCl$_3$, δ): 2.74 (3H, s), 4.02–4.18 (4H, m), 5.64 (2H, s), 6.17 (1H, s), 7.21–7.45 (5H, m), 7.59 (1H, d, J=8 Hz), 8.00 (1H, d, J=8 Hz).

(5) A solution of 8-[2,6-dichloro-3-(1,3-dioxolan-2-yl)benzyloxy]-2-methylquinoline (3.0, g) in 80% acetic acid (30 ml) was heated at 60° C. for 2 hours. The cooled reaction mixture was concentrated in vacuo, and aqueous sodium bicarbonate solution was added thereto. The mixture was extracted with chloroform, and the organic, layer was washed with water, dried over magnesium sulfate and evaporated in vacuo. The residue was crystallized from ethyl acetate to give 8-(2,6-dichloro-3-formylbenzyloxy)-2-methylquinoline (2.28 g) as colorless crystals.

mp: 184–186° C.; NMR (CDCl$_3$, δ): 2.73 (3H, s), 5.69 (2H, s), 7.23–7.52 (5H, m), 7.89 (1H, d, J=8 Hz), 8.02 (1H, d, J=8 Hz).

(6) 8-(2,6-Dichloro-3-carboxybenzyloxy)-2-methylquinoline was obtained according to a similar manner to that of Example 30-(1).

mp: 267–270° C.; NMR (DMSO-d$_6$, δ): 2.59 (3H, s), 5.48 (2H, s), 7.34–7.57 (4H, m), 7.68 (1H, d, J=8 Hz), 7.81 (1H, d, J=8 Hz), 8.20 (1H, d, J=8 Hz).

(7) A suspension of 8-(2,6-dichloro-3-carboxybenzyloxy)-2-methylquinoline (200 mg), 1-(tert-butoxycarbonyl)piperazine (109 mg), 1-ethyl-3-(3-dimethylaminopropyl)carbodiimide hydrochloride (127 mg) and 1-hydroxybenzotriazole (104 mg) in N,N-dimethylformamide (2 ml) was stirred for 2 hours at ambient temperature. To the reaction mixture was added saturated sodium bicarbonate solution, and the mixture was extracted with ethyl acetate. The extract was washed with water and brine, dried over magnesium sulfate and evaporated in vacuo. The residue was purified by preparative thin layer chromatography (n-hexane-ethyl acetate) to give 8-[3-[4-(tert-butoxycarbonyl)piperazine-1-carbonyl]-2,6-dichlorobenzyloxy]-2-methylquinoline (270 mg) as colorless amorphous.

NMR (CDCl$_3$, δ): 1.46 (9H, s), 2.72 (3H, s), 3.11–3.93 (8H, m), 5.62 (2H, s), 7.18–7.47 (6H, m), 8.01 (1H, d, J=8 Hz).

(8) A mixture of 8-[3-[4-(tert-butoxycarbonyl)piperazine-1-carbonyl]-2,6-dichlorobenzyloxy]-2-methylquinoline (260 mg) and 4N solution of hydrogen chloride in ethyl acetate (2 ml) was stirred for 40 minutes at ambient temperature. The mixture was concentrated in vacuo, and the residue was crystallized from acetonitrile to give 8-[2,6- dichloro-3-(piperazine-1-carbonyl)benzyloxy]-2-methylquinoline dihydrochloride (227 mg) as pale yellow crystals.

mp: 195–197° C.; NMR (DMSO-$d_6$, δ): 2.85 (3H, s), 2.99–4.00 (8H, m), 5.50 (1H, d, J=10 Hz), 5.64 (1H, d, J=10 Hz), 7.63 (1H, d, J=8 Hz), 7.70–7.87 (4H, m), 8.80 (1H, br s), 9.48–9.61 (2H, m).

Example 54

To a solution of 8-[2,6-dichloro-3-(piperazine-1-carbonyl)benzyloxy]-2-methylquinoline dihydrochloride (60 mg), 4-(methylcarbamoyl)cinnamic acid (26.9 mg) and 1-hydroxybenzotriazole (22.6 mg) in N,N-dimethylformamide (0.6 ml) was added 1-ethyl-3-(3-dimethylaminopropyl)carbodiimide (27.4 mg) at ambient temperature, and the mixture was stirred for 3 hours at the same temperature. The reaction mixture was poured into water and extracted with ethyl acetate. The extract was washed with saturated sodium bicarbonate solution, water and brine, dried over magnesium sulfate and evaporated in vacuo. The residue was purified by preparative thin layer chromatography (chloroform:methanol=10:1, V/V) to give 8-[2,6-dichloro-3-[4-[4-(methylcarbamoyl)cinnamoyl] piperazine-1-carbonyl]benzyloxy]-2-methylquinoline (73 mg) as colorless amorphous.

NMR (CDCl$_3$, δ): 2.66 (3H, br s), 2.99 (3H, br s), 3.18–3.40 (2H, m), 3.49–4.06 (6H, m), 5.63 (2H, br s), 6.30 (0.5H, br s), 6.65 (0.5H, br s), 6.90 (1H, br s), 7.20–7.62 (8H, m), 7.69 (1H, br d, J=15 Hz), 7.79 (2H, br d, J=8 Hz), 8.02 (1H, br d, J=8 Hz).

Example 55

8-[2,6-Dichloro-3-[4-[4-(methylcarbamoyl)benzoyl]-piperazine-1-carbonyl]benzyloxy]-2-methylquinoline was obtained from 8-[2,6-dichloro-3-(piperazine-1-carbonyl) benzyloxy]-2-methylquinoline dihydrochloride and 4-(methylcarbamoyl)benzoic acid according to a similar manner to that of Example 54.

NMR (CDCl$_3$, δ): 2.70 (3H, br s), 3.03 (3H, br d, J=5 Hz), 3.18–4.10 (8H, m), 5.63 (2H, s), 6.25 (1H, br s), 7.20–7.51 (8H, m), 7.83 (2H, br d, J=8 Hz), 8.01 (1H, br d, J=8 Hz).

Example 56

(1) To a suspension of 4-(methylcarbamoyl)aniline (1.0 g) in 1,4-dioxane (10 ml) were added 1N sodium hydroxide solution (13.4 ml) and phenyl chloroformate (1.26 g) under ice-cooling, and the mixture was stirred for 2 hours at ambient temperature. The reaction mixture was poured into water and extracted with a mixture of chloroform and methanol. The extract was washed with water, dried over magnesium sulfate and evaporated in vacuo. The residue was crystallized from ethyl acetate to give phenyl 4-(methylcarbamoyl)phenylcarbamate (1.70 g) as pale yellow crystals.

mp: 190–192° C.; NMR (DMSO-$d_6$, δ): 2.70 (1H, d, J=5 Hz), 2.77 (2H, d, J=5 Hz), 5.55 (0.6H, br s), 6.51 (0.9H, d, J=8 Hz), 6.71–6.80 (1.1H, m), 7.15 (0.8H, t, J=8 Hz), 7.20–7.31 (1.8H, m), 7.43 (1.2H, t, J=8 Hz), 7.50–7.60 (2H, m), 7.80 (1.2H, d, J=8 Hz), 7.92 (0.3H, br d, J=5 Hz), 8.31 (1H, br s), 9.30 (0.4H, s).

(2) To a solution of 8-[2,6-dichloro-3-(piperazine-1-carbonyl)benzyloxy]-2-methylquinoline dihydrochloride (60 mg) and triethylamine (48.3 mg) in N,N-dimethylformamide (0.6 ml) was added phenyl 4-(methylcarbamoyl)phenylcarbamate (33.8 mg), and the mixture was stirred for 2 hours at 80° C. The reaction mixture was poured into water and extracted with ethyl acetate. The extract was washed with water and brine, dried over magnesium sulfate and evaporated in vacuo. The residue was purified by preparative thin layer chromatography (chloroform:methanol=10:1, V/V) to give 8-[2,6-dichloro- 3-[4-[4-(methylcarbamoyl)phenylcarbamoyl] piperazine-1-carbonyl]benzyloxy]-2-methylquinoline (61 mg) as colorless amorphous.

NMR (CDCl$_3$, δ): 2.51 (3H, br s), 2.90 (3H, br d, J=5 Hz), 2.93–3.01 (2H, m), 3.20–3.66 (6H, m), 5.51 (1H, d, J=10 Hz), 5.61 (1H, d, J=10 Hz), 6.79 (1H, br s), 7.11 (1H, d, J=8 Hz), 7.21–7.39 (3H, m), 7.42–7.53 (4H, m), 7.70 (2H, br d, J=8 Hz), 7.84 (1H, br s), 8.07 (1H, br d, J=8 Hz).

Example 57

(1) To a solution of 3-(phthalimido)propionic acid (6.0 g) and triethylamine (2.77 g) in benzene (60 ml) was added diphenylphosphoryl azide (7.53 g), and the mixture was refluxed for 40 minutes. Tert-butanol (4.23 g) was added thereto, and the mixture was refluxed overnight. After cooling, the reaction mixture was washed with saturated sodium bicarbonate solution, water and brine, dried over magnesium sulfate and evaporated in vacuo. The residue was purified by flash chromatography (n-hexane-ethyl acetate) and crystallized from diisopropyl ether to give N-(2-tert-butoxycarbonylaminoethyl)phthalimide (5.74 g) as colorless crystals.

mp: 143–145° C.; NMR (CDCl$_3$, δ): 1.35 (9H, s), 3.35–3.49 (2H, m), 3.79–3.89 (2H, m), 4.82 (1H, br s), 7.68–7.78 (2H, m), 7.80–7.90 (2H, m).

(2) A mixture of N-(2-tert-butoxycarbonylaminoethyl) phthalimide (2.5 g) and 4N solution of hydrogen chloride in ethyl acetate (25 ml) was stirred for 1 hour at ambient temperature. The resulting precipitates were collected by filtration and washed with ethyl acetate to give N-(2-aminoethyl)phthalimide hydrochloride (1.89 g) as colorless crystals.

mp: 276–280° C.; NMR (DMSO-$d_6$, δ): 3.07 (2H, t, J=7 Hz), 3.84 (2H, t, J=7 Hz), 7.81–7.94 (4H, m), 8.04 (2H, br s).

(3) To a suspension of 8-(2,6-dichloro-3-carboxybenzyloxy)-2-methylquinoline (800 mg), 1-ethyl-3-(3-dimethylaminopropyl)carbodiimide (508 mg) and 1-hydroxybenzotriazole (388 mg) in N,N-dimethylformamide (8 ml) was added N-(2-aminoethyl) phthalimide hydrochloride (551 mg), and the mixture was stirred for 3 hours at ambient temperature. To the reaction mixture was added saturated sodium bicarbonate solution, and the mixture was extracted with chloroform. The insoluble material was filtered off, and the filtrate was washed with water, dried over magnesium sulfate and evaporated in vacuo. The residue was crystallized from ethyl acetate to give 8-[2,6-dichloro-3-[N-(2-phthalimidoethyl) carbamoyl]benzyloxy]-2-methylquinoline (1.04 g) as colorless crystals.

mp: 210–212° C.; NMR (CDCl$_3$, δ): 2.70 (3H, br s), 3.70–3.80 (2H, m), 3.93–4.01 (2H, m), 6.75 (1H, br s), 7.20–7.31 (2H, m), 7.35–7.49 (4H, m), 7.66–7.74 (2H, m), 7.80–7.88 (2H, m), 8.01 (1H, br d, J=8 Hz).

(4) To a solution of 8-[2,6-dichloro-3-[N-(2-phthalimidoethyl)carbamoyl]benzyloxy]-2-methylquinoline (390 mg) in N,N-dimethylformamide (4 ml) was added sodium hydride (32.1 mg) under ice-cooling, and the mixture was stirred for 15 minutes at the same temperature. Methyl iodide (114 mg) was added thereto under ice-cooling, and the mixture was stirred for 15 minutes at the same temperature and for 2 hours at ambient temperature. To the mixture was added water, and the mixture was extracted with ethyl acetate. The extract was washed with water, dried over magnesium sulfate and evaporated in vacuo. The residue was purified by flash chromatography (chloroform:ethyl acetate=3:1, V/V) to give 8-(2,6-dichloro-3-[N-methyl-N-(2-phthalimidoethyl)carbamoyl]benzyloxy]-2-methylquinoline (360 mg) as colorless amorphous.

NMR (CDCl$_3$, δ): 2.71 (3H, br s), 2.89 (2.2H, s), 3.17 (0.8H, s), 3.33–4.32 (4H, m), 5.55 (1H, d, J=10 Hz), 5.60 (1H, d, J=10 Hz), 6.95 (0.4H, d, J=8 Hz), 7.15–7.45 (4.6H, m), 7.68–7.78 (2H, m), 7.81–7.89 (2H, m), 7.99 (1H, d, J=8 Hz).

(5) 8-[3-[N-(2-Aminoethyl)-N-methylcarbamoyl]-2,6-dichlorobenzyloxy]-2-methylquinoline was obtained according to a similar manner to that of Example 51-(5).

NMR (CDCl$_3$, δ): 2.72 (3H, br s), 2.79–2.90 (2.7H, m), 2.99 (1.2H, t, J=7 Hz), 3.12 (1.3H, s), 3.15–3.30 (0.6H, m), 3.34–3.48 (0.6H, m), 3.79–3.91 (0.6H, m), 5.61 (1H, br s), 5.65 (1H, br s), 7.20–7.31 (3H, m), 7.34–7.48 (3H, m), 8.01 (1H, d, J=8 Hz).

(6) 8-[2,6-Dichloro-3-[N-methyl-N-[2-[4-(methylcarbamoyl)cinnamoylamino]ethyl]carbamoyl]benzyloxy]-2-methylquinoline was obtained according to a similar manner to that of Example 2-(4).

NMR (CDCl$_3$, δ): 2.56 (1.5H, s), 2.67 (1.5H, s), 2.88–2.99 (4.5H, m), 3.21 (1.5H, s), 3.35–3.80 (3.5H, m), 3.94 (0.5H, m), 5.46 (0.5H, d, J=10 Hz), 5.51 (0.5H, d, J=10 Hz), 5.59 (1H, br s), 6.40 (0.5H, d, J=15 Hz), 6.47 (0.5H, d, J=15 Hz), 6.52 (0.4H, br s), 6.82 (0.6H, br s), 7.14–7.78 (12H, m), 8.00 (0.5H, d, J=8 Hz), 8.08 (0.5H, d, J=8 Hz).

Example 58

8-[2,6-Dichloro-3-[N-methyl-N-[2-[4-(methylcabamoyl)benzamido]ethyl]carbamoyl]benzyloxy]-2-methylquinoline was obtained from 8-[3-[N-(2-aminoethyl)-N-methylcarbamoyl]-2,6-dichlorobenzyloxy]-2-methylquinoline and (methylcarbamoyl)benzoic acid according to a similar manner that of Example 2-(4).

NMR (CDCl$_3$, δ): 2.40 (3H, br s), 2.68 (2H, d, J=5 Hz), 2.71 (1H, br s), 2.91 (2H, s), 3.28 (1H, s), 3.42–4.03 (4H, m), 5.48 (0.5H, br s), 5.59 (1.5H, br s), 5.46 (0.5H, d, J=10 Hz), 5.51 (0.5H, d, J=10 Hz), 5.59 (1H, br s), 6.73 (0.5H, br s), 6.87 (0.5H, br s), 6.95 (0.6H, d, J=8 Hz), 7.21–7.30 (2H, m), 7.41–7.51 (2.4H, m), 7.63 (1H, br t, J=8 Hz), 7.72 (2H, br d, J=8 Hz), 7.80 (2H, br d, J=8 Hz), 8.03 (1H, d, J=8 Hz), 8.19 (1H, br s).

Example 59

8-[2,6-Dichloro-3-[N-methyl-N-[2-[N'-[4-(methylcarbamoyl)phenyl]ureido]ethyl]carbamoyl]benzyloxy]-2-methylquinoline was obtained from 8-[3-[N-(2-aminoethyl)-N-methylcarbamoyl]-2,6-dichlorobenzyloxy]-2-methylquinoline and phenyl 4-(methylcarbamoyl)phenylcarbamate according to a similar manner to that of Example 5.

mp: 201–204° C.; NMR (DMSO-d$_6$, δ): 2.58 (3H, s), 2.75 (1.5H, d, J=5 Hz), 2.78 (1.5H, d, J=5 Hz), 2.83 (1.5H, s), 3.04 (1.5H, s), 3.15–3.71 (4H, m), 5.30 (1H, br s), 5.47 (1H, br s), 6.32 (1H, br s), 7.20 (0.6H, d, J=8 Hz), 7.32–7.55 (6.9H, m), 7.64 (0.5H, d, J=8 Hz), 7.70 (1H, d, J=8 Hz), 7.75 (1H, d, J=8 Hz), 8.17–8.29 (2H, m), 8.75 (0.5H, s), 8.87 (0.5H, s).

Example 60

(1) 8-[3-[N-Benzyl-N-(2-phthalimidoethyl)carbamoyl]-2,6-dichlorobenzyloxy)-2-methylquinoline was obtained from 8-[2,6-dichloro-3-[N-(2-phthalimidoethyl)carbamoyl]benzyloxy]-2-methylquinoline and benzyl bromide according to a similar manner to that of Example 57-(4).

NMR (CDCl$_3$, δ): 2.68 (1.5H, s), 2.71 (1.5H, br s), 3.31–3.43 (0.7H, m), 3.60–4.20 (4.3H, m), 4.37 (1H, br s), 4.47 (0.5H, d, J=15 Hz), 5.35 (0.5H, d, J=15 Hz), 5.58 (2H, s), 7.02–7.44 (6H, m), 7.65–7.84 (4H, m), 7.97 (1H, d, J=8 Hz).

(2) 8-[3-[N-(2-Aminoethyl)-N-benzylcarbamoyl]-2,6-dichlorobenzyloxy]-2-methylquinoline was obtained according to a similar manner to that of Example 51-(5).

NMR (CDCl$_3$, δ): 2.68–2.78 (4H, m), 2.95 (1H, br t, J=7 Hz), 3.38–3.20 (1.5H, m), 3.91–4.04 (0.5H, m), 4.32 (0.6H, d, J=15 Hz), 4.47 (0.6H, d, J=15 Hz), 4.57 (0.4H, d, J=15 Hz), 5.09 (0.4H, d, J=15 Hz), 5.59–5.71 (2H, m), 7.71 (1H, br d, J=8 Hz), 7.19–7.48 (10H, m), 8.01 (1H, br d, J=8 Hz).

(3) 8-[3-[N-Benzyl-N-[2-[4-(methylcarbamoyl)cinnamoylamino]ethyl]carbamoyl]-2,6-dichlorobenzyloxy]-2-methylquinoline was obtained according to a similar manner to that of Example 2-(4).

NMR (CDCl$_3$, δ): 2.53 (1.5H, s), 2.66 (1.5H, s), 2.88 (1.5H, br d, J=5 Hz), 3.97 (1.5H, d, J=5 Hz), 3.25–3.75 (3.5H, m), 4.02–4.14 (0.5H, m), 4.34 (0.5H, d, J=15 Hz), 4.47 (0.5H, d, J=15 Hz), 4.77 (0.5H, d, J=15 Hz), 5.15 (0.5H, d, J=15 Hz), 5.49 (1H, s), 5.61 (1H, s), 6.39–6.49 (1.5H, m), 6.81 (0.5H, br s), 7.08–7.61 (10H, m), 7.69–7.78 (2H, m), 7.98 (1H, d, J=8 Hz), 8.08 (1H, d, J=8 Hz).

Example 61

8-[3-[N-Benzyl-N-[2-[N'-[3-(4-pyridylcarbamoyl)phenyl]-ureido]ethyl]carbamoyl]-2,6-dichlorobenzyloxy]-2-methylquinoline was obtained from 8-[3-[N-(2-aminoethyl)-N-benzylcarbamoyl]-2,6-dichlorobenzyloxy]-2-methylquinoline and phenyl 3-(4-pyridylcarbamoyl)phenylcarbamate according to a similar manner to that of Example 5.

NMR (CDCl$_3$—CD$_3$OD, δ): 2.54 (2H, s), 2.61 (1H, s), 3.19–3.34 (2H, m), 3.45–3.64 (1.5H, m), 3.91–4.06 (0.5H, m), 4.39 (0.3H, d, J=15 Hz), 4.50 (0.3H, d, J=15 Hz), 4.68 (0.7H, d, J=15 Hz), 4.95 (0.7H, d, J=15 Hz), 5.38 (0.7H, d, J=10 Hz), 5.46 (0.3H, d, J=10 Hz), 5.50 (0.3H, d, J=10 Hz), 5.58 (0.7H, d, J=10 Hz), 6.61 (0.5H, br d, J=8 Hz), 7.03–7.62 (19.5H, m), 7.70 (2H, br d, J=7 Hz), 7.84 (0.6H, br s), 7.96 (0.4H, br s), 7.99 (0.3H, d, J=8 Hz), 8.08 (0.7H, d, J=8 Hz), 8.37–8.44 (2H, m).

Example 62

(1) To a suspension of 8-[2,6-dichloro-3-glycylaminobenzyloxy]-2-methylquinoline (2.14 g) in tetrahydrofuran (21 ml) was dropwise added 2M boranemethylsulfide complex in tetrahydrofuran (5.48 ml) at 0° C. under nitrogen atmosphere, and the mixture was stirred for 15 minutes at the same temperature and refluxed for 6 hours. After cooling, the mixture was adjusted to pH 1 with 1N hydrochloric acid and refluxed for 30 minutes. The mixture was neutralized with saturated sodium bicarbonate solution and extracted with chloroform. The extract was washed with water and brine, dried over magnesium sulfate and evaporated in vacuo. The residue was purified by flash chromatography (chloroform) to give 8-[3-[N-(2-aminoethyl)amino]-2,6-dichlorobenzyloxy]-2-methylquinoline (525 mg) as colorless amorphous.

NMR (CDCl$_3$, δ): 2.73 (3H, s), 2.99 (2H, t, J=7 Hz), 3.24 (2H, q, J=7 Hz), 4.81 (1H, br t, J=7 Hz), 5.58 (2H, s), 6.65 (1H, d, J=8 Hz), 7.18–7.42 (5H, m), 8.00 (1H, d, J=8 Hz).

(2) 8-[2,6-Dichloro-3-[N-(2-[4-(dimethylcarbamoyl)cinnamoylamino]ethyl]amino]benzyloxy]-2-methylquinoline was obtained according to a similar manner to that of Example 2-(4).

NMR (CDCl$_3$, δ): 2.61 (3H, s), 2.94 (3H, br s), 3.09 (3H, br s), 3.22–3.34 (2H, m), 3.43–3.55 (2H, m), 5 4.69 (1H, br t, J=7 Hz), 5.48 (2H, s), 6.44 (1H, d, J=8 Hz), 6.69 (1H, d, J=15 Hz), 6.99 (1H, d, J=8 Hz), 7.21–7.49 (8H, m), 7.55 (1H, d, J=15 Hz), 8.05 (1H, d, J=8 Hz), 8.15 (1H, br s).

Example 63

(1) 1-[3-(tert-Butyldiphenylsilyloxymethyl)-2,4-dichlorophenyl]-2-[4-(ethoxycarbonyl)cinnamoylaminomethyl]pyrrole was obtained from 2-aminomethyl-1-[3-(tert-butyldiphenylsilyloxymethyl)-2,4-dichlorophenyl]pyrrole and 4-(ethoxycarbonyl)cinnamic acid according to a similar manner to that of Example 1-(4).

NMR (CDCl$_3$, δ): 1.03 (9H, s), 1.41 (3H, t, J=7 Hz), 4.33 (2H, d, J=5 Hz), 4.40 (2H, q, J=7 Hz), 4.88 (2H, br s), 5.57 (1H, br s), 6.21–6.34 (3H, m), 6.68 (1H, br s), 7.27 (1H, d, J=8 Hz) 7.30–7.52 (10H, m), 7.66–7.75 (4H, m), 7.99 (2H, d, J=8 Hz).

(2) 1-[2,4-Dichloro-3-hydroxymethylphenyl]-2-[4-(ethoxycarbonyl)cinnamoylaminomethyl]pyrrole was obtained according to a similar manner to that of Example 1-(5).

NMR (CDCl$_3$, δ): 1.40 (3H, t, J=7 Hz), 2.59 (1H, t, J=7 Hz), 4.30–4.54 (4H, m), 4.93–5.01 (2H, m), 5.60 (1H, br s), 6.25 (1H, d, J=15 Hz), 6.28–6.34 (2H, m), 6.70 (1H, br s), 7.25 (1H, d, J=8 Hz), 7.36–7.55 (10H, m), 8.02 (2H, d, J=8 Hz).

(3) 1-[2,4-Dichloro-3-[4-(imidazol-1-yl)-2-methylquinolin-8-yloxymethyl]phenyl]-2-[4-(ethoxycarbonyl)cinnamoylaminomethyl]pyrrole was obtained according to a similar manner to that of Example 23-(3).

NMR (CDCl$_3$, δ): 1.37 (3H, t, J=7.5 Hz), 2.69 (3H, s), 4.30–4.45 (4H, m), 5.55 (1H, s), 5.57 (1H, S), 6.14 (1H, br s), 6.29 (1H, t, J=2 Hz), 6.34 (1H, br s), 6.40 (1H, d, J=15 Hz), 6.70 (1H, d, J=2 Hz), 7.19 (1H, s), 7.28–7.53 (9H, m), 7.78–7.85 (3H, m).

(4) 2-(4-Carboxycinnamoylaminomethyl)-1-[2,4-dichloro-3-[4-(imidazol-1-yl)-2-methylquinolin-8-yloxymethyl]phenyl]pyrrole was obtained according to a similar manner to that of Example 16-(2).

mp: 166–170° C.; NMR (DMSO-d$_6$, δ): 2.65 (3H, s), 4.11 (1H, br dd, J=15, 5 Hz), 4.28 (1H, br dd, J=15, 5 Hz), 5.44 (1H, s), 5.46 (1H, s), 6.19–6.27 (2H, m), 6.70 (1H, d, J=8 Hz), 6.88 (1H, m), 7.22 (1H, s), 7.29 (1H, br d, J=8 Hz), 7.34–7.42 (2H, m), 7.50 (1H, t, J=8 Hz), 7.56 (1H, s), 7.61–7.69 (4H, m), 7.73 (1H, d, J=8 Hz), 7.95 (2H, d, J=8 Hz), 8.09 (1H, s), 8.34 (1H, br t, J=5 Hz).

its sodium salt

NMR (DMSO-d$_6$, δ): 2.64 (3H, s), 4.09 (1H, br dd, J=15, 5 Hz), 4.30 (1H, br dd, J=15, 5 Hz), 5.35 (1H, d, J=10 Hz), 5.41 (1H, d, J=10 Hz), 6.18–6.26 (2H, m), 6.57 (1H, d, J=15 Hz), 6.88 (1H, br s), 7.20–7.32 (4H, m), 7.40 (2H, br d, J=8 Hz), 7.49 (1H, t, J=8 Hz), 7.54 (1H, s), 7.61–7.69 (2H, m), 7.72 (1H, d, J=8 Hz), 7.85 (2H, d, J=8 Hz), 8.09 (1H, s), 8.21 (1H, br t, J=5 Hz).

Example 64

(1) 1-[2,4-Dichloro-3-[2-methyl-4-(morpholino)quinolin-8-yloxymethyl]phenyl]-2-[4-(ethoxycarbonyl)cinnamoylaminomethyl]pyrrole was obtained from 1-(2,4-dichloro-3-hydroxymethylphenyl)-2-[4-(ethoxycarbonyl)-cinnamoylaminomethyl]pyrrole and 8-hydroxy-2-methyl-4-(morpholino)quinoline according to a similar manner to that of Example 23-(3).

NMR (CDCl$_3$, δ): 1.38 (3H, t, J=7.5 Hz), 2.52 (3H, s), 3.10–3.26 (4H, m), 3.93–4.02 (4H, m), 4.22 (1H, br dd, J=15, 5 Hz), 4.35 (2H, q, J=7 Hz), 4.53 (1H, br dd, J=15, 5 Hz), 5.49 (1H, d, J=10 Hz), 5.57 (1H, d, J=10 Hz), 6.21–6.31 (2H, m), 6.39 (1H, d, J=15 Hz), 7.10–7.24 (2H, m), 7.32–7.52 (4H, m), 7.66 (1H, br d, J=8 Hz), 7.73 (2H, d, J=8 Hz), 8.03 (1H, d, J=8 Hz).

(2) 2-(4-Carboxycinnamoylaminomethyl)-1-[2,4-dichloro-3-[2-methyl-4-(morpholino)quinolin-8-yloxymethyl]phenyl]pyrrole was obtained according to a similar manner to that of Example 16-(2).

mp: 174–180° C.; NMR (DMSO-d$_6$, δ): 2.54 (3H, br s), 3.18–3.20 (4H, m), 3.81–3.89 (4H, m), 4.07 (1H, m), 4.20 (1H, m), 4.70 (1H, d, J=7 Hz), 5.30 (0.5H, t, J=5 Hz), 5.38 (1H, br s), 6.17–6.26 (3H, m), 6.68 (1H, d, J=15 Hz), 6.77 (0.25H, d, J=2 Hz) 6.87 (0.75H, d, J=2 Hz), 6.94 (0.25H, br s), 7.36 (1H, br d, J=15 Hz), 7.45 (0.25H, d, J=8 Hz), 7.54–7.62 (4.75H, m), 7.97 (2H, d, J=8 Hz), 8.34 (1H, s).

its sodium salt

NMR (DMSO-d$_6$, δ) 2.50 (3H, br s), 3.07–3.13 (4H, m), 3.80–3.89 (4H, m), 4.07 (1H, m), 4.30 (0.5H, s), 5.28 (0.5H, s), 5.30 (0.5H, s), 6.16–6.24 (2H, m), 6.55 (0.4H, d, J=15 Hz), 6.56 (0.6H, d, J=15 Hz), 6.76 (0.4H, br s), 6.87 (0.6H, br s), 6.91 (0.6H, s), 6.99 (0.6H, br d, J=8 Hz), 7.23–7.48 (4H, m), 7.54–7.65 (1.8H, m), 7.71 (0.6H, d, J=8 Hz), 7.82 (0.4H, d, J=8 Hz), 7.77 (0.6H, d, J=8 Hz), 8.20 (1H, br s).

Example 65

(1) 1-[3-(tert-Butyldiphenylsilyloxymethyl)-2,4-dichlorophenyl]-2-[(E)-3-[6-(ethoxycarbonyl)pyridin-3-yl]acryloylaminomethyl]pyrrole was obtained from 2-aminomethyl-1-[3-(tert-butyldiphenylsilyloxymethyl)-2,4-dichlorophenyl]pyrrole and (E)-3-[6-(ethoxycarbonyl)pyridin-3-yl]acrylic acid according to a similar manner to that of Example 1-(4).

NMR (CDCl$_3$, δ): 1.01 (9H, s), 1.46 (3H, t, J=7 Hz), 4.32 (2H, br t, J=5 Hz), 4.49 (2H, q, J=7 Hz), 4.89 (2H, br s), 5.62 (1H, br s), 6.27–6.38 (3H, m), 6.68 (1H, d, J=2 Hz), 7.25 (1H, d, J=8 Hz), 7.30–7.45 (8H, m), 7.50 (1H, d, J=15 Hz), 7.65–7.74 (4H, m), 7.78 (1H, dd, J=8, 2 Hz), 8.06 (1H, d, J=8 Hz), 8.77 (1H, d, J=2 Hz).

(2) 1-(2,4-Dichloro-3-hydroxymethylphenyl)-2-[(E)-3-[6-(ethoxycarbonyl)pyridin-3-yl]acryloylaminomethyl]pyrrole was obtained according to a similar manner to that of Example 1-(5).

NMR (CDCl$_3$, δ): 1.44 (3H, t, J=7 Hz), 2.59 (1H, br t, J=7 Hz), 4.34 (1H, dd, J=17, 5 Hz), 4.42–4.57 (3H, m), 4.92–5.00 (2H, m), 5.68 (1H, br s), 6.25–6.68 (3H, m), 6.69 (1H, d, J=2 Hz), 7.25 (1H, d, J=8 Hz), 7.39 (1H, d, J=8 Hz), 7.50 (1H, d, J=15 Hz), 7.88 (1H, dd, J=8, 2 Hz), 8.12 (1H, d, J=8 Hz), 8.82 (1H, br s).

(3) 1-[2,4-Dichloro-3-[4-(imidazol-1-yl)-2-methylquinolin-8-yloxymethyl]phenyl]-2-[(E)-3-[6-(ethoxycarbonyl)pyridin-3-yl]acryloylaminomethyl]pyrrole was obtained accoridng to a similar manner to that of Example 23-(3).

NMR (CDCl$_3$, δ): 1.42 (3H, t, J=7.5 Hz), 2.71 (3H, s), 4.40–4.50 (4H, m), 5.57 (1H, d, J=10 Hz), 5.63 (1H, d, J=10 Hz), 6.14 (1H, br s), 6.27–6.37 (2H, m), 6.59 (1H, d, J=15 Hz), 6.70 (1H, br s), 7.20–7.56 (9H, m), 7.74 (1H, dd, J=8, 2 Hz), 7.82–7.90 (2H, m), 8.68 (1H, br s).

(4) 2-[(E)-3-(6-Carboxypyridin-3-yl)acryloylaminomethyl]-1-[2,4-dichloro-3-[4-(imidazol-1-yl)-2-methylquinolin-8-yloxymethyl]phenyl]pyrrole was obtained according to a similar manner to that of Example 16-(2).

NMR (CDCl$_3$—CD$_3$OD, δ): 2.64 (3H, br s), 5.55–5.65 (2H, m), 6.26 (1H, br s), 6.37 (1H, br s), 6.55 (1H, br s), 6.67 (1H, br s), 7.24–7.58 (11H, m), 8.12 (1H, br s), 8.36 (1H, br s).

its sodium salt

NMR (DMSO-d$_6$, δ): 2.65 (3H, s), 4.11 (1H, br dd, J=5, 17 Hz), 4.28 (1H, br dd, J=5, 17 Hz), 5.44 (1H, s), 5.55 (1H, s), 6.18–6.27 (2H, m), 6.68 (1H, d, J=15 Hz), 6.88 (1H, d, J=2 Hz), 7.22 (1H, s), 7.28 (1H, d, J=8 Hz), 7.32–7.40 (2H, m), 7.49–7.58 (2H, m), 7.61–7.75 (3H, m), 7.88 (2H, br s), 8.10 (1H, s), 8.34 (1H, br t, J=5 Hz), 8.57 (1H, br s).

Example 66

(1) 1-[2,4-Dichloro-3-[2-methyl-4-(morpholino)quinolin-8-yloxymethyl]phenyl]-2-[(E)-3-[6-(ethoxycarbonyl)

pyridin-3-yl]acryloylaminomethyl]pyrrole was obtained from 1-(2,4-dichloro-3-hydroxymethylphenyl)-2-[(E)-3-[6-(ethoxycarbonyl)pyridin-3-yl]acryloylaminomethyl]pyrrole and 8-hydroxy-2-methyl-4-(morpholino)quinoline according to a similar manner to that of Example 23-(3).

NMR (CDCl$_3$, δ): 1.43 (3H, t, J=7.5 Hz), 2.53 (3H, s), 3.11–3.27 (4H, m), 3.95–4.02 (4H, m), 4.30–4.59 (4H, m), 5.51 (1H, d, J=10 Hz), 5.59 (1H, d, J=10 Hz), 6.29 (1H, t, J=2 Hz), 6.37 (1H, br s), 6.60 (1H, d, J=15 Hz), 6.65–6.72 (2H, m), 6.80 (1H, br s), 7.19 (1H, br d, J=8 Hz), 7.35–7.53 (5H, m), 7.64–7.72 (2H, m), 8.63 (1H, br s).

(2) 2-[(E)-3-(6-Carboxypyridin-3-yl)acryloylaminomethyl]-1-[2,4-dichloro-3-[2-methyl-4-(morpholino)quinolin-8-yloxymethyl]phenyl]pyrrole was obtained according to a similar manner to that of Example 16-(2).

NMR (CDCl$_3$—CD$_3$OD, δ): 2.03 (3H, s), 3.05–3.64 (4H, m), 3.90–4.07 (5H, m), 4.74 (1H, br s), 5.49 (1H, br d, J=10 Hz), 5.59 (1H, br d, J=10 Hz), 6.24 (1H, br s), 6.40 (1H, br s), 6.52 (1H, br d, J=15 Hz), 6.65 (1H, br s), 7.20–7.56 (8H, m), 7.63 (1H, br s), 8.29 (1H, br s).

its sodium salt

NMR (DMSO-d$_6$, δ): 2.46–2.56 (3H, overlapped with DMSO), 3.15–3.26 (4H, m), 3.80–3.90 (4H, m), 4.06–4.32 (2H, m), 5.38 (2H, br s), 6.16–6.27 (2H, m), 6.18 (1H, d, J=15 Hz), 6.86 (1H, br s), 6.90 (1H, br s), 7.12 (1H, m), 7.30–7.41 (2H, m), 7.56–7.65 (2H, m), 7.70 (1H, br d, J=8Hz), 7.90 (1H, br s), 8.35 (1H, br s), 8.58 (1H, br s).

What is claimed is:

1. A compound of the formula:

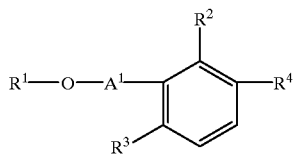

wherein:

$A^1$ is lower alkylene, $R^1$ is imidazopyridyl, substituted with a substituent(s) selected from the group consisting of halogen, lower alkyl, lower alkoxy, lower alkylamino and a heterocyclic group, $R^2$ is hydrogen, halogen or lower alkyl, $R^3$ is halogen or lower alkyl, and $R^4$ is carboxy, lower alkanoyl or a group of the formula:

—Q—A$^2$—R$^5$ or

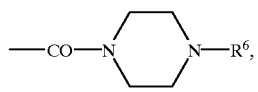

in which $R^2$ is amino, acylamino, cyano, hydroxy, hydroxyimino (lower) alkyl or acyl, $R^6$ is hydrogen or acyl, $A^2$ is lower alkylene or a single bond, and Q is lower alkenylene or a group of the formula:

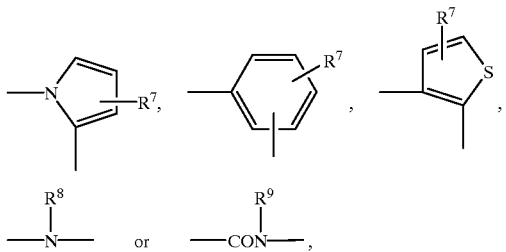

in which $R^7$ is hydrogen or halogen;

$R^8$ is hydrogen, or $R^8$ and $R^2$ are taken together to form lower alkylene; and $R^9$ is hydrogen, lower alkyl or ar(lower)alkyl; provided that $A^2$ is lower alkylene when $R^8$ is hydrogen, and pharmaceutically acceptable salts thereof.

2. A compound of claim 1, wherein:

$R^1$ is a group of the formula:

in which $R^5$ is amino or acylamino, $A^2$ is lower alkylene, and

Q is lower alkenylene or a group of the formula:

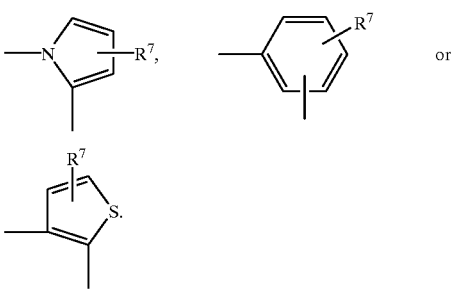

3. A compound of claim 2, wherein:

$R^1$ is 2-(lower alkyl)-3-(halo)imidazo[1,2-a]pyridin-8-yl, and $A^1$ is methylene.

4. A compound of claim 3, wherein:

$R^5$ is amino or a group of the formula:

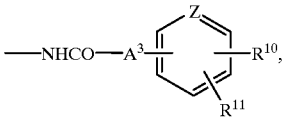

in which $A^3$ is —NH—, lower alkylene or lower alkenylene,

Z is CH or N, $R^{11}$ is hydrogen, lower alkyl or lower alkoxy, and $R^{10}$ is carboxy, esterified carboxy, heterocyclic(lower) alkenyl or a group of the formula:

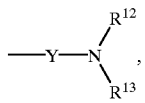

in which
$R^{12}$ is hydrogen, lower alkyl, heterocyclic(lower) alkyl, a heterocyclic group, lower alkanoyl, lower alkoxy(lower)alkanoyl, heterocycliccarbonyl optionally substituted with lower alkyl, or lower alkylsulfonyl, and
$R^{13}$ is hydrogen, lower alkyl or heterocyclic(lower) alkyl, or
$R^{12}$ and $R^{13}$ are taken together with the attached nitrogen atom to form a heterocyclic group optionally substituted with oxo, and
Y is a single bond or —CO—.

5. A compound of claim 4, wherein
Q is a group of the formula:

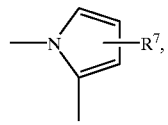

$A^2$ is methylene, and
$R^5$ is a group of the formula:

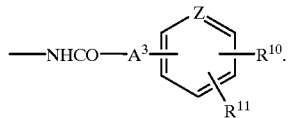

6. A process for preparing a compound of the formula:

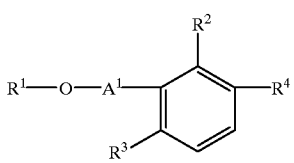

wherein:
$A^1$ is lower alkylene,
$R^1$ is imidazopyridyl, substituted with a substituent(s) selected from the group consisting of halogen, lower alkyl, lower alkoxy, lower alkylamino and a heterocyclic group,
$R^2$ is hydrogen, halogen or lower alkyl,
$R^3$ is halogen or lower alkyl, and
$R^4$ is carboxy, lower alkanoyl or a group of the formula:
—Q—$A^2$—$R^5$ or

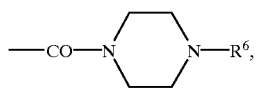

in which $R^5$ is amino, acylamino, cyano, hydroxy, hydroxyimino (lower)alkyl or acyl,
$R^6$ is hydrogen or acyl,
$A^2$ is lower alkylene or a single bond, and
Q is lower alkenylene or a group of the formula:

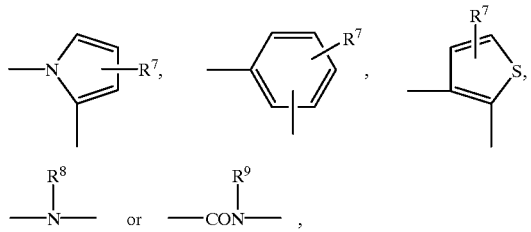

in which
$R^7$ is hydrogen or halogen;
$R^8$ is hydrogen, or
$R^8$ and $R^2$ are taken together to form lower alkylene; and
$R^9$ is hydrogen, lower alkyl or ar(lower)alkyl; provided that $A^2$ is lower alkylene when
$R^8$ is hydrogen,
or its salt, which comprises:
  a) reacting a compound of the formula:

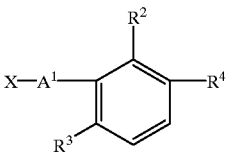

wherein X is a leaving group, and
$R^2$, $R^3$, $R^4$ and $A^1$ are each as defined above, or its salt with a compound of the formula:

$R^1$—OH wherein $R^1$ is as defined above,
or its salt, to give a compound of the formula:

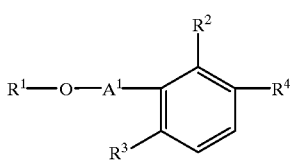

wherein $R^1$, $R^2$, $R^3$, $R^4$ and $A^1$ are each as defined above,
or its salt, or
  b) acylating a compound of the formula:

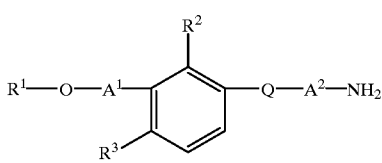

wherein $R^1$, $R^2$, $R^3$, $A^1$, $A^2$ and Q are each as defined above, or its salt, to give a compound of the formula:

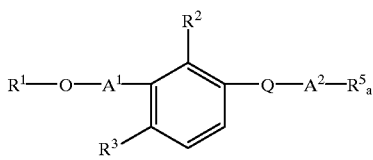

wherein $R_a^5$ is acylamino, and
$R^1$, $R^2$, $R^3$, $A^1$, $A^2$ and Q are each as defined above,
or its salt, or c) subjecting a compound of the formula:

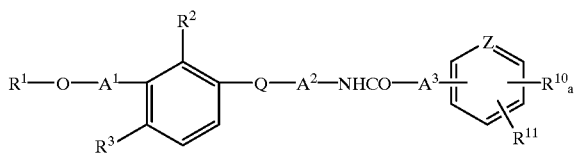

wherein $R_a^{10}$ is esterified carboxy,
$R^{11}$ is hydrogen, lower alkyl or lower alkoxy,
$A^3$ is —NH—, lower alkylene or lower alkenylene,
Z is CH or N, and
$R^1$, $R^2$, $R^3$, $A^1$, $A^2$ and Q are each as defined above,
or its salt, to a deesterification reaction to give a compound of the formula:

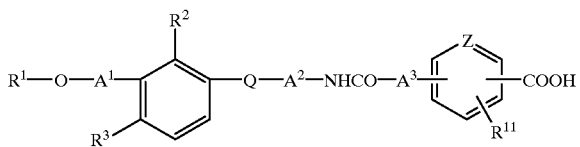

wherein $R^1$, $R^2$, $R^3$, $R^{11}$, $A^1$, $A^2$, $A^3$, Q and Z are each as defined above,
or its salt, or d) reacting a compound of the formula:

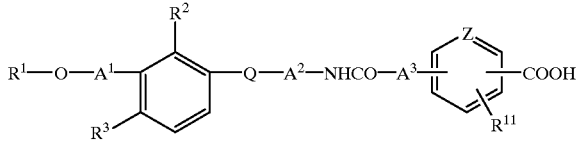

wherein $R^1$, $R^2$, $R^3$, $R^{11}$, $A^1$, $A^2$, $A^3$, Q and Z are each as defined above, or its reactive derivative at the carboxy group, or a salt thereof, with a compound of the formula:

wherein $R^{12}$ is hydrogen, lower alkyl, heterocyclic(lower)alkyl, a heterocyclic group, lower alkanoyl, lower alkoxy(lower)alkanoyl, heterocycliccarbonyl optionally substituted with lower alkyl, or lower alkylsulfonyl, and $R^{13}$ is hydrogen, lower alkyl or heterocyclic(lower)alkyl, or $R^{12}$ and $R^{13}$ are taken together with the attached nitrogen atom to form a heterocyclic group optionally substituted with oxo, or its salt, to give a compound of the formula:

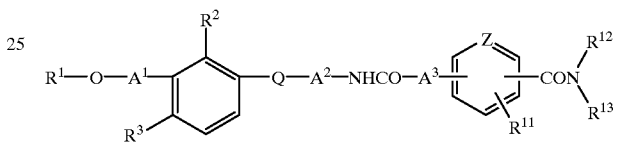

wherein $R^1$, $R^2$, $R^3$, $R^{11}$, $R^{12}$, $R^{13}$, $A^1$, $A^2$, $A^3$, Q and Z are each as defined above, or its salt.

7. A pharmaceutical composition comprising a compound of claim 1 in association with a pharmaceutically acceptable carrier or excipient.

8. The compound of claim 1, wherein $R^1$ is 2-(lower alkyl)-3-(halo)imidazo[1,2-a]pyridin-8-yl.

9. The compound 2-[(E)-3-(6-acetamidopyridin-3-yl)acryloylaminomethyl]-1-[2,4-dichloro-3-(3-bromo-2-methylimidazo[1,2-a]pyridin-8-yloxymethyl)phenyl]pyrrole.

10. A method for the prevention and/or the treatment of a disease mediated by bradykinin comprising administering an effective amount of a compound of claim 1 to a subject in need thereof.

11. A method of manufacturing a medicament comprising admixing a compound of claim 1 with a pharmaceutically acceptable carrier or excipient.

* * * * *